(12) United States Patent
Bernstein et al.

(10) Patent No.: US 10,370,643 B2
(45) Date of Patent: Aug. 6, 2019

(54) LILRB2 AND NOTCH-MEDIATED EXPANSION OF HEMATOPOIETIC PRECURSOR CELLS

(71) Applicants: FRED HUTCHINSON CANCER RESEARCH CENTER, Seattle, WA (US); BOARD OF REGENTS OF THE UNIVERSITY OF TEXAS SYSTEM, Austin, TX (US)

(72) Inventors: Irwin D. Bernstein, Seattle, WA (US); Chengcheng Zhang, Southlake, TX (US); Mi Deng, Plano, TX (US); Zhigang Lu, Irving, TX (US); Junke Zheng, Shanghai (CN)

(73) Assignees: Fred Hutchinson Cancer Research Center, Seattle, WA (US); Board of Regents of the University of Texas System, Austin, TX (US)

( * ) Notice: Subject to any disclaimer, the term of this patent is extended or adjusted under 35 U.S.C. 154(b) by 116 days.

(21) Appl. No.: 15/313,043

(22) PCT Filed: May 21, 2015

(86) PCT No.: PCT/US2015/031959
§ 371 (c)(1),
(2) Date: Nov. 21, 2016

(87) PCT Pub. No.: WO2015/179633
PCT Pub. Date: Nov. 26, 2015

(65) Prior Publication Data
US 2017/0260508 A1 Sep. 14, 2017

Related U.S. Application Data

(60) Provisional application No. 62/002,101, filed on May 22, 2014, provisional application No. 62/005,746, filed on May 30, 2014.

(51) Int. Cl.
| | |
|---|---|
| *C12N 5/071* | (2010.01) |
| *C12N 5/074* | (2010.01) |
| *C12N 5/078* | (2010.01) |
| *C12N 5/0797* | (2010.01) |
| *C07K 16/28* | (2006.01) |
| *C12N 5/0789* | (2010.01) |
| *C12N 5/0775* | (2010.01) |
| *G01N 33/569* | (2006.01) |

(52) U.S. Cl.
CPC ........ *C12N 5/0647* (2013.01); *C07K 16/2863* (2013.01); *C07K 16/2896* (2013.01); *C12N 5/0662* (2013.01); *G01N 33/56966* (2013.01); *C07K 16/28* (2013.01); *C12N 2500/90* (2013.01); *C12N 2501/113* (2013.01); *C12N 2501/125* (2013.01); *C12N 2501/145* (2013.01); *C12N 2501/17* (2013.01); *C12N 2501/2303* (2013.01); *C12N 2501/2306* (2013.01); *C12N 2501/26* (2013.01); *C12N 2501/42* (2013.01); *C12N 2501/599* (2013.01); *C12N 2501/91* (2013.01)

(58) Field of Classification Search
CPC .. A61K 38/00; A61K 2039/505; A61K 38/16; A61K 39/3955; A61K 38/177; A61K 39/395; A61K 38/179; A61K 38/1793; C07K 14/47; C07K 14/705; C07K 16/18; C07K 14/70596; C07K 16/28; C12N 2501/42; C12N 5/0647; C12N 2501/125; C12N 2501/145; C12N 2501/26; C12N 2501/2303; C12N 2501/2306
See application file for complete search history.

(56) References Cited

U.S. PATENT DOCUMENTS

| | | | |
|---|---|---|---|
| 2009/0081238 A1* | 3/2009 | Siebel | A61K 39/3955 424/172.1 |
| 2011/0196343 A1 | 8/2011 | Zhang et al. | |
| 2012/0315269 A1* | 12/2012 | Klechevsky | A61K 39/0011 424/133.1 |
| 2014/0017784 A1 | 1/2014 | Zhang et al. | |
| 2014/0286955 A1* | 9/2014 | Aifantis | C07K 16/28 424/139.1 |

FOREIGN PATENT DOCUMENTS

| | | |
|---|---|---|
| EP | 1899457 B1 | 9/2012 |
| WO | WO2008137641 A2 | 11/2008 |
| WO | WO2013086436 A1 | 6/2013 |
| WO | WO2013181438 A2 | 12/2013 |

OTHER PUBLICATIONS

Varnum-Finney et al. Immobilization of Notch ligand, Delta-1, is required for induction of Notch signaling. J Cell Sci 113: 4313-4318, 2000.*
Deng et al. A motif in LILRB2 critical for Angptl2 binding and activation. Blood 124(6): 924-935, Jun. 2014.*
Lin et al. Angiopoietin-like proteins stimulate HSPC development through interaction with notch receptor signaling. eLIFe 4: e05544, 2015.*
Lin et al. Angiopoietin-like proteins stimulate HSC development through direct interaction with Notch. Blood 122(21): 463, 2013.*
Xie et al. Ex vivo expansion of hematopoietic stem cells. Science China Life Sciences 58(9): 839-853, 2015.*

(Continued)

*Primary Examiner* — Bridget E Bunner
(74) *Attorney, Agent, or Firm* — Lee & Hayes PC; C. Rachal Winger; Thu Nguyen

(57) ABSTRACT

The current disclosure describes methods of expanding precursor cells for hematopoietic transplantation in subjects. The methods culture precursor cells in media containing an immobilized high molecular weight LILRB2 agonist or an LILRB2 agonist in combination with a Notch agonist. The expanded cells can be used to treat a variety of hematopoietic disorders.

19 Claims, 63 Drawing Sheets
Specification includes a Sequence Listing.

(56) References Cited

OTHER PUBLICATIONS

Masuda et al. Cis binding between inhibitory receptors and MHC class I can regulate mast cell activation. J Exp Med 204(4): 907-920, 2007.*

Kijima et al. Dendritic cell-mediated NK cell activation is controlled by Jagged2-Notch interaction. Proc Natl Acad Sci USA 105(19): 7010-7015, 2008.*

Sugimoto et al. Notch2 signaling is required for potent antitumor immunity in vivo. J Immunol 184: 4673-4678, 2010.*

Wang et al. Involvement of Notch1 signaling in neurogenesis in the subventricular zone of normal and ischemic rat brain in vivo. J Cerebral Blood Flow Metabol 29: 1644-1654, 2009.*

Delaney, et al., "Dose-dependent effects of the Notch ligand Delta1 on ex vivo differentiation and in vivo marrow repopulating ability of cord blood cells," Blood, vol. 106, No. 8, 2005, pp. 2693-2699.

Delaney, et al., "Notch-mediated expansion of human cord blood progenitor cells capable of rapid myeloid reconstitution," Nature Med., vol. 16, No. 2, 2010, pp. 232-236.

Hofmeister, et al., "Ex vivo expansion of umbilical cord blood stem cells for transplantation: growing knowledge from the hematopoietic niche", Bone Marrow Transplantation, vol. 39, 2007, pp. 11-23.

Huynh, et al., "Insulin-Like Growth Factor-Binding Protein 2 Secreted by a Tumorigenic Cell Line Supports Ex Vivo Expansion of Mouse Hematopoietic Stem Cells," Stem Cells, vol. 26, No. 6, 2008, pp. 1628-1635.

Milner, et al., "A human homologue of the *Drosophila* developmental gene, Notch, is expressed in CD34+ hematopoietic precursors," Blood, vol. 83, No. 8, 1994, pp. 2057-2062.

Search Report and Written Opinion dated Oct. 21, 2015 in International Application No. PCT/US15/31959.

Varnum-Finney, et al., "Pluripotent, cytokine-dependent, hematopoietic stem cells are immortalized by constitutive Notch1 signaling," Nat. Med., vol. 6, No. 11, 2000, pp. 1278-1281.

Varnum-Finney, et al., "Combined effects of Notch signaling and cytokines induce a multiple log increase in precursors with lymphoid and myeloid reconstituting ability," Blood, vol. 101, No. 5, 2003, pp. 1784-1789.

Zhang and Lodish, "Cytokines regulating hematopoietic stem cell function," Curr. Opin. Hematol., vol. 15, No. 4, 2008, pp. 307-311.

Zhang, et al., "Angiopoietin-like 5 and IGFBP2 stimulate ex vivo expansion of human cord blood hematopoietic stem cells as assayed by NOD/SCID transplantation", Blood, vol. 1, No. 7, 2008, pp. 3415-3423.

Zhang, et al., "Angiopoietin-like proteins stimulate ex vivo expansion of hematopoietic stem cells," Nat Med., vol. 12, No. 2, 2006, pp. 240-245.

Zheng, et al., "Angiopoietin-like protein 3 supports the activity of hematopoietic stem cells in the bone marrow niche," Blood, vol. 117, 2011, pp. 470-479.

Zheng, et al., "Ex vivo expanded hematopoietic stem cells overcome the MHC barrier in allogeneic transplantation," Cell Stem Cell., vol. 9, No. 2, 2011, pp. 119-130.

Zheng, et al., "Inhibitory receptors bind ANGPTLs and support blood stem cells and leukaemia development", Nature, vol. 485, 2012, pp. 656-663.

* cited by examiner

MTPIVTVLICLGLSLGPRTHVQ TIPKPFTLWAEPDSVITQGSPVTLSCQGSLEAQEYRLYREHKSASWITRIR
PELVKNGQFHIPSITWEHTGRYGCQYYSRARWSELSDPLLVLVMTGAYPKPTLSAQPSPVVTSGGRVTLQCE
SQVAEGGFILCKEGEEEHPQCLNSQPHARGSSRAIFSVGPVSPNRRWSHRCYGYDLNSPYVWSSPSDLLELL
VSGVSKKPSLSVQPGPVVAPGESLTLQCVSDVGYDRFVLYKEGERDLRQLPGRGPQAGLSQANFTLGPVSR
SYGGQYRCYGAHNLSECSAPSDPLDILITGQIRGTPFISVQPGPTVASGENVTLLCQSWRQFHTFLLTKAGA
ADAPLRLRSIHEYPKYQAEFPMSPVTSAHAGTYRCYGSINSDPYLLSHPSEPLELVVSGPSMGSPPPTGPIST
PGPEDQPLLTGSDPQSGLGRHLGVVIGILVAVVLLLLLLLLFLILRHRRQGKHWTSTQRKADFQHPAGAVG
PEPTDRGLQWRSSPAADAQEENLYAAVKDTQPEDGVEMDTRAAASEAPQDVTYAQLHSITLRRKATEPP
PSQEREPPAEPSIYATLAIH

Fig. 8A

Mut 1: L60A/Y61A
Mut 2: W69A/I70A
Mut 3: V78A
Mut 4: W90A
Mut 5: Y121A
Mut 6: V148A/F150A
Mut 7: D263A/L264A
Mut 8: Q320A/I321A/R322A
Mut 9: W348A/R349A/Q350A/F351A
Mut 10: Y374A/K376A/Y377A
Mut 11: L400A/N401A/S402A

Myeloid

Lymphoid

Progenitor/
Stem cells

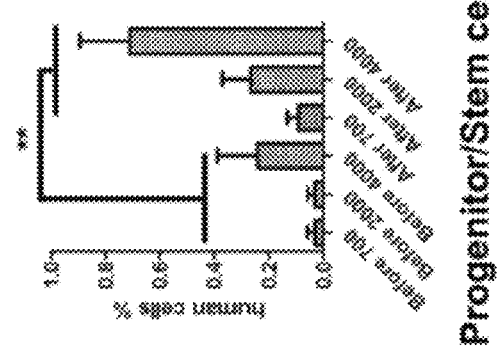
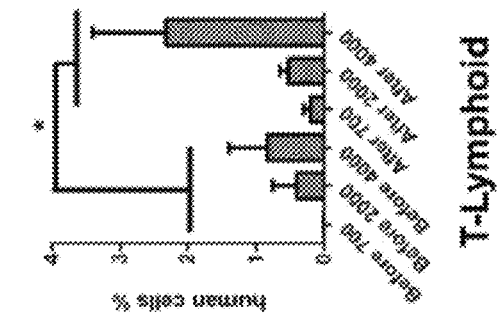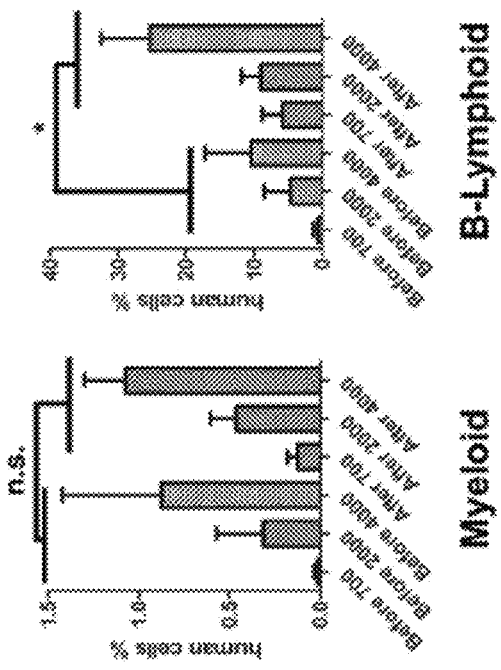

SEQUENCE LISTING

```
<160> NUMBER OF SEQ ID NOS: 20

<210> SEQ ID NO 1
<211> LENGTH: 21
<212> TYPE: PRT
<213> ORGANISM: Artificial Sequence
<220> FEATURE:
<223> OTHER INFORMATION: an optimized signal peptide used for expression
      construct

<400> SEQUENCE: 1

Met Trp Trp Arg Leu Trp Trp Leu Leu Leu Leu Leu Leu Leu Leu Trp
1               5                   10                  15

Pro Met Val Trp Ala
            20

<210> SEQ ID NO 2
<211> LENGTH: 597
<212> TYPE: PRT
<213> ORGANISM: Artificial Sequence
<220> FEATURE:
<223> OTHER INFORMATION: Mutated residues of LILRB2 in the possible
      ligand binding interface based on the known structure of LILRB2

<400> SEQUENCE: 2

Met Thr Pro Ile Val Thr Val Leu Ile Cys Leu Gly Leu Ser Leu Gly
1               5                   10                  15

Pro Arg Thr His Val Gln Thr Gly Thr Ile Pro Lys Pro Thr Leu Trp
                20                  25                  30

Ala Glu Pro Asp Ser Val Ile Thr Gln Gly Ser Pro Val Thr Leu Ser
            35                  40                  45

Cys Gln Gly Ser Leu Glu Ala Gln Glu Tyr Arg Leu Tyr Arg Glu Lys
        50                  55                  60

Lys Ser Ala Ser Trp Ile Thr Arg Ile Arg Pro Glu Leu Val Lys Asn
65                  70                  75                  80

Gly Gln Phe His Ile Pro Ser Ile Thr Trp Glu His Thr Gly Arg Tyr
                85                  90                  95

Gly Cys Gln Tyr Tyr Ser Arg Ala Arg Trp Ser Glu Leu Ser Asp Pro
            100                 105                 110

Leu Val Leu Val Met Thr Gly Ala Tyr Pro Lys Pro Thr Leu Ser Ala
            115                 120                 125
```

```
Gln Pro Ser Pro Val Val Thr Ser Gly Gly Arg Val Thr Leu Gln Cys
130                 135                 140

Glu Ser Gln Val Ala Phe Gly Gly Phe Ile Leu Cys Lys Glu Gly Glu
145                 150                 155                 160

Glu Glu His Pro Gln Cys Leu Asn Ser Gln Pro His Ala Arg Gly Ser
                165                 170                 175

Ser Arg Ala Ile Phe Ser Val Gly Pro Val Ser Pro Asn Arg Arg Trp
                180                 185                 190

Ser His Arg Cys Tyr Gly Tyr Asp Leu Asn Ser Pro Tyr Val Trp Ser
            195                 200                 205

Ser Pro Ser Asp Leu Leu Glu Leu Leu Val Pro Gly Val Ser Lys Lys
        210                 215                 220

Pro Ser Leu Ser Val Gln Pro Gly Pro Val Val Ala Pro Gly Glu Ser
225                 230                 235                 240

Leu Thr Leu Gln Cys Val Ser Asp Val Gly Tyr Asp Arg Phe Val Leu
                245                 250                 255

Tyr Lys Glu Gly Glu Arg Asp Leu Arg Gln Leu Pro Gly Arg Gln Pro
                260                 265                 270

Gln Ala Gly Leu Ser Gln Ala Asn Phe Thr Leu Gly Pro Val Ser Arg
            275                 280                 285

Ser Tyr Gly Gly Gln Tyr Arg Cys Tyr Gly Ala His Asn Leu Ser Ser
        290                 295                 300

Glu Cys Ser Ala Pro Ser Asp Pro Leu Asp Ile Leu Ile Thr Gly Gln
305                 310                 315                 320

Ile Arg Gly Thr Pro Phe Ile Ser Val Gln Pro Gly Pro Thr Val Ala
                325                 330                 335

Ser Gly Glu Asn Val Thr Leu Leu Cys Gln Ser Trp Arg Gln Phe His
                340                 345                 350

Thr Phe Leu Leu Thr Lys Ala Gly Ala Ala Asp Ala Pro Leu Arg Leu
            355                 360                 365

Arg Ser Ile His Glu Tyr Pro Lys Tyr Gln Ala Glu Phe Pro Met Ser
        370                 375                 380

Pro Val Thr Ser Ala His Ala Gly Thr Tyr Arg Cys Tyr Gly Ser Leu
385                 390                 395                 400

Asn Ser Asp Pro Tyr Leu Leu Ser His Pro Ser Glu Pro Leu Glu Leu
                405                 410                 415

Val Val Ser Gly Pro Ser Met Gly Ser Ser Pro Pro Thr Gly Pro
                420                 425                 430

Ile Ser Thr Pro Gly Pro Glu Asp Gln Pro Leu Thr Pro Thr Gly Ser
            435                 440                 445

Asp Pro Gln Ser Gly Leu Gly Arg His Leu Gly Val Val Ile Gly Ile
        450                 455                 460

Leu Val Ala Val Val Leu Leu Leu Leu Leu Leu Leu Leu Leu Phe Leu
465                 470                 475                 480

Ile Leu Arg His Arg Arg Gln Gly Lys His Trp Thr Ser Thr Gln Arg
                485                 490                 495

Lys Ala Asp Phe Gln His Pro Ala Gly Ala Val Gly Pro Glu Pro Thr
                500                 505                 510

Asp Arg Gly Leu Gln Trp Arg Ser Ser Pro Ala Ala Asp Ala Gln Glu
            515                 520                 525

Glu Asn Leu Tyr Ala Ala Val Lys Asp Thr Gln Pro Glu Asp Gly Val
        530                 535                 540
```

-continued

```
Glu Met Asp Thr Arg Ala Ala Ser Glu Ala Pro Gln Asp Val Thr
545                 550                 555                 560

Tyr Ala Gln Leu His Ser Leu Thr Leu Arg Arg Lys Ala Thr Glu Pro
            565                 570                 575

Pro Pro Ser Gln Glu Arg Glu Pro Ala Glu Pro Ser Ile Tyr Ala
        580                 585                 590

Thr Leu Ala Ile His
        595

<210> SEQ ID NO 3
<211> LENGTH: 455
<212> TYPE: PRT
<213> ORGANISM: Homo sapiens
<300> PUBLICATION INFORMATION:
<308> DATABASE ACCESSION NUMBER: NP_001265335.2
<309> DATABASE ENTRY DATE: 2015-03-15
<313> RELEVANT RESIDUES IN SEQ ID NO: (1)..(455)

<400> SEQUENCE: 3

Met Thr Pro Ile Val Thr Val Leu Ile Cys Leu Gly Leu Ser Leu Gly
1               5                   10                  15

Pro Arg Thr Arg Val Gln Thr Gly Thr Ile Pro Lys Pro Thr Leu Trp
            20                  25                  30

Ala Glu Pro Asp Ser Val Ile Thr Gln Gly Ser Pro Val Thr Leu Ser
        35                  40                  45

Cys Gln Gly Ser Leu Glu Ala Gln Glu Tyr Arg Leu Tyr Arg Glu Lys
    50                  55                  60

Lys Ser Ala Ser Trp Ile Thr Arg Ile Arg Pro Glu Leu Val Lys Asn
65                  70                  75                  80

Gly Gln Phe His Ile Pro Ser Ile Thr Trp Glu His Thr Gly Arg Tyr
                85                  90                  95

Gly Cys Gln Tyr Tyr Ser Arg Ala Arg Trp Ser Glu Leu Ser Asp Pro
            100                 105                 110

Leu Val Leu Val Met Thr Gly Ala Tyr Pro Lys Pro Thr Leu Ser Ala
        115                 120                 125

Gln Pro Ser Pro Val Val Thr Ser Gly Gly Arg Val Thr Leu Gln Cys
    130                 135                 140

Glu Ser Gln Val Ala Phe Gly Gly Phe Ile Leu Cys Lys Glu Gly Glu
145                 150                 155                 160

Asp Glu His Pro Gln Cys Leu Asn Ser Gln Pro His Ala Arg Gly Ser
                165                 170                 175

Ser Arg Ala Ile Phe Ser Val Gly Pro Val Ser Pro Asn Arg Arg Trp
            180                 185                 190

Ser His Arg Cys Tyr Gly Tyr Asp Leu Asn Ser Pro Tyr Val Trp Ser
        195                 200                 205

Ser Pro Ser Asp Leu Leu Glu Leu Leu Val Pro Gly Val Ser Lys Lys
    210                 215                 220

Pro Ser Leu Ser Val Gln Pro Gly Pro Val Met Ala Pro Gly Glu Ser
225                 230                 235                 240

Leu Thr Leu Gln Cys Val Ser Asp Val Gly Tyr Asp Arg Phe Val Leu
                245                 250                 255

Tyr Lys Glu Gly Glu Arg Asp Leu Arg Gln Leu Pro Gly Arg Gln Pro
            260                 265                 270

Gln Ala Gly Leu Ser Gln Ala Asn Phe Thr Leu Gly Pro Val Ser Arg
        275                 280                 285
```

-continued

```
Ser Tyr Gly Gly Gln Tyr Arg Cys Tyr Gly Ala His Asn Leu Ser Ser
    290                 295                 300

Glu Cys Ser Ala Pro Ser Asp Pro Leu Asp Ile Leu Ile Thr Gly Gln
305                 310                 315                 320

Ile Arg Gly Thr Pro Phe Ile Ser Val Gln Pro Gly Pro Thr Val Ala
                325                 330                 335

Ser Gly Glu Asn Val Thr Leu Leu Cys Gln Ser Trp Arg Gln Phe His
                340                 345                 350

Thr Phe Leu Leu Thr Lys Ala Gly Ala Ala Asp Ala Pro Leu Arg Leu
            355                 360                 365

Arg Ser Ile His Glu Tyr Pro Lys Tyr Gln Ala Glu Phe Pro Met Ser
370                 375                 380

Pro Val Thr Ser Ala His Ala Gly Thr Tyr Arg Cys Tyr Gly Ser Leu
385                 390                 395                 400

Asn Ser Asp Pro Tyr Leu Leu Ser His Pro Ser Glu Pro Leu Glu Leu
                405                 410                 415

Val Val Ser Gly Pro Ser Met Gly Ser Ser Pro Pro Thr Gly Pro
                420                 425                 430

Ile Ser Thr Pro Ala Gly Pro Glu Asp Gln Pro Leu Thr Pro Thr Gly
            435                 440                 445

Ser Asp Pro Gln Ser Gly Glu
450                 455

<210> SEQ ID NO 4
<211> LENGTH: 510
<212> TYPE: PRT
<213> ORGANISM: Homo sapiens
<300> PUBLICATION INFORMATION:
<308> DATABASE ACCESSION NUMBER: NP_001265334.2
<309> DATABASE ENTRY DATE: 2015-03-15
<313> RELEVANT RESIDUES IN SEQ ID NO: (1)..(510)

<400> SEQUENCE: 4

Met Thr Pro Ile Val Thr Val Leu Ile Cys Leu Gly Leu Ser Leu Gly
1               5                   10                  15

Pro Arg Thr Arg Val Gln Thr Gly Thr Ile Pro Lys Pro Thr Leu Trp
            20                  25                  30

Ala Glu Pro Asp Ser Val Ile Thr Gln Gly Ser Pro Val Thr Leu Ser
        35                  40                  45

Cys Gln Gly Ser Leu Glu Ala Gln Glu Tyr Arg Leu Tyr Arg Glu Lys
    50                  55                  60

Lys Ser Ala Ser Trp Ile Thr Arg Ile Arg Pro Glu Leu Val Lys Asn
65                  70                  75                  80

Gly Gln Phe His Ile Pro Ser Ile Thr Trp Glu His Thr Gly Arg Tyr
                85                  90                  95

Gly Cys Gln Tyr Tyr Ser Arg Ala Arg Trp Ser Glu Leu Ser Asp Pro
            100                 105                 110

Leu Val Leu Val Met Thr Gly Ala Tyr Pro Lys Pro Thr Leu Ser Ala
        115                 120                 125

Gln Pro Ser Pro Val Val Thr Ser Gly Gly Arg Val Thr Leu Gln Cys
    130                 135                 140

Glu Ser Gln Val Ala Phe Gly Gly Phe Ile Leu Cys Lys Glu Gly Glu
145                 150                 155                 160

Asp Glu His Pro Gln Cys Leu Asn Ser Gln Pro His Ala Arg Gly Ser
                165                 170                 175
```

```
Ser Arg Ala Ile Phe Ser Val Gly Pro Val Ser Pro Asn Arg Arg Trp
            180                 185                 190
Ser His Arg Cys Tyr Gly Tyr Asp Leu Asn Ser Pro Tyr Val Trp Ser
            195                 200                 205
Ser Pro Ser Asp Leu Leu Glu Leu Leu Val Pro Gly Val Ser Lys Lys
            210                 215                 220
Pro Ser Leu Ser Val Gln Pro Gly Pro Val Met Ala Pro Gly Glu Ser
225                 230                 235                 240
Leu Thr Leu Gln Cys Val Ser Asp Val Gly Tyr Asp Arg Phe Val Leu
            245                 250                 255
Tyr Lys Glu Gly Glu Arg Asp Leu Arg Gln Leu Pro Gly Arg Gln Pro
            260                 265                 270
Gln Ala Gly Leu Ser Gln Ala Asn Phe Thr Leu Gly Pro Val Ser Arg
            275                 280                 285
Ser Tyr Gly Gly Gln Tyr Arg Cys Tyr Gly Ala His Asn Leu Ser Ser
            290                 295                 300
Glu Cys Ser Ala Pro Ser Asp Pro Leu Asp Ile Leu Ile Thr Gly Gln
305                 310                 315                 320
Ile Arg Gly Thr Pro Phe Ile Ser Val Gln Pro Gly Pro Thr Val Ala
            325                 330                 335
Ser Gly Glu Asn Val Thr Leu Leu Cys Gln Ser Trp Arg Gln Phe His
            340                 345                 350
Thr Phe Leu Leu Thr Lys Ala Gly Ala Ala Asp Ala Pro Leu Arg Leu
            355                 360                 365
Arg Ser Ile His Glu Tyr Pro Lys Tyr Gln Ala Glu Phe Pro Met Ser
            370                 375                 380
Pro Val Thr Ser Ala His Ala Gly Thr Tyr Arg Cys Tyr Gly Ser Leu
385                 390                 395                 400
Asn Ser Asp Pro Tyr Leu Leu Ser His Pro Ser Glu Pro Leu Glu Leu
            405                 410                 415
Val Val Ser Gly Pro Ser Met Gly Ser Ser Pro Pro Thr Gly Pro
            420                 425                 430
Ile Ser Thr Pro Ala Gly Pro Glu Asp Gln Pro Leu Thr Pro Thr Gly
            435                 440                 445
Ser Asp Pro Gln Ser Gly Leu Gly Arg His Leu Gly Val Val Ile Gly
            450                 455                 460
Ile Leu Val Ala Val Leu Leu Leu Leu Leu Leu Leu Leu Leu Leu Phe
465                 470                 475                 480
Leu Ile Leu Arg His Arg Arg Gln Gly Lys His Trp Thr Ser Ser Pro
            485                 490                 495
Ala Gln Leu Pro Thr Pro Arg Lys Lys Thr Ser Met Leu Pro
            500                 505                 510

<210> SEQ ID NO 5
<211> LENGTH: 482
<212> TYPE: PRT
<213> ORGANISM: Homo sapiens
<300> PUBLICATION INFORMATION:
<308> DATABASE ACCESSION NUMBER: NP_001265333.2
<309> DATABASE ENTRY DATE: 2015-03-15
<313> RELEVANT RESIDUES IN SEQ ID NO: (1)..(482)
```

```
<400> SEQUENCE: 5

Met Thr Gly Ala Tyr Pro Lys Pro Thr Leu Ser Ala Gln Pro Ser Pro
1               5                   10                  15

Val Val Thr Ser Gly Gly Arg Val Thr Leu Gln Cys Glu Ser Gln Val
            20                  25                  30

Ala Phe Gly Gly Phe Ile Leu Cys Lys Glu Gly Glu Asp Glu His Pro
        35                  40                  45

Gln Cys Leu Asn Ser Gln Pro His Ala Arg Gly Ser Ser Arg Ala Ile
    50                  55                  60

Phe Ser Val Gly Pro Val Ser Pro Asn Arg Arg Trp Ser His Arg Cys
65                  70                  75                  80

Tyr Gly Tyr Asp Leu Asn Ser Pro Tyr Val Trp Ser Pro Ser Asp
                85                  90                  95

Leu Leu Glu Leu Leu Val Pro Gly Val Ser Lys Lys Pro Ser Leu Ser
                100                 105                 110

Val Gln Pro Gly Pro Val Met Ala Pro Gly Glu Ser Leu Thr Leu Gln
            115                 120                 125

Cys Val Ser Asp Val Gly Tyr Asp Arg Phe Val Leu Tyr Lys Glu Gly
    130                 135                 140

Glu Arg Asp Leu Arg Gln Leu Pro Gly Arg Gln Pro Gln Ala Gly Leu
145                 150                 155                 160

Ser Gln Ala Asn Phe Thr Leu Gly Pro Val Ser Arg Ser Tyr Gly Gly
                165                 170                 175

Gln Tyr Arg Cys Tyr Gly Ala His Asn Leu Ser Ser Glu Cys Ser Ala
                180                 185                 190

Pro Ser Asp Pro Leu Asp Ile Leu Ile Thr Gly Gln Ile Arg Gly Thr
            195                 200                 205

Pro Phe Ile Ser Val Gln Pro Gly Pro Thr Val Ala Ser Gly Glu Asn
            210                 215                 220

Val Thr Leu Leu Cys Gln Ser Trp Arg Gln Phe His Thr Phe Leu Leu
225                 230                 235                 240

Thr Lys Ala Gly Ala Ala Asp Ala Pro Leu Arg Leu Arg Ser Ile His
                245                 250                 255

Glu Tyr Pro Lys Tyr Gln Ala Glu Phe Pro Met Ser Pro Val Thr Ser
                260                 265                 270

Ala His Ala Gly Thr Tyr Arg Cys Tyr Gly Ser Leu Asn Ser Asp Pro
            275                 280                 285

Tyr Leu Leu Ser His Pro Ser Glu Pro Leu Glu Leu Val Val Ser Gly
            290                 295                 300

Pro Ser Met Gly Ser Ser Pro Pro Thr Gly Pro Ile Ser Thr Pro
305                 310                 315                 320

Ala Gly Pro Glu Asp Gln Pro Leu Thr Pro Thr Gly Ser Asp Pro Gln
            325                 330                 335

Ser Gly Leu Gly Arg His Leu Gly Val Val Ile Gly Ile Leu Val Ala
            340                 345                 350

Val Val Leu Leu Leu Leu Leu Leu Leu Phe Leu Ile Leu Arg
        355                 360                 365

His Arg Arg Gln Gly Lys His Trp Thr Ser Thr Gln Arg Lys Ala Asp
    370                 375                 380

Phe Gln His Pro Ala Gly Ala Val Gly Pro Glu Pro Thr Asp Arg Gly
385                 390                 395                 400

Leu Gln Trp Arg Ser Ser Pro Ala Ala Asp Ala Gln Glu Glu Asn Leu
                405                 410                 415
```

Tyr Ala Ala Val Lys Asp Thr Gln Pro Glu Asp Gly Val Glu Met Asp
                420                 425                 430

Thr Arg Ala Ala Ala Ser Glu Ala Pro Gln Asp Val Thr Tyr Ala Gln
            435                 440                 445

Leu His Ser Leu Thr Leu Arg Arg Lys Ala Thr Glu Pro Pro Pro Ser
        450                 455                 460

Gln Glu Arg Glu Pro Pro Ala Glu Pro Ser Ile Tyr Ala Thr Leu Ala
465                 470                 475                 480

Ile His

<210> SEQ ID NO 6
<211> LENGTH: 593
<212> TYPE: PRT
<213> ORGANISM: Homo sapiens
<300> PUBLICATION INFORMATION:
<308> DATABASE ACCESSION NUMBER: NP_001265333.2
<309> DATABASE ENTRY DATE: 2015-03-15
<313> RELEVANT RESIDUES IN SEQ ID NO: (1)..(482)

<400> SEQUENCE: 6

Met Thr Pro Ile Val Thr Val Leu Ile Cys Leu Gly Leu Ser Leu Gly
1               5                   10                  15

Pro Arg Thr Arg Val Gln Thr Gly Thr Ile Pro Lys Pro Thr Leu Trp
            20                  25                  30

Ala Glu Pro Asp Ser Val Ile Thr Gln Gly Ser Pro Val Thr Leu Ser
        35                  40                  45

Cys Gln Gly Ser Leu Glu Ala Gln Glu Tyr Arg Leu Tyr Arg Glu Lys
    50                  55                  60

Lys Ser Ala Ser Trp Ile Thr Arg Ile Arg Pro Glu Leu Val Lys Asn
65                  70                  75                  80

Gly Gln Phe His Ile Pro Ser Ile Thr Trp Glu His Thr Gly Arg Tyr
                85                  90                  95

Gly Cys Gln Tyr Tyr Ser Arg Ala Arg Trp Ser Glu Leu Ser Asp Pro
            100                 105                 110

Leu Val Leu Val Met Thr Gly Ala Tyr Pro Lys Pro Thr Leu Ser Ala
        115                 120                 125

Gln Pro Ser Pro Val Val Thr Ser Gly Gly Arg Val Thr Leu Gln Cys
    130                 135                 140

Glu Ser Gln Val Ala Phe Gly Gly Phe Ile Leu Cys Lys Glu Gly Glu
145                 150                 155                 160

Asp Glu His Pro Gln Cys Leu Asn Ser Gln Pro His Arg Ser Ser Arg
                165                 170                 175

Ala Ile Phe Ser Val Gly Pro Val Ser Pro Asn Arg Arg Trp Ser His
            180                 185                 190

Arg Cys Tyr Gly Tyr Asp Leu Asn Ser Pro Tyr Val Trp Ser Ser Pro
        195                 200                 205

Ser Asp Leu Leu Glu Leu Leu Val Pro Gly Val Ser Lys Lys Pro Ser
    210                 215                 220

Leu Ser Val Gln Pro Gly Pro Val Met Ala Pro Gly Glu Ser Leu Thr
225                 230                 235                 240

Leu Gln Cys Val Ser Asp Val Gly Tyr Asp Arg Phe Val Leu Tyr Lys
                245                 250                 255

Glu Gly Glu Arg Asp Leu Arg Gln Leu Pro Gly Arg Gln Pro Gln Ala
            260                 265                 270

Gly Leu Ser Gln Ala Asn Phe Thr Leu Gly Pro Val Ser Arg Ser Tyr
        275                 280                 285

```
Gly Gly Gln Tyr Arg Cys Tyr Gly Ala His Asn Leu Ser Ser Glu Cys
    290                 295                 300
Ser Ala Pro Ser Asp Pro Leu Asp Ile Leu Ile Thr Gly Gln Ile Arg
305                 310                 315                 320
Gly Thr Pro Phe Ile Ser Val Gln Pro Gly Pro Thr Val Ala Ser Gly
                325                 330                 335
Glu Asn Val Thr Leu Leu Cys Gln Ser Trp Arg Gln Phe His Thr Phe
            340                 345                 350
Leu Leu Thr Lys Ala Gly Ala Ala Asp Ala Pro Leu Arg Leu Arg Ser
        355                 360                 365
Ile His Glu Tyr Pro Lys Tyr Gln Ala Glu Phe Pro Met Ser Pro Val
370                 375                 380
Thr Ser Ala His Ala Gly Tyr Cys Tyr Gly Ser Leu Asn Ser Asp Pro
385                 390                 395                 400
Tyr Leu Leu Ser His Pro Ser Glu Pro Leu Glu Leu Val Val Ser Gly
                405                 410                 415
Pro Ser Met Gly Ser Ser Pro Pro Thr Gly Pro Ile Ser Thr Pro
            420                 425                 430
Gly Pro Glu Asp Gln Pro Leu Thr Pro Thr Gly Ser Asp Pro Gln Ser
        435                 440                 445
Gly Leu Gly Arg His Leu Gly Val Val Ile Gly Ile Leu Val Ala Val
450                 455                 460
Val Leu Leu Leu Leu Leu Leu Leu Leu Phe Leu Ile Leu Arg His
465                 470                 475                 480
Arg Arg Gln Gly Lys His Trp Thr Ser Thr Gln Arg Lys Ala Asp Phe
                485                 490                 495
Gln His Pro Ala Gly Ala Val Gly Pro Glu Pro Thr Asp Arg Gly Leu
            500                 505                 510
Gln Trp Arg Ser Ser Pro Ala Ala Asp Ala Gln Glu Glu Asn Leu Tyr
        515                 520                 525
Ala Ala Val Lys Asp Thr Gln Pro Glu Asp Gly Val Glu Met Asp Thr
530                 535                 540
Arg Ala Ala Ala Ser Glu Ala Pro Gln Asp Val Thr Tyr Ala Gln Leu
545                 550                 555                 560
His Ser Leu Thr Leu Arg Arg Lys Ala Thr Glu Pro Pro Pro Ser Gln
                565                 570                 575
Glu Arg Glu Pro Pro Ala Glu Pro Ser Ile Tyr Ala Thr Leu Ala Ile
            580                 585                 590
His
```

<210> SEQ ID NO 7
<211> LENGTH: 598
<212> TYPE: PRT
<213> ORGANISM: Homo sapiens
<300> PUBLICATION INFORMATION:
<308> DATABASE ACCESSION NUMBER: AAH36827.1
<309> DATABASE ENTRY DATE: 2007-03-06
<313> RELEVANT RESIDUES IN SEQ ID NO: (1)..(598)

<400> SEQUENCE: 7

```
Met Thr Pro Ile Val Thr Val Leu Ile Cys Leu Gly Leu Ser Leu Gly
1               5                   10                  15
Pro Arg Thr His Val Gln Thr Gly Thr Ile Pro Lys Pro Thr Leu Trp
            20                  25                  30
Ala Glu Pro Asp Ser Val Ile Thr Gln Gly Ser Pro Val Thr Leu Ser
        35                  40                  45
```

```
Cys Gln Gly Ser Leu Glu Ala Gln Glu Tyr Arg Leu Tyr Arg Glu Lys
 50                  55                  60
Lys Ser Ala Ser Trp Ile Thr Arg Ile Arg Pro Glu Leu Val Lys Asn
 65                  70                  75                  80
Gly Gln Phe His Ile Pro Ser Ile Thr Trp Glu His Thr Gly Arg Tyr
                     85                  90                  95
Gly Cys Gln Tyr Tyr Ser Arg Ala Arg Trp Ser Glu Leu Ser Asp Pro
                    100                 105                 110
Leu Val Leu Val Met Thr Gly Ala Tyr Pro Lys Pro Thr Leu Ser Ala
                115                 120                 125
Gln Pro Ser Pro Val Val Thr Ser Gly Gly Arg Val Thr Leu Gln Cys
130                 135                 140
Glu Ser Gln Val Ala Phe Gly Gly Phe Ile Leu Cys Lys Glu Gly Glu
145                 150                 155                 160
Asp Glu His Pro Gln Cys Leu Asn Ser Gln Pro His Ala Arg Gly Ser
                    165                 170                 175
Ser Arg Ala Ile Phe Ser Val Gly Pro Val Ser Pro Asn Arg Arg Trp
                180                 185                 190
Ser His Arg Cys Tyr Gly Tyr Asp Leu Asn Ser Pro Tyr Val Trp Ser
                195                 200                 205
Ser Pro Ser Asp Leu Leu Glu Leu Leu Val Pro Gly Val Ser Lys Lys
210                 215                 220
Pro Ser Leu Ser Val Gln Pro Gly Pro Val Val Ala Pro Gly Glu Ser
225                 230                 235                 240
Leu Thr Leu Gln Cys Val Ser Asp Val Gly Tyr Asp Arg Phe Val Leu
                245                 250                 255
Tyr Lys Glu Gly Glu Arg Asp Leu Arg Gln Leu Pro Gly Arg Gln Pro
                260                 265                 270
Gln Ala Gly Leu Ser Gln Ala Asn Phe Thr Leu Gly Pro Val Ser Arg
                275                 280                 285
Ser Tyr Gly Gly Gln Tyr Arg Cys Tyr Gly Ala Tyr Asn Leu Ser Ser
                290                 295                 300
Glu Trp Ser Ala Pro Ser Asp Pro Leu Asp Ile Leu Ile Thr Gly Gln
305                 310                 315                 320
Ile His Gly Thr Pro Phe Ile Ser Val Gln Pro Gly Pro Thr Val Ala
                325                 330                 335
Ser Gly Glu Asn Val Thr Leu Leu Cys Gln Ser Trp Arg Gln Phe His
                340                 345                 350
Thr Phe Leu Leu Thr Lys Ala Gly Ala Ala Asp Ala Pro Leu Arg Leu
                355                 360                 365
Arg Ser Ile His Glu Tyr Pro Lys Tyr Gln Ala Glu Phe Pro Met Ser
                370                 375                 380
Pro Val Thr Ser Ala His Ala Gly Thr Tyr Arg Cys Tyr Gly Ser Leu
385                 390                 395                 400
Asn Ser Asp Pro Tyr Leu Leu Ser His Pro Ser Glu Pro Leu Glu Leu
                405                 410                 415
Val Val Ser Gly Pro Ser Met Gly Ser Ser Pro Pro Thr Gly Pro
                420                 425                 430
Ile Ser Thr Pro Ala Gly Pro Glu Asp Gln Pro Leu Thr Pro Thr Gly
                435                 440                 445
Ser Asp Pro Gln Ser Gly Leu Gly Arg His Leu Gly Val Val Ile Gly
450                 455                 460
```

Ile Leu Val Ala Val Val Leu Leu Leu Leu Leu Leu Leu Phe
465                 470                 475                 480

Leu Ile Leu Arg His Arg Arg Gln Gly Lys His Trp Thr Ser Thr Gln
        485                 490                 495

Arg Lys Ala Asp Phe Gln His Pro Ala Gly Ala Val Gly Pro Glu Pro
            500                 505                 510

Thr Asp Arg Gly Leu Gln Trp Arg Ser Ser Pro Ala Ala Asp Ala Gln
            515                 520                 525

Glu Glu Asn Leu Tyr Ala Ala Val Lys Asp Thr Gln Pro Glu Asp Gly
530                 535                 540

Val Glu Met Asp Thr Arg Ala Ala Ala Ser Glu Ala Pro Gln Asp Val
545                 550                 555                 560

Thr Tyr Ala Gln Leu His Ser Leu Thr Leu Arg Arg Lys Ala Thr Glu
                565                 570                 575

Pro Pro Pro Ser Gln Glu Gly Glu Pro Pro Ala Glu Pro Ser Ile Tyr
            580                 585                 590

Ala Thr Leu Ala Ile His
            595

<210> SEQ ID NO 8
<211> LENGTH: 493
<212> TYPE: PRT
<213> ORGANISM: Homo sapiens
<300> PUBLICATION INFORMATION:
<308> DATABASE ACCESSION NUMBER: AAH12368.1
<309> DATABASE ENTRY DATE: 2006-07-15
<313> RELEVANT RESIDUES IN SEQ ID NO: (1)..(493)

<400> SEQUENCE: 8

Met Arg Pro Leu Cys Val Thr Cys Trp Trp Leu Gly Leu Leu Ala Ala
1               5                   10                  15

Met Gly Ala Val Ala Gly Gln Glu Asp Gly Phe Glu Gly Thr Glu Glu
            20                  25                  30

Gly Ser Pro Arg Glu Phe Ile Tyr Leu Asn Arg Tyr Lys Arg Ala Gly
        35                  40                  45

Glu Ser Gln Asp Lys Cys Thr Tyr Thr Phe Ile Val Pro Gln Gln Arg
50                  55                  60

Val Thr Gly Ala Ile Cys Val Asn Ser Lys Glu Pro Glu Val Leu Leu
65                  70                  75                  80

Glu Asn Arg Val His Lys Gln Glu Leu Glu Leu Leu Asn Asn Glu Leu
                85                  90                  95

Leu Lys Gln Lys Arg Gln Ile Glu Thr Leu Gln Gln Leu Val Glu Val
            100                 105                 110

Asp Gly Gly Ile Val Ser Glu Val Lys Leu Leu Arg Lys Glu Ser Arg
        115                 120                 125

Asn Met Asn Ser Arg Val Thr Gln Leu Tyr Met Gln Leu Leu His Glu
130                 135                 140

Ile Ile Arg Lys Arg Asp Asn Ala Leu Glu Leu Ser Gln Leu Glu Asn
145                 150                 155                 160

Arg Ile Leu Asn Gln Thr Ala Asp Met Leu Gln Leu Ala Ser Lys Tyr
                165                 170                 175

Lys Asp Leu Glu His Lys Tyr Gln His Leu Ala Thr Leu Ala His Asn
            180                 185                 190

Gln Ser Glu Ile Ile Ala Gln Leu Glu Glu His Cys Gln Arg Val Pro
        195                 200                 205

-continued

Ser Ala Arg Pro Val Pro Gln Pro Pro Ala Ala Pro Pro Arg Val
210                 215                 220

Tyr Gln Pro Pro Thr Tyr Asn Arg Ile Ile Asn Gln Ile Ser Thr Asn
225                 230                 235                 240

Glu Ile Gln Ser Asp Gln Asn Leu Lys Val Leu Pro Pro Leu Pro
            245                 250                 255

Thr Met Pro Thr Leu Thr Ser Leu Pro Ser Ser Thr Asp Lys Pro Ser
        260                 265                 270

Gly Pro Trp Arg Asp Cys Leu Gln Ala Leu Glu Asp Gly His Asp Thr
            275                 280                 285

Ser Ser Ile Tyr Leu Val Lys Pro Glu Asn Thr Asn Arg Leu Met Gln
290                 295                 300

Val Trp Cys Asp Gln Arg His Asp Pro Gly Gly Trp Thr Val Ile Gln
305                 310                 315                 320

Arg Arg Leu Asp Gly Ser Val Asn Phe Phe Arg Asn Trp Glu Thr Tyr
            325                 330                 335

Lys Gln Gly Phe Gly Asn Ile Asp Gly Glu Tyr Trp Leu Gly Leu Glu
        340                 345                 350

Asn Ile Tyr Trp Leu Thr Asn Gln Gly Asn Tyr Lys Leu Leu Val Thr
355                 360                 365

Met Glu Asp Trp Ser Gly Arg Lys Val Phe Ala Glu Tyr Ala Ser Phe
370                 375                 380

Arg Leu Glu Pro Glu Ser Glu Tyr Tyr Lys Leu Arg Leu Gly Arg Tyr
385                 390                 395                 400

His Gly Asn Ala Gly Asp Ser Phe Thr Trp His Asn Gly Lys Gln Phe
            405                 410                 415

Thr Thr Leu Asp Arg Asp His Asp Val Tyr Thr Gly Asn Cys Ala His
        420                 425                 430

Tyr Gln Lys Gly Gly Trp Trp Tyr Asn Ala Cys Ala His Ser Asn Leu
            435                 440                 445

Asn Gly Val Trp Tyr Arg Gly Gly His Tyr Arg Ser Arg Tyr Gln Asp
450                 455                 460

Gly Val Tyr Trp Ala Glu Phe Arg Gly Gly Ser Tyr Ser Leu Lys Lys
465                 470                 475                 480

Val Val Met Met Ile Arg Pro Asn Pro Asn Thr Phe His
                485                 490

<210> SEQ ID NO 9
<211> LENGTH: 460
<212> TYPE: PRT
<213> ORGANISM: Homo sapiens
<300> PUBLICATION INFORMATION:
<308> DATABASE ACCESSION NUMBER: AAH58287.1
<309> DATABASE ENTRY DATE: 2006-07-15
<313> RELEVANT RESIDUES IN SEQ ID NO: (1)..(460)

<400> SEQUENCE: 9

Met Phe Thr Ile Lys Leu Leu Phe Ile Val Pro Leu Val Ile Ser
1               5                   10                  15

Ser Arg Ile Asp Gln Asp Asn Ser Ser Phe Asp Ser Leu Ser Pro Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
50                  55                  60

-continued

```
Lys Gly Gln Ile Asn Asp Ile Phe Gln Lys Leu Asn Ile Phe Asp Gln
 65                  70                  75                  80

Ser Phe Tyr Asp Leu Ser Leu Gln Thr Ser Glu Ile Lys Glu Glu
                 85                  90                  95

Lys Glu Leu Arg Arg Thr Thr Tyr Lys Leu Gln Val Lys Asn Glu Glu
                100                 105                 110

Val Lys Asn Met Ser Leu Glu Leu Asn Ser Lys Leu Glu Ser Leu Leu
                115                 120                 125

Glu Glu Lys Ile Leu Leu Gln Gln Lys Val Lys Tyr Leu Glu Glu Gln
            130                 135                 140

Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
                165                 170                 175

Asp Leu Leu Gln Thr Val Glu Asp Gln Tyr Lys Gln Leu Asn Gln Gln
                180                 185                 190

His Ser Gln Ile Lys Glu Ile Glu Asn Gln Leu Arg Arg Thr Ser Ile
                195                 200                 205

Gln Glu Pro Thr Glu Ile Ser Leu Ser Ser Lys Pro Arg Ala Pro Arg
            210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                245                 250                 255

Ser Gly Met Tyr Ala Ile Arg Pro Ser Asn Ser Gln Val Phe His Val
                260                 265                 270

Tyr Cys Asp Val Ile Ser Gly Ser Pro Trp Thr Leu Ile Gln His Arg
                275                 280                 285

Ile Asp Gly Ser Gln Asn Phe Asn Glu Thr Trp Glu Asn Tyr Lys Tyr
            290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
                325                 330                 335

Asp Trp Lys Asp Asn Lys His Tyr Ile Glu Tyr Ser Phe Tyr Leu Gly
                340                 345                 350

Asn His Glu Thr Asn Tyr Thr Leu His Leu Val Ala Ile Thr Gly Asn
            355                 360                 365

Val Pro Asn Ala Ile Pro Glu Asn Lys Asp Leu Val Phe Ser Thr Trp
370                 375                 380

Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
                405                 410                 415

Tyr Asn Lys Pro Arg Ala Lys Ser Lys Pro Glu Arg Arg Arg Gly Leu
                420                 425                 430

Ser Trp Lys Ser Gln Asn Gly Arg Leu Tyr Ser Ile Lys Ser Thr Lys
            435                 440                 445

Met Leu Ile His Pro Thr Asp Ser Glu Ser Phe Glu
450                 455                 460
```

-continued

<210> SEQ ID NO 10
<211> LENGTH: 406
<212> TYPE: PRT
<213> ORGANISM: Homo sapiens
<300> PUBLICATION INFORMATION:
<308> DATABASE ACCESSION NUMBER: AAH23647
<309> DATABASE ENTRY DATE: 2006-07-15
<313> RELEVANT RESIDUES IN SEQ ID NO: (1)..(406)

<400> SEQUENCE: 10

```
Met Ser Gly Ala Pro Thr Gly Ala Ala Leu Met Leu Cys Ala Ala
1               5                   10                  15

Thr Ala Val Leu Leu Ser Ala Gln Gly Gly Pro Val Gln Ser Lys Ser
            20                  25                  30

Pro Arg Phe Ala Ser Trp Asp Glu Met Asn Val Leu Ala His Gly Leu
            35                  40                  45

Leu Gln Leu Gly Gln Gly Leu Arg Glu His Ala Glu Arg Thr Arg Ser
    50                  55                  60

Gln Leu Ser Ala Leu Glu Arg Arg Leu Ser Ala Cys Gly Ser Ala Cys
65                  70                  75                  80

Gln Gly Thr Glu Gly Ser Thr Asp Leu Pro Leu Ala Pro Glu Ser Arg
                85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
        115                 120                 125

His Leu Glu Lys Gln His Leu Arg Ile Gln His Leu Gln Ser Gln Phe
    130                 135                 140

Gly Leu Leu Asp His Lys His Leu Asp His Glu Val Ala Lys Pro Ala
145                 150                 155                 160

Arg Arg Lys Arg Leu Pro Glu Met Ala Gln Pro Val Asp Pro Ala His
                165                 170                 175

Asn Val Ser Arg Leu His Arg Leu Pro Arg Asp Cys Gln Glu Leu Phe
            180                 185                 190

Gln Val Gly Glu Arg Gln Ser Gly Leu Phe Glu Ile Gln Pro Gln Gly
        195                 200                 205

Ser Pro Pro Phe Leu Val Asn Cys Lys Met Thr Ser Asp Gly Gly Trp
    210                 215                 220

Thr Val Ile Gln Arg Arg His Asp Gly Ser Val Asp Phe Asn Arg Pro
225                 230                 235                 240

Trp Glu Ala Tyr Lys Ala Gly Phe Gly Asp Pro His Gly Glu Phe Trp
                245                 250                 255

Leu Gly Leu Glu Lys Val His Ser Ile Thr Gly Asp Arg Asn Ser Arg
            260                 265                 270

Leu Ala Val Gln Leu Arg Asp Trp Asp Gly Asn Ala Glu Leu Leu Gln
        275                 280                 285

Phe Ser Val His Leu Gly Gly Glu Asp Thr Ala Tyr Ser Leu Gln Leu
    290                 295                 300

Thr Ala Pro Val Ala Gly Gln Leu Gly Ala Thr Thr Val Pro Pro Ser
305                 310                 315                 320

Gly Leu Ser Val Pro Phe Ser Thr Trp Asp Gln Asp His Asp Leu Arg
                325                 330                 335

Arg Asp Lys Asn Cys Ala Lys Ser Leu Ser Gly Gly Trp Trp Phe Gly
            340                 345                 350

Thr Cys Ser His Ser Asn Leu Asn Gly Gln Tyr Phe Arg Ser Ile Pro
        355                 360                 365
```

-continued

```
Gln Gln Arg Gln Lys Leu Lys Lys Gly Ile Phe Trp Lys Thr Trp Arg
    370                 375                 380

Gly Arg Tyr Tyr Pro Leu Gln Ala Thr Thr Met Leu Ile Gln Pro Met
385                 390                 395                 400

Ala Ala Glu Ala Ala Ser
                405

<210> SEQ ID NO 11
<211> LENGTH: 388
<212> TYPE: PRT
<213> ORGANISM: Homo sapiens
<300> PUBLICATION INFORMATION:
<308> DATABASE ACCESSION NUMBER: AAH49170
<309> DATABASE ENTRY DATE: 2006-07-17
<313> RELEVANT RESIDUES IN SEQ ID NO: (1)..(388)

<400> SEQUENCE: 11

Met Met Ser Pro Ser Gln Ala Ser Leu Leu Phe Leu Asn Val Cys Ile
1               5                   10                  15

Phe Ile Cys Gly Glu Ala Val Gln Gly Asn Cys Val His His Ser Thr
            20                  25                  30

Asp Ser Ser Val Val Asn Ile Val Glu Asp Gly Ser Asn Ala Lys Asp
        35                  40                  45

Glu Ser Lys Ser Asn Asp Thr Val Cys Lys Glu Asp Cys Glu Glu Ser
    50                  55                  60

Cys Asp Val Lys Thr Lys Ile Thr Arg Glu Glu Lys His Phe Met Cys
65                  70                  75                  80

Arg Asn Leu Gln Asn Ser Ile Val Ser Tyr Thr Arg Ser Thr Lys Lys
                85                  90                  95

Leu Leu Arg Asn Met Met Asp Glu Gln Gln Ala Ser Leu Asp Tyr Leu
            100                 105                 110

Ser Asn Gln Val Asn Glu Leu Met Asn Arg Val Leu Leu Leu Thr Thr
        115                 120                 125

Glu Val Phe Arg Lys Gln Leu Asp Pro Phe Pro His Arg Pro Val Gln
    130                 135                 140

Ser His Gly Leu Asp Cys Thr Asp Ile Lys Asp Thr Ile Gly Ser Val
145                 150                 155                 160

Thr Lys Thr Pro Ser Gly Leu Tyr Ile Ile His Pro Glu Gly Ser Ser
                165                 170                 175

Tyr Pro Phe Glu Val Met Cys Asp Met Asp Tyr Arg Gly Gly Gly Trp
            180                 185                 190

Thr Val Ile Gln Lys Arg Ile Asp Gly Ile Ile Asp Phe Gln Arg Leu
        195                 200                 205

Trp Cys Asp Tyr Leu Asp Gly Phe Gly Asp Leu Leu Gly Glu Phe Trp
    210                 215                 220

Leu Gly Leu Lys Lys Ile Phe Tyr Ile Val Asn Gln Lys Asn Thr Ser
225                 230                 235                 240

Phe Met Leu Tyr Val Ala Leu Glu Ser Glu Asp Asp Thr Leu Ala Tyr
                245                 250                 255

Ala Ser Tyr Asp Asn Phe Trp Leu Glu Asp Glu Thr Arg Phe Phe Lys
            260                 265                 270

Met His Leu Gly Arg Tyr Ser Gly Asn Ala Gly Asp Ala Phe Arg Gly
        275                 280                 285

Leu Lys Lys Glu Asp Asn Gln Asn Ala Met Pro Phe Ser Thr Ser Asp
    290                 295                 300
```

```
Val Asp Asn Asp Gly Cys Arg Pro Ala Cys Leu Val Asn Gly Gln Ser
305                 310                 315                 320

Val Lys Ser Cys Ser His Leu His Asn Lys Thr Gly Trp Trp Phe Asn
            325                 330                 335

Glu Cys Gly Leu Ala Asn Leu Asn Gly Ile His His Phe Ser Gly Lys
            340                 345                 350

Leu Leu Ala Thr Gly Ile Gln Trp Gly Thr Trp Thr Lys Asn Asn Ser
            355                 360                 365

Pro Val Lys Ile Lys Ser Val Ser Met Lys Ile Arg Arg Met Tyr Asn
    370                 375                 380

Pro Tyr Phe Lys
385

<210> SEQ ID NO 12
<211> LENGTH: 346
<212> TYPE: PRT
<213> ORGANISM: Homo sapiens
<300> PUBLICATION INFORMATION:
<308> DATABASE ACCESSION NUMBER: AAH01881
<309> DATABASE ENTRY DATE: 2006-07-15
<313> RELEVANT RESIDUES IN SEQ ID NO: (1)..(346)

<400> SEQUENCE: 12

Met Leu Lys Lys Pro Leu Ser Ala Val Thr Trp Leu Cys Ile Phe Ile
1               5                   10                  15

Val Ala Phe Val Ser His Pro Ala Trp Leu Gln Lys Leu Ser Lys His
            20                  25                  30

Lys Thr Pro Ala Gln Pro Gln Leu Lys Ala Ala Asn Cys Cys Glu Glu
        35                  40                  45

Val Lys Glu Leu Lys Ala Gln Val Ala Asn Leu Ser Ser Leu Leu Ser
    50                  55                  60

Glu Leu Asn Lys Lys Gln Glu Arg Asp Trp Val Ser Val Val Met Gln
65                  70                  75                  80

Val Met Glu Leu Glu Ser Asn Ser Lys Arg Met Glu Ser Arg Leu Thr
                85                  90                  95

Asp Ala Glu Ser Lys Tyr Ser Glu Met Asn Asn Gln Ile Asp Ile Met
            100                 105                 110

Gln Leu Gln Ala Ala Gln Thr Val Thr Gln Thr Ser Ala Asp Ala Ile
        115                 120                 125

Tyr Asp Cys Ser Ser Leu Tyr Gln Lys Asn Tyr Arg Ile Ser Gly Val
    130                 135                 140

Tyr Lys Leu Pro Pro Asp Asp Phe Leu Gly Ser Pro Glu Leu Glu Val
145                 150                 155                 160

Phe Cys Asp Met Glu Thr Ser Gly Gly Gly Trp Thr Ile Ile Gln Arg
                165                 170                 175

Arg Lys Ser Gly Leu Val Ser Phe Tyr Arg Asp Trp Lys Gln Tyr Lys
            180                 185                 190

Gln Gly Phe Gly Ser Ile Arg Gly Asp Phe Trp Leu Gly Asn Glu His
        195                 200                 205

Ile His Arg Leu Ser Arg Gln Pro Thr Arg Leu Arg Val Glu Met Glu
    210                 215                 220

Asp Trp Glu Gly Asn Leu Arg Tyr Ala Glu Tyr Ser His Phe Val Leu
225                 230                 235                 240

Gly Asn Glu Leu Asn Ser Tyr Arg Leu Phe Leu Gly Asn Tyr Thr Gly
                245                 250                 255
```

Asn Val Gly Asn Asp Ala Leu Gln Tyr His Asn Asn Thr Ala Phe Ser
            260                 265                 270

Thr Lys Asp Lys Asp Asn Asp Asn Cys Leu Asp Lys Cys Ala Gln Leu
        275                 280                 285

Arg Lys Gly Gly Tyr Trp Tyr Asn Cys Cys Thr Asp Ser Asn Leu Asn
        290                 295                 300

Gly Val Tyr Tyr Arg Leu Gly Glu His Asn Lys His Leu Asp Gly Ile
305                 310                 315                 320

Thr Trp Tyr Gly Trp His Gly Ser Thr Tyr Ser Leu Lys Arg Val Glu
                325                 330                 335

Met Lys Ile Arg Pro Glu Asp Phe Lys Pro
        340                 345

<210> SEQ ID NO 13
<211> LENGTH: 255
<212> TYPE: PRT
<213> ORGANISM: Homo sapiens
<300> PUBLICATION INFORMATION:
<308> DATABASE ACCESSION NUMBER: NP_002395
<309> DATABASE ENTRY DATE: 2015-03-15
<313> RELEVANT RESIDUES IN SEQ ID NO: (1)..(255)

<400> SEQUENCE: 13

Met Lys Ala Leu Leu Ala Leu Pro Leu Leu Leu Leu Ser Thr Pro
1               5                   10                  15

Pro Cys Ala Pro Gln Val Ser Gly Ile Arg Gly Asp Ala Leu Glu Arg
            20                  25                  30

Phe Cys Leu Gln Gln Pro Leu Asp Cys Asp Asp Ile Tyr Ala Gln Gly
        35                  40                  45

Tyr Gln Ser Asp Gly Val Tyr Leu Ile Tyr Pro Ser Gly Pro Ser Val
    50                  55                  60

Pro Val Pro Val Phe Cys Asp Met Thr Thr Glu Gly Gly Lys Trp Thr
65                  70                  75                  80

Val Phe Gln Lys Arg Phe Asn Gly Ser Val Ser Phe Arg Gly Trp
                85                  90                  95

Asn Asp Tyr Lys Leu Gly Phe Gly Arg Ala Asp Gly Glu Tyr Trp Leu
            100                 105                 110

Gly Leu Gln Asn Met His Leu Leu Thr Leu Lys Gln Lys Tyr Glu Leu
        115                 120                 125

Arg Val Asp Leu Glu Asp Phe Glu Asn Asn Thr Ala Tyr Ala Lys Tyr
    130                 135                 140

Ala Asp Phe Ser Ile Ser Pro Asn Ala Val Ser Ala Glu Glu Asp Gly
145                 150                 155                 160

Tyr Thr Leu Phe Val Ala Gly Phe Glu Asp Gly Gly Ala Gly Asp Ser
                165                 170                 175

Leu Ser Tyr His Ser Gly Gln Lys Phe Ser Thr Phe Asp Arg Asp Gln
            180                 185                 190

Asp Leu Phe Val Gln Asn Cys Ala Ala Leu Ser Ser Gly Ala Phe Trp
        195                 200                 205

Phe Arg Ser Cys His Phe Ala Asn Leu Asn Gly Phe Tyr Leu Gly Gly
    210                 215                 220

Ser His Leu Ser Tyr Ala Asn Gly Ile Asn Trp Ala Gln Trp Lys Gly
225                 230                 235                 240

Phe Tyr Tyr Ser Leu Lys Arg Thr Glu Met Lys Ile Arg Arg Ala
                245                 250                 255

-continued

```
<210> SEQ ID NO 14
<211> LENGTH: 2555
<212> TYPE: PRT
<213> ORGANISM: Homo sapiens
<300> PUBLICATION INFORMATION:
<308> DATABASE ACCESSION NUMBER: P46531.4
<309> DATABASE ENTRY DATE: 2015-04-29
<313> RELEVANT RESIDUES IN SEQ ID NO: (1)..(2555)

<400> SEQUENCE: 14
```

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
                20                  25                  30

Asn Gly Gly Lys Cys Glu Ala Ala Asn Gly Thr Glu Ala Cys Val Cys
            35                  40                  45

Gly Gly Ala Phe Val Gly Pro Arg Cys Gln Asp Pro Asn Pro Cys Leu
        50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
                100                 105                 110

Asn Gly Gly Thr Cys Asp Leu Leu Thr Leu Thr Glu Tyr Lys Cys Arg
            115                 120                 125

Cys Pro Pro Gly Trp Ser Gly Lys Ser Cys Gln Gln Ala Asp Pro Cys
        130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175

Gln Asp Val Asn Glu Cys Gly Gln Lys Pro Gly Leu Cys Arg His Gly
                180                 185                 190

Gly Thr Cys His Asn Glu Val Gly Ser Tyr Arg Cys Val Cys Arg Ala
            195                 200                 205

Thr His Thr Gly Pro Asn Cys Glu Arg Pro Tyr Val Pro Cys Ser Pro
        210                 215                 220

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
                245                 250                 255

Asn Ile Asp Asp Cys Pro Gly Asn Asn Cys Lys Asn Gly Gly Ala Cys
                260                 265                 270

Val Asp Gly Val Asn Thr Tyr Asn Cys Arg Cys Pro Pro Glu Trp Thr
            275                 280                 285

Gly Gln Tyr Cys Thr Glu Asp Val Asp Glu Cys Gln Leu Met Pro Asn
        290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Ala Cys Phe His Gly Ala Thr Cys His Asp
                340                 345                 350

Arg Val Ala Ser Phe Tyr Cys Glu Cys Pro His Gly Arg Thr Gly Leu
            355                 360                 365

```
Leu Cys His Leu Asn Asp Ala Cys Ile Ser Asn Pro Cys Asn Glu Gly
    370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
                405                 410                 415

Ser Leu Gly Ala Asn Pro Cys Glu His Ala Gly Lys Cys Ile Asn Thr
            420                 425                 430

Leu Gly Ser Phe Glu Cys Gln Cys Leu Gln Gly Tyr Thr Gly Pro Arg
        435                 440                 445

Cys Glu Ile Asp Val Asn Glu Cys Val Ser Asn Pro Cys Gln Asn Asp
    450                 455                 460

Ala Thr Cys Leu Asp Gln Ile Gly Glu Phe Gln Cys Ile Cys Met Pro
465                 470                 475                 480

Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
            500                 505                 510

Gln Cys Glu Cys Pro Thr Gly Phe Thr Gly His Leu Cys Gln Tyr Asp
        515                 520                 525

Val Asp Glu Cys Ala Ser Thr Pro Cys Lys Asn Gly Ala Lys Cys Leu
    530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Arg
            580                 585                 590

Pro Gly Tyr Thr Gly His His Cys Glu Thr Asn Ile Asn Glu Cys Ser
        595                 600                 605

Ser Gln Pro Cys Arg His Gly Gly Thr Cys Gln Asp Arg Asp Asn Ala
    610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Ile Asn Ile Asp Glu Cys Ala Gly Asn Pro Cys His
        675                 680                 685

Asn Gly Gly Thr Cys Glu Asp Gly Ile Asn Gly Phe Thr Cys Arg Cys
    690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765

Lys Asp Met Thr Ser Gly Tyr Val Cys Thr Cys Arg Glu Gly Phe Ser
    770                 775                 780
```

-continued

```
Gly Pro Asn Cys Gln Thr Asn Ile Asn Glu Cys Ala Ser Asn Pro Cys
785             790             795             800

Leu Asn Gln Gly Thr Cys Ile Asp Asp Val Ala Gly Tyr Lys Cys Asn
            805             810             815

Cys Leu Leu Pro Tyr Thr Gly Ala Thr Cys Glu Val Val Leu Ala Pro
            820             825             830

Cys Ala Pro Ser Pro Cys Arg Asn Gly Gly Glu Cys Arg Gln Ser Glu
            835             840             845

Asp Tyr Glu Ser Phe Ser Cys Val Cys Pro Thr Gly Trp Gln Gly Gln
            850             855             860

Thr Cys Glu Val Asp Ile Asn Glu Cys Val Leu Ser Pro Cys Arg His
865             870             875             880

Gly Ala Ser Cys Gln Asn Thr His Gly Gly Tyr Arg Cys His Cys Gln
            885             890             895

Ala Gly Tyr Ser Gly Arg Asn Cys Glu Thr Asp Ile Asp Asp Cys Arg
            900             905             910

Pro Asn Pro Cys His Asn Gly Gly Ser Cys Thr Asp Gly Ile Asn Thr
            915             920             925

Ala Phe Cys Asp Cys Leu Pro Gly Phe Arg Gly Thr Phe Cys Glu Glu
            930             935             940

Asp Ile Asn Glu Cys Ala Ser Asp Pro Cys Arg Asn Gly Ala Asn Cys
945             950             955             960

Thr Asp Cys Val Asp Ser Tyr Thr Cys Thr Cys Pro Ala Gly Phe Ser
            965             970             975

Gly Ile His Cys Glu Asn Asn Thr Pro Asp Cys Thr Glu Ser Ser Cys
            980             985             990

Phe Asn Gly Gly Thr Cys Val Asp Gly Ile Asn Ser Phe Thr Cys Leu
            995             1000            1005

Cys Pro Pro Gly Phe Thr Gly Ser Tyr Cys Gln His Asp Val Asn
            1010            1015            1020

Glu Cys Asp Ser Gln Pro Cys Leu His Gly Gly Thr Cys Gln Asp
            1025            1030            1035

Gly Cys Gly Ser Tyr Arg Cys Thr Cys Pro Gln Gly Tyr Thr Gly
            1040            1045            1050

Pro Asn Cys Gln Asn Leu Val His Trp Cys Asp Ser Ser Pro Cys
            1055            1060            1065

Lys Asn Gly Gly Lys Cys Trp Gln Thr His Thr Gln Tyr Arg Cys
            1070            1075            1080

Glu Cys Pro Ser Gly Trp Thr Gly Leu Tyr Cys Asp Val Pro Ser
            1085            1090            1095

Val Ser Cys Glu Val Ala Ala Gln Arg Gln Gly Val Asp Val Ala
            1100            1105            1110

Arg Leu Cys Gln His Gly Gly Leu Cys Val Asp Ala Gly Asn Thr
            1115            1120            1125

His His Cys Arg Cys Gln Ala Gly Tyr Thr Gly Ser Tyr Cys Glu
            1130            1135            1140

Asp Leu Val Asp Glu Cys Ser Pro Ser Pro Cys Gln Asn Gly Ala
            1145            1150            1155

Thr Cys Thr Asp Tyr Leu Gly Gly Tyr Ser Cys Lys Cys Val Ala
            1160            1165            1170

Gly Tyr His Gly Val Asn Cys Ser Glu Glu Ile Asp Glu Cys Leu
            1175            1180            1185
```

```
Ser His Pro Cys Gln Asn Gly Gly Thr Cys Leu Asp Leu Pro Asn
    1190                1195                1200

Thr Tyr Lys Cys Ser Cys Pro Arg Gly Thr Gln Gly Val His Cys
    1205                1210                1215

Glu Ile Asn Val Asp Asp Cys Asn Pro Pro Val Asp Pro Val Ser
    1220                1225                1230

Arg Ser Pro Lys Cys Phe Asn Asn Gly Thr Cys Val Asp Gln Val
    1235                1240                1245

Gly Gly Tyr Ser Cys Thr Cys Pro Pro Gly Phe Val Gly Glu Arg
    1250                1255                1260

Cys Glu Gly Asp Val Asn Glu Cys Leu Ser Asn Pro Cys Asp Ala
    1265                1270                1275

Arg Gly Thr Gln Asn Cys Val Gln Arg Val Asn Asp Phe His Cys
    1280                1285                1290

Glu Cys Arg Ala Gly His Thr Gly Arg Arg Cys Glu Ser Val Ile
    1295                1300                1305

Asn Gly Cys Lys Gly Lys Pro Cys Lys Asn Gly Gly Thr Cys Ala
    1310                1315                1320

Val Ala Ser Asn Thr Ala Arg Gly Phe Ile Cys Lys Cys Pro Ala
    1325                1330                1335

Gly Phe Glu Gly Ala Thr Cys Glu Asn Asp Ala Arg Thr Cys Gly
    1340                1345                1350

Ser Leu Arg Cys Leu Asn Gly Gly Thr Cys Ile Ser Gly Pro Arg
    1355                1360                1365

Ser Pro Thr Cys Leu Cys Leu Gly Pro Phe Thr Gly Pro Glu Cys
    1370                1375                1380

Gln Phe Pro Ala Ser Ser Pro Cys Leu Gly Gly Asn Pro Cys Tyr
    1385                1390                1395

Asn Gln Gly Thr Cys Glu Pro Thr Ser Glu Ser Pro Phe Tyr Arg
    1400                1405                1410

Cys Leu Cys Pro Ala Lys Phe Asn Gly Leu Leu Cys His Ile Leu
    1415                1420                1425

Asp Tyr Ser Phe Gly Gly Gly Ala Gly Arg Asp Ile Pro Pro Pro
    1430                1435                1440

Leu Ile Glu Glu Ala Cys Glu Leu Pro Glu Cys Gln Glu Asp Ala
    1445                1450                1455

Gly Asn Lys Val Cys Ser Leu Gln Cys Asn Asn His Ala Cys Gly
    1460                1465                1470

Trp Asp Gly Gly Asp Cys Ser Leu Asn Phe Asn Asp Pro Trp Lys
    1475                1480                1485

Asn Cys Thr Gln Ser Leu Gln Cys Trp Lys Tyr Phe Ser Asp Gly
    1490                1495                1500

His Cys Asp Ser Gln Cys Asn Ser Ala Gly Cys Leu Phe Asp Gly
    1505                1510                1515

Phe Asp Cys Gln Arg Ala Glu Gly Gln Cys Asn Pro Leu Tyr Asp
    1520                1525                1530

Gln Tyr Cys Lys Asp His Phe Ser Asp Gly His Cys Asp Gln Gly
    1535                1540                1545

Cys Asn Ser Ala Glu Cys Glu Trp Asp Gly Leu Asp Cys Ala Glu
    1550                1555                1560

His Val Pro Glu Arg Leu Ala Ala Gly Thr Leu Val Val Val Val
    1565                1570                1575
```

```
Leu Met Pro Pro Glu Gln Leu Arg Asn Ser Ser Phe His Phe Leu
    1580            1585                1590

Arg Glu Leu Ser Arg Val Leu His Thr Asn Val Val Phe Lys Arg
1595                1600                1605

Asp Ala His Gly Gln Gln Met Ile Phe Pro Tyr Tyr Gly Arg Glu
1610                1615                1620

Glu Glu Leu Arg Lys His Pro Ile Lys Arg Ala Ala Glu Gly Trp
1625                1630                1635

Ala Ala Pro Asp Ala Leu Leu Gly Gln Val Lys Ala Ser Leu Leu
1640                1645                1650

Pro Gly Gly Ser Glu Gly Gly Arg Arg Arg Glu Leu Asp Pro
1655                1660                1665

Met Asp Val Arg Gly Ser Ile Val Tyr Leu Glu Ile Asp Asn Arg
1670                1675                1680

Gln Cys Val Gln Ala Ser Ser Gln Cys Phe Gln Ser Ala Thr Asp
1685                1690                1695

Val Ala Ala Phe Leu Gly Ala Leu Ala Ser Leu Gly Ser Leu Asn
1700                1705                1710

Ile Pro Tyr Lys Ile Glu Ala Val Gln Ser Glu Thr Val Glu Pro
1715                1720                1725

Pro Pro Pro Ala Gln Leu His Phe Met Tyr Val Ala Ala Ala Ala
1730                1735                1740

Phe Val Leu Leu Phe Phe Val Gly Cys Gly Val Leu Leu Ser Arg
1745                1750                1755

Lys Arg Arg Arg Gln His Gly Gln Leu Trp Phe Pro Glu Gly Phe
1760                1765                1770

Lys Val Ser Glu Ala Ser Lys Lys Arg Arg Glu Pro Leu Gly
1775                1780                1785

Glu Asp Ser Val Gly Leu Lys Pro Leu Lys Asn Ala Ser Asp Gly
1790                1795                1800

Ala Leu Met Asp Asp Asn Gln Asn Glu Trp Gly Asp Glu Asp Leu
1805                1810                1815

Glu Thr Lys Lys Phe Arg Phe Glu Glu Pro Val Val Leu Pro Asp
1820                1825                1830

Leu Asp Asp Gln Thr Asp His Arg Gln Trp Thr Gln Gln His Leu
1835                1840                1845

Asp Ala Ala Asp Leu Arg Met Ser Ala Met Ala Pro Thr Pro Pro
1850                1855                1860

Gln Gly Glu Val Asp Ala Asp Cys Met Asp Val Asn Val Arg Gly
1865                1870                1875

Pro Asp Gly Phe Thr Pro Leu Met Ile Ala Ser Cys Ser Gly Gly
1880                1885                1890

Gly Leu Glu Thr Gly Asn Ser Glu Glu Glu Asp Ala Pro Ala
1895                1900                1905

Val Ile Ser Asp Phe Ile Tyr Gln Gly Ala Ser Leu His Asn Gln
1910                1915                1920

Thr Asp Arg Thr Gly Glu Thr Ala Leu His Leu Ala Ala Arg Tyr
1925                1930                1935

Ser Arg Ser Asp Ala Ala Lys Arg Leu Leu Glu Ala Ser Ala Asp
1940                1945                1950

Ala Asn Ile Gln Asp Asn Met Gly Arg Thr Pro Leu His Ala Ala
1955                1960                1965
```

```
Val Ser Ala Asp Ala Gln Gly Val Phe Gln Ile Leu Ile Arg Asn
1970                1975                1980

Arg Ala Thr Asp Leu Asp Ala Arg Met His Asp Gly Thr Thr Pro
1985                1990                1995

Leu Ile Leu Ala Ala Arg Leu Ala Val Glu Gly Met Leu Glu Asp
2000                2005                2010

Leu Ile Asn Ser His Ala Asp Val Asn Ala Val Asp Asp Leu Gly
2015                2020                2025

Lys Ser Ala Leu His Trp Ala Ala Val Asn Asn Val Asp Ala
2030                2035                2040

Ala Val Val Leu Leu Lys Asn Gly Ala Asn Lys Asp Met Gln Asn
2045                2050                2055

Asn Arg Glu Glu Thr Pro Leu Phe Leu Ala Ala Arg Glu Gly Ser
2060                2065                2070

Tyr Glu Thr Ala Lys Val Leu Leu Asp His Phe Ala Asn Arg Asp
2075                2080                2085

Ile Thr Asp His Met Asp Arg Leu Pro Arg Asp Ile Ala Gln Glu
2090                2095                2100

Arg Met His His Asp Ile Val Arg Leu Leu Asp Glu Tyr Asn Leu
2105                2110                2115

Val Arg Ser Pro Gln Leu His Gly Ala Pro Leu Gly Gly Thr Pro
2120                2125                2130

Thr Leu Ser Pro Pro Leu Cys Ser Pro Asn Gly Tyr Leu Gly Ser
2135                2140                2145

Leu Lys Pro Gly Val Gln Gly Lys Lys Val Arg Lys Pro Ser Ser
2150                2155                2160

Lys Gly Leu Ala Cys Gly Ser Lys Glu Ala Lys Asp Leu Lys Ala
2165                2170                2175

Arg Arg Lys Lys Ser Gln Asp Gly Lys Gly Cys Leu Leu Asp Ser
2180                2185                2190

Ser Gly Met Leu Ser Pro Val Asp Ser Leu Glu Ser Pro His Gly
2195                2200                2205

Tyr Leu Ser Asp Val Ala Ser Pro Pro Leu Leu Pro Ser Pro Phe
2210                2215                2220

Gln Gln Ser Pro Ser Val Pro Leu Asn His Leu Pro Gly Met Pro
2225                2230                2235

Asp Thr His Leu Gly Ile Gly His Leu Asn Val Ala Ala Lys Pro
2240                2245                2250

Glu Met Ala Ala Leu Gly Gly Gly Gly Arg Leu Ala Phe Glu Thr
2255                2260                2265

Gly Pro Pro Arg Leu Ser His Leu Pro Val Ala Ser Gly Thr Ser
2270                2275                2280

Thr Val Leu Gly Ser Ser Ser Gly Gly Ala Leu Asn Phe Thr Val
2285                2290                2295

Gly Gly Ser Thr Ser Leu Asn Gly Gln Cys Glu Trp Leu Ser Arg
2300                2305                2310

Leu Gln Ser Gly Met Val Pro Asn Gln Tyr Asn Pro Leu Arg Gly
2315                2320                2325

Ser Val Ala Pro Gly Pro Leu Ser Thr Gln Ala Pro Ser Leu Gln
2330                2335                2340

His Gly Met Val Gly Pro Leu His Ser Ser Leu Ala Ala Ser Ala
2345                2350                2355
```

-continued

Leu Ser Gln Met Met Ser Tyr Gln Gly Leu Pro Ser Thr Arg Leu
2360                2365                2370

Ala Thr Gln Pro His Leu Val Gln Thr Gln Gln Val Gln Pro Gln
    2375                2380                2385

Asn Leu Gln Met Gln Gln Gln Asn Leu Gln Pro Ala Asn Ile Gln
    2390                2395                2400

Gln Gln Gln Ser Leu Gln Pro Pro Pro Pro Pro Gln Pro His
2405                2410                2415

Leu Gly Val Ser Ser Ala Ala Ser Gly His Leu Gly Arg Ser Phe
    2420                2425                2430

Leu Ser Gly Glu Pro Ser Gln Ala Asp Val Gln Pro Leu Gly Pro
    2435                2440                2445

Ser Ser Leu Ala Val His Thr Ile Leu Pro Gln Glu Ser Pro Ala
    2450                2455                2460

Leu Pro Thr Ser Leu Pro Ser Ser Leu Val Pro Val Thr Ala
    2465                2470                2475

Ala Gln Phe Leu Thr Pro Pro Ser Gln His Ser Tyr Ser Ser Pro
    2480                2485                2490

Val Asp Asn Thr Pro Ser His Gln Leu Gln Val Pro Glu His Pro
    2495                2500                2505

Phe Leu Thr Pro Ser Pro Glu Ser Pro Asp Gln Trp Ser Ser Ser
    2510                2515                2520

Ser Pro His Ser Asn Val Ser Asp Trp Ser Glu Gly Val Ser Ser
    2525                2530                2535

Pro Pro Thr Ser Met Gln Ser Gln Ile Ala Arg Ile Pro Glu Ala
    2540                2545                2550

Phe Lys
    2555

<210> SEQ ID NO 15
<211> LENGTH: 723
<212> TYPE: PRT
<213> ORGANISM: Homo sapiens
<300> PUBLICATION INFORMATION:
<308> DATABASE ACCESSION NUMBER: AAG09716.1
<309> DATABASE ENTRY DATE: 2000-09-02
<313> RELEVANT RESIDUES IN SEQ ID NO: (1)..(723)

<400> SEQUENCE: 15

Met Gly Ser Arg Cys Ala Leu Ala Leu Ala Val Leu Ser Ala Leu Leu
1               5                   10                  15

Cys Gln Val Trp Ser Ser Gly Val Phe Glu Leu Lys Leu Gln Glu Phe
            20                  25                  30

Val Asn Lys Lys Gly Leu Leu Gly Asn Arg Asn Cys Cys Arg Gly Gly
        35                  40                  45

Ala Gly Pro Pro Pro Cys Ala Cys Arg Thr Phe Phe Arg Val Cys Leu
    50                  55                  60

Lys His Tyr Gln Ala Ser Val Ser Pro Glu Pro Pro Cys Thr Tyr Gly
65                  70                  75                  80

Ser Ala Val Thr Pro Val Leu Gly Val Asp Ser Phe Ser Leu Pro Asp
                85                  90                  95

Gly Gly Gly Ala Asp Ser Ala Phe Ser Asn Pro Ile Arg Phe Pro Phe
                100                 105                 110

Gly Phe Thr Trp Pro Gly Thr Phe Ser Leu Ile Ile Glu Ala Leu His
            115                 120                 125

```
Thr Asp Ser Pro Asp Asp Leu Ala Thr Glu Asn Pro Glu Arg Leu Ile
    130                 135                 140

Ser Arg Leu Ala Thr Gln Arg His Leu Thr Val Gly Glu Glu Trp Ser
145                 150                 155                 160

Gln Asp Leu His Ser Ser Gly Arg Thr Asp Leu Lys Tyr Ser Tyr Arg
                165                 170                 175

Phe Val Cys Asp Glu His Tyr Tyr Gly Glu Gly Cys Ser Val Phe Cys
            180                 185                 190

Arg Pro Arg Asp Asp Ala Phe Gly His Phe Thr Cys Gly Glu Arg Gly
        195                 200                 205

Glu Lys Val Cys Asn Pro Gly Trp Lys Gly Pro Tyr Cys Thr Glu Pro
    210                 215                 220

Ile Cys Leu Pro Gly Cys Asp Glu Gln His Gly Phe Cys Asp Lys Pro
225                 230                 235                 240

Gly Glu Cys Lys Cys Arg Val Gly Trp Gln Gly Arg Tyr Cys Asp Glu
                245                 250                 255

Cys Ile Arg Tyr Pro Gly Cys Leu His Gly Thr Cys Gln Gln Pro Trp
            260                 265                 270

Gln Cys Asn Cys Gln Glu Gly Trp Gly Gly Leu Phe Cys Asn Gln Asp
        275                 280                 285

Leu Asn Tyr Cys Thr His His Lys Pro Cys Lys Asn Gly Ala Thr Cys
    290                 295                 300

Thr Asn Thr Gly Gln Gly Ser Tyr Thr Cys Ser Cys Arg Pro Gly Tyr
305                 310                 315                 320

Thr Gly Ala Thr Cys Glu Leu Gly Ile Asp Glu Cys Asp Pro Ser Pro
                325                 330                 335

Cys Lys Asn Gly Gly Ser Cys Thr Asp Leu Glu Asn Ser Tyr Ser Cys
            340                 345                 350

Thr Cys Pro Pro Gly Phe Tyr Gly Lys Ile Cys Glu Leu Ser Ala Met
        355                 360                 365

Thr Cys Ala Asp Gly Pro Cys Phe Asn Gly Gly Arg Cys Ser Asp Ser
    370                 375                 380

Pro Asp Gly Gly Tyr Ser Cys Arg Cys Pro Val Gly Tyr Ser Gly Phe
385                 390                 395                 400

Asn Cys Glu Lys Lys Ile Asp Tyr Cys Ser Ser Ser Pro Cys Ser Asn
                405                 410                 415

Gly Ala Lys Cys Val Asp Leu Gly Asp Ala Tyr Leu Cys Arg Cys Gln
            420                 425                 430

Ala Gly Phe Ser Gly Arg His Cys Asp Asp Asn Val Asp Asp Cys Ala
        435                 440                 445

Ser Ser Pro Cys Ala Asn Gly Gly Thr Cys Arg Asp Gly Val Asn Asp
    450                 455                 460

Phe Ser Cys Thr Cys Pro Pro Gly Tyr Thr Gly Arg Asn Cys Ser Ala
465                 470                 475                 480

Pro Val Ser Arg Cys Glu His Ala Pro Cys His Asn Gly Ala Thr Cys
                485                 490                 495

His Glu Arg Gly His Gly Tyr Val Cys Glu Cys Ala Arg Gly Tyr Gly
            500                 505                 510

Gly Pro Asn Cys Gln Phe Leu Leu Pro Glu Leu Pro Pro Gly Pro Ala
        515                 520                 525

Val Val Asp Leu Thr Glu Lys Leu Glu Gly Gln Gly Gly Pro Phe Pro
    530                 535                 540
```

```
Trp Val Ala Val Cys Ala Gly Val Ile Leu Val Leu Met Leu Leu Leu
545                 550                 555                 560

Gly Cys Ala Ala Val Val Cys Val Arg Leu Arg Leu Gln Lys His
            565                 570                 575

Arg Pro Pro Ala Asp Pro Cys Arg Gly Glu Thr Glu Thr Met Asn Asn
                580                 585                 590

Leu Ala Asn Cys Gln Arg Glu Lys Asp Ile Ser Val Ser Ile Ile Gly
            595                 600                 605

Ala Thr Gln Ile Lys Asn Thr Asn Lys Lys Ala Asp Phe His Gly Asp
            610                 615                 620

His Ser Ala Asp Lys Asn Gly Phe Lys Ala Arg Tyr Pro Ala Val Asp
625                 630                 635                 640

Tyr Asn Leu Val Gln Asp Leu Lys Gly Asp Asp Thr Ala Val Arg Asp
                645                 650                 655

Ala His Ser Lys Arg Asp Thr Lys Cys Gln Pro Gln Gly Ser Ser Gly
            660                 665                 670

Glu Glu Lys Gly Thr Pro Thr Thr Leu Arg Gly Gly Glu Ala Ser Glu
            675                 680                 685

Arg Lys Arg Pro Asp Ser Gly Cys Ser Thr Ser Lys Asp Thr Lys Tyr
690                 695                 700

Gln Ser Val Tyr Val Ile Ser Glu Glu Lys Asp Glu Cys Val Ile Ala
705                 710                 715                 720

Thr Glu Val

<210> SEQ ID NO 16
<211> LENGTH: 44
<212> TYPE: PRT
<213> ORGANISM: Homo sapiens
<300> PUBLICATION INFORMATION:
<308> DATABASE ACCESSION NUMBER: 2KB9_A
<309> DATABASE ENTRY DATE: 2012-10-10
<313> RELEVANT RESIDUES IN SEQ ID NO: (1)..(44)

<400> SEQUENCE: 16

Arg Cys Gln Tyr Gly Trp Gln Gly Leu Tyr Cys Asp Lys Cys Ile Pro
1               5                   10                  15

His Pro Gly Cys Val His Gly Ile Cys Asn Glu Pro Trp Gln Cys Leu
                20                  25                  30

Cys Glu Thr Asn Trp Gly Gly Gln Leu Cys Asp Lys
            35                  40

<210> SEQ ID NO 17
<211> LENGTH: 169
<212> TYPE: PRT
<213> ORGANISM: Homo sapiens
<300> PUBLICATION INFORMATION:
<308> DATABASE ACCESSION NUMBER: 2VJ2_B
<309> DATABASE ENTRY DATE: 2012-10-10
<313> RELEVANT RESIDUES IN SEQ ID NO: (1)..(169)

<400> SEQUENCE: 17

Met Arg Gly Ser His His His His His His Gly Ser Ile Glu Gly Arg
1               5                   10                  15

Ser Ala Val Thr Cys Asp Asp Tyr Tyr Tyr Gly Phe Gly Cys Asn Lys
                20                  25                  30

Phe Cys Arg Pro Arg Asp Asp Phe Phe Gly His Tyr Ala Cys Asp Gln
            35                  40                  45

Asn Gly Asn Lys Thr Cys Met Glu Gly Trp Met Gly Pro Glu Cys Asn
50                  55                  60
```

-continued

```
Arg Ala Ile Cys Arg Gln Gly Cys Ser Pro Lys His Gly Ser Cys Lys
65                  70                  75                  80

Leu Pro Gly Asp Cys Arg Cys Gln Tyr Gly Trp Gln Gly Leu Tyr Cys
                85                  90                  95

Asp Lys Cys Ile Pro His Pro Gly Cys Val His Gly Ile Cys Asn Glu
            100                 105                 110

Pro Trp Gln Cys Leu Cys Glu Thr Asn Trp Gly Gly Gln Leu Cys Asp
        115                 120                 125

Lys Asp Leu Asn Tyr Cys Gly Thr His Gln Pro Cys Leu Asn Gly Gly
    130                 135                 140

Thr Cys Ser Asn Thr Gly Pro Asp Lys Tyr Gln Cys Ser Cys Pro Glu
145                 150                 155                 160

Gly Tyr Ser Gly Pro Asn Cys Glu Ile
                165

<210> SEQ ID NO 18
<211> LENGTH: 9
<212> TYPE: PRT
<213> ORGANISM: Artificial Sequence
<220> FEATURE:
<223> OTHER INFORMATION: H*G*Y*C motif in Ig1 of LILRB2

<400> SEQUENCE: 18

His Thr Gly Arg Tyr Gly Cys Gln Tyr
1               5

<210> SEQ ID NO 19
<211> LENGTH: 7
<212> TYPE: PRT
<213> ORGANISM: Artificial Sequence
<220> FEATURE:
<223> OTHER INFORMATION: H*G*Y*C motif in Ig4 of LILRB2

<400> SEQUENCE: 19

His Ala Gly Thr Tyr Arg Cys
1               5

<210> SEQ ID NO 20
<211> LENGTH: 9
<212> TYPE: PRT
<213> ORGANISM: Artificial Sequence
<220> FEATURE:
<223> OTHER INFORMATION: Mut-8aa H*G*Y*C motif in Ig1 of LILRB2

<400> SEQUENCE: 20

Ser Ala Asp Glu Ala Arg Cys Arg Gly
1               5
```

LILRB2 AND NOTCH-MEDIATED EXPANSION OF HEMATOPOIETIC PRECURSOR CELLS

This application is a U.S. National Phase based on PCT/US2015/031959, filed on May 21, 2015, which claims the benefit of U.S. provisional application No. 62/002,101, filed on May 22, 2014, and U.S. provisional application No. 62/005,746, filed on May 30, 2014, all of which are incorporated herein by reference in their entirety.

A computer readable textfile, entitled "DN1L51019.txt (SequenceListing.txt)" created on May 21, 2015 and having a size of 80,894 bytes, contains the sequence listing for this application and is hereby incorporated by reference in its entirety.

FIELD OF THE DISCLOSURE

The current disclosure describes methods of expanding precursor cells for hematopoietic transplantation in subjects. The methods culture precursor cells in media containing an immobilized high molecular weight LILRB2 agonist or an LILRB2 agonist in combination with a Notch agonist. The expanded cells can be used to treat a variety of hematopoietic disorders.

BACKGROUND OF THE DISCLOSURE

Hematopoietic stem cells (HSC) are pluripotent and ultimately gives rise to all types of terminally differentiated blood cells. HSC can self-renew or differentiate into more committed hematopoietic progenitor cells (HPC), which progenitor cells are irreversibly determined to be ancestors of only a few types of blood cell. For instance, HSC can differentiate into (i) myeloid progenitor cells, which myeloid progenitor cells ultimately give rise to monocytes and macrophages, neutrophils, basophils, eosinophils, erythrocytes, megakaryocytes/platelets, dendritic cells, or (ii) lymphoid progenitor cells, which lymphoid progenitor cells ultimately give rise to T-cells, B-cells, and lymphocyte-like cells called natural killer cells (NK-cells). Once the HSC differentiate into a myeloid progenitor cell, its progeny cannot give rise to cells of the lymphoid lineage, and, lymphoid cells cannot give rise to cells of the myeloid lineage. For a general discussion of hematopoiesis and HSC differentiation, see Chapter 17, Differentiated Cells and the Maintenance of Tissues, Alberts et al., 1989, Molecular Biology of the Cell, 2nd Ed., Garland Publishing, New York, N.Y.; Chapter 2 of Regenerative Medicine, Department of Health and Human Services, Aug. 5, 2006, and Chapter 5 of Hematopoietic Stem Cells, 2009, Stem Cell Information, Department of Health and Human Services. Precursor cells can include HSC, HPC and/or mixtures of HSC and HPC.

Precursor cell transplantation represents an important therapy due to these cell's capacity to restore blood and immune cells in transplant recipients. For example, transplantation of precursor cells can be used to treat subjects with inherited immuno-deficient or autoimmune diseases and diverse hematopoietic disorders. Precursor cell transplantation can also be used to treat chemotherapy and radiation-treatment patients because prolonged neutropenia and pancytopenia is common following these treatment regimens. As one example, and of particular concern, chemotherapeutic treatments for AML result in prolonged periods of profound neutropenia with infectious complications still common even in the setting of modern antimicrobial therapies with mortality rates as high as 20% in adolescent and young adults. Human bone marrow transplantation methods are also currently used as therapies for leukemia, lymphoma, and other life-threatening diseases.

In transplantation, it has been observed that patients receiving greater numbers of expanded precursor cells have more rapid recovery of their neutrophils following transplantation. Accordingly, high doses of precursor cells are needed to achieve rapid and sustained engraftment that is critical for a patient's survival and recovery. These findings suggest a critical need for generating greater numbers of precursor cells that reliably enhance neutrophil recovery.

Although progress toward efficient ex vivo expansion of precursor cells has been made, significant improvements in the efficacy and reproducibility of this technology are needed before it can be widely used. Accordingly, new approaches are needed.

SUMMARY OF THE DISCLOSURE

Described herein are methods of expanding precursor cells ex vivo, comprising culturing said precursor cells with a LILRB2 agonist immobilized on a first solid phase, wherein the immobilized LILRB2 agonist is (i) an antibody to the LILRB2 receptor, or (ii) an antigen-binding fragment of said antibody; and wherein the precursor cells are hematopoietic stem cells or hematopoietic progenitor cells. In certain embodiments, the methods described herein comprise culturing said precursor cells with an immobilized LILRB2 agonist in combination with a Notch agonist. In specific embodiments, the precursor cells are human cells. In more specific embodiments, the precursor cells are obtained from bone marrow, umbilical cord blood, placental blood, or Wharton's jelly. In more specific embodiments, the precursor cells are obtained from fetal or neonatal blood.

In certain embodiments, the antibody to the LILRB2 receptor is a monoclonal antibody. In certain embodiments, the antibody to the LILRB2 receptor is a polyclonal antibody. In certain embodiments, the LILRB2 agonist is an Fv, Fab, Fab', F(ab')2, Fc, or single chain Fv fragment (scFv). In certain embodiments, the antibody to LILRB2 is a human, humanized, synthetic, or chimeric antibody. In specific embodiments, the LILRB2 agonist binds to the Ig1 domain of LILRB2. In specific embodiments, the LILRB2 agonist binds to the Ig4 domain of LILRB2. In specific embodiments, the LILRB2 agonist binds to the Ig1 and Ig4 domains of LILRB2.

In certain embodiments, the first solid phase is the surface of a tissue culture dish. In certain embodiments, the Notch agonist is immobilized on the first solid phase. In certain embodiments, the Notch agonist is immobilized on a second solid phase that is not the first solid phase. In certain embodiments, the Notch agonist is immobilized on the first solid phase, and the first solid phase is the surface of a tissue culture dish. In certain embodiments, the Notch agonist is immobilized on a second solid phase that is not the first solid phase, wherein the first solid phase is the surface of a tissue culture dish or flask, and the second solid phase is a bead. In certain embodiments, the Notch agonist is immobilized on a second solid phase that is not the first solid phase, wherein the first solid phase is a bead, and the second solid phase is the surface of a tissue culture dish or flask.

In certain embodiments, the Notch agonist is an extracellular, Notch-interacting domain of a Delta protein. In specific embodiments, the Notch agonist is human Delta-1. In specific embodiments, the Notch agonist is Delta$^{ext-IgG}$. In more specific embodiments, the Notch agonist is in dimeric form. In specific embodiments, the Notch agonist is an antibody that specifically binds to a Notch motif. In more specific embodiments, the Notch agonist is an antibody that specifically binds to Notch-1. In specific embodiments, the Notch agonist is an antibody that specifically binds to Notch-2.

In certain embodiments, the culturing step is performed in the presence of a culture medium comprising stem cell factor (SCF), thrombopoietin (TPO), and Flt3-ligand. In specific embodiments, the culturing step is performed in the presence of a culture medium comprising 10-100 ng/mL SCF, 5-100 ng/mL TPO and 10/100 ng/mL Flt3-ligand. In certain embodiments, the culture medium comprises 50 ng/mL SCF. In certain embodiments, the culture medium comprises 10 ng/mL TPO. In certain embodiments, the culture medium comprises 50 ng/mL Flt3-ligand. In certain embodiments, the culture medium comprises 50 ng/mL SCF, 10 ng/mL TPO and 50 ng/mL Flt3-ligand.

In certain embodiments, the culturing step is performed in the presence of a culture medium comprising SCF, Flt3-ligand, interleukin-6 (IL-6), TPO, fibroblast growth factor-1 (FGF1), and interleukin-3 (IL-3). In specific embodiments, the culture medium comprises SCF, Flt3-ligand, IL-6, TPO, FGF1, IL-3, and heparin. In certain embodiments, the culture medium comprises 1-100 ng/mL SCF, 1-100 ng/mL Flt3-ligand, 1-100 ng/mL IL-6, 1-100 ng/mL TPO, 1-100 ng/mL FGF1, and 1-100 ng/mL IL-3. In specific embodiments, the culture medium further comprises 1-100 µg/mL heparin. In certain embodiments, the culture medium comprises 50 ng/mL SCF, 50 ng/mL Flt3-ligand, 50 ng/mL IL-6, 50 ng/mL TPO, 20 ng/mL FGF1, and 10 ng/mL IL-3. In specific embodiments, the culture medium further comprises 10 µg/mL heparin.

In certain embodiments, the culturing step is performed in the presence of a culture medium comprising retronectin. In specific embodiments, the culture medium comprises 1-100 µg/mL retronectin. In more specific embodiments, the culture medium comprises 5 µg/mL retronectin.

The current disclosure provides improved methods to generate precursor cells through ex vivo expansion. The methods generate more precursor cells more quickly than previously-available methods and the generated precursor cells show enhanced early marrow repopulation in immunodeficient subjects and improved long term repopulation following transplant. The methods disclosed herein are based on culturing precursor cells with an immobilized LILRB2 agonist or an LILRB2 agonist in combination with a Notch agonist.

BRIEF DESCRIPTION OF THE FIGURES

(FIG. 1A) Schematic of the chimeric LILRB2 receptor reporter system. (FIG. 1B) Representative flow cytometric profiles and summary showing that the Angptl2 conditioned medium stimulates GFP induction in the LILRB2 chimeric reporter system. The condition media of empty vector-transfected HEK-293T cells was used as control. (FIG. 1C) Left, secreted Angplt2 and HLA-G-ECD in condition medium detected by anti-FLAG antibody in Western blotting. Right, representative flow cytometric plots showing that Angptl2 binds to LILRB2 expressed on HEK-293T cells better than the same amount of HLA-G-ECD. (FIG. 1D) The full-length (FL), coil-coil domain (CC), and fibrinogen domain (FBN) obtained from conditioned medium showed distinctive migration in reducing and non-reducing SDS-PAGE as determined by immunoblotting with anti-M2 Flag antibody. Protein extracted from equivalent amounts of condition media of empty vector-transfected HEK293T cells was used as control. (FIG. 1E) GST-human Angptl2 purified from bacterial expression system by Glutathione Sepharose was immediately fractionated through gel filtration FPLC. The molecular weight was determined by the peaks of Apoferritin (443 KD), Amylase (200 KD), Alcohol dehydrogenase (150 KD), Albumin (66 KD), Carbonic anhydrase (29 KD), and Cytochrome c (12.4 KD), respectively. (FIG. 1F) Equivalent amounts of indicated fractionated samples in FPLC were loaded on 10% native gel. Aggregated, monomeric, and cleaved GST-Angptl2 were visualized by silver staining. (FIG. 1G) Indicated FPLC fractionated samples were examined by Western blotting using antiM2 Flag antibody. The FLAG in cleaved GST-Angptl2 fragments (fraction 8; FIG. 1G) could not be detected by Western blotting. (FIG. 1H) Chimeric LILRB2 receptor reporter cells were treated with coated or soluble fraction 5 proteins for 48 hrs. In coated wells, 5 µg/ml GST-Angptl2 from fraction-5 was pre-coated onto wells of a 96-well plate for 3 hrs at 37° C. Equivalent amount of FPLC buffer was used as control. n.s. indicates not significant; ****, p<0.0001.

(FIG. 2A) Constructs for secretable Angptl2, Angpt15, and HLA-G-ECD. Angptls without signal peptide (SP) or HLA-G ECD was fused to an optimized signal peptide (MWWRLWWLLLLLLLLWPMVWA (SEQ ID NO: 1)) at the N terminus and a FLAG tag at the C terminus. (FIG. 2B) FACS plots showing the binding of Angptl5 to LILRB2 expressing 293T cells.

(FIG. 5A) Representative flow cytometric profiles showing that the GFP induction by immobilized 5 µg/ml Angptl2 was abolished by 5 µg/ml anti-LILRB2 antibody. Chimeric LILRB2 receptor reporter cells were treated with indicated coated Angptl2 with or without soluble anti-LILRB2 pAb or mAb for 48 hrs. PBS was used as control. (FIG. 5B) Representative flow cytometric profiles showing that GFP was induced by immobilized anti-LILRB2 antibodies. Chimeric LILRB2 receptor reporter cells were treated with indicated coated (25 µg/ml in 50 µl PBS) or soluble (5 µg/ml in 250 µl cell culture media) antibodies for 48 hrs. The reporter cells not containing chimeric LILRB2 receptor were used as negative control. (FIG. 5C) Representative flow cytometric profiles showing that GFP expression was induced by cross-linked anti-LILRB2 antibodies. Chimeric LILRB2 receptor reporter cells were treated with 10 µg/ml soluble anti-LILRB2 polyclone antibody (pAb) or equivalent crosslinked pAb for 48 hrs. Streptavidin alone was used as a negative control. (FIG. 5D) Representative confocal images of LILRB2 chimeric receptor reporter cells with or without coated anti-LILRB2 mAb showing that the distribution of LILRB2 protein on cell plasma membrane. Ten confocal scans from top to bottom of a cell were indicated from Layer-1 (L1) to Layer-10 (L10). Confocal images of the phase contrast, Cy3 (indicating LILRB2 expression), and GFP (indicating signaling activation) panels were merged.

(FIG. 6A) Representative flow cytometry plots showing Angptl2 binding to full-length, individual Ig domain, Ig1+2, or Ig3+4 of LILRB2 that were expressed on 293T cells. n=3. (FIG. 6B) Summary of data from FIG. 6A (FIG. 6C) Summary of Angptl2 binding abilities of WT and mutant LILRB2. Indicated mutations are described in FIG. 4B. (FIG. 6C) Schematic of the H*G*Y*C motifs in Ig1 (SEQ ID NO: 18) and Ig4 (SEQ ID NO: 19) of LILRB2. (FIG. 6D) Summary of Angptl2 binding abilities of WT and mutant Ig1+2 LILRB2. (FIG. 6E) Representative flow cytometry plots showing Angptl2 binding to Ig1+2 and mutant LILRB2. (FIG. 6F) Representative flow cytometry plots showing Angptl2 binding to WT and mutant LILRB2. (FIG. 6G) Comparison of Angptl2, Angptl5, and HLA-G binding abilities of WT and mutant LILRB2. MHC-S indicates HLA-G binding sites; MHC-S1, R59A/Y61A; MHC-S2, W90A/D200A/N202A/Y205A; MHC-S1+2, R59A/Y61A/W90A/D200A/N202A/Y205A. (FIG. 6H) Summary of Angptl2-induced activation of the chimeric receptor reporter system by individual Ig domains, Ig1+2, or Ig3+4 of LILRB2. Indicated reporter cells were treated with 5 µg/ml coated GST-Angptl2 or polyclonal or monoclonal anti-LILRB2 antibodies. At least three independent experiments gave the similar results. (FIG. 6I) Summary of Angptl2-induced activation of the chimeric receptor reporter system by WT or mutant LILRB2. Reporter cells were treated with 10 µg/ml coated GST-Angptl2 or polyclonal or monoclonal anti-LILRB2 antibodies. At least three independent experiments were performed that gave similar results.

FIGS. 8A-8C. Mutated residues of LILRB2 in the possible ligand binding interface based on the known structure of LILRB2 (SEQ ID NO: 2). Based on the PDB structure of Ig1-Ig2 domain (PDBID: 2GW5 and 2DYP) (surrounded by solid box in FIG. 8A) and Ig3-Ig4 domain (PDBID: 4LLA) (surrounded by dashed box in FIG. 8A) of human LILRB2, twenty-four large and hydrophobic residues in the possible ligand binding interface on each Ig domain were identified for mutagenesis study (underlined in FIG. 8A) and generated a series of mutant LILRB2 were generated (FIG. 8B). (FIG. 8C) Summary of Angptl2 binding abilities of WT and mutant LILRB2.

(FIG. 11A) Human CD133+ umbilical CB cells were cultured in STF medium with or without same amounts of coated (25 µg/ml in 50 µl PBS) or soluble (5 µg/ml in 250 µl StemSpan media) anti-LILRB2 pAb. Total cell expansion was assessed after 10 days of culture (n=3). (FIG. 11B) Human CD133+ umbilical CB cells were cultured in STF medium with or without same amounts of coated (25 µg/ml in 50 µl PBS) or soluble (5 µg/ml in 250 µl StemSpan media) anti-LILRB2 mAb. Total cell expansion was assessed after 10 days of culture (n=3). (FIG. 11C) Representative flow cytometric profiles showing the frequency of CD34+CD90+ cells after 10 days of culture. (FIGS. 11D-11E) Expansion of 250 input equivalent human CB CD133+ cells treated with or without anti-LILRB2 pAb (FIG. 11D) or mAb (FIG. 11E) were serially plated in CFU medium. Total CFUs were counted after 7 days in culture. n.s., not significant; *, $p<0.05$; *** $p<0.001$.

(FIG. 12A) After 10 days of culture in STF medium with or without same amounts of coated (25 µg/ml in 50 µl PBS) or soluble (5 µg/ml in 250 µl StemSpan media) anti-LILRB2 pAb, expansion of $1\times10^4$ input equivalent human CB CD133+ cells were transplanted into NSG mice (n=8). Engraftment of human cells (human CD45+) in peripheral blood at indicated weeks are shown. n.s., not significant; ***, $p<0.001$. (FIG. 12B) Engraftment of human CD45/CD71+ in bone marrow of mice described in FIG. 12A at 36 weeks. n.s., not significant; *, $p<0.05$; n=8. (FIG. 12C) Multilineage contribution of cultured human umbilical CB CD133+ cells. Shown are representative flow cytometric profiles of bone marrow cells from one primary transplanted mouse of each group. Myeloid, CD45/CD71+ CD15/CD66b+; lymphoid, CD19/CD20+; hematopoietic stem/progenitor cells, CD19/CD20-CD34+. (FIGS. 12D-12F) Summary of multilineage contributions from data shown in FIG. 12C. n.s., not significant; *, $p<0.05$; , $p<0.01$; n=8. (FIG. 12G) Engraftment of human CD45+ cells in peripheral blood of secondarily transplanted mice at 3 and 7 weeks post-transplant are shown. n.s., not significant; , $p<0.01$; n=3. (FIG. 12H) Engraftments of human cells in bone marrow of secondarily transplanted mice at 8 weeks post-transplant are shown. n.s., not significant; *, $p<0.05$; n=3. (FIG. 12I) Representative flow cytometric profiles showing multilineage contribution of human umbilical CB CD133+ cells in the bone marrow of secondarily transplanted mice at 8 weeks post-transplant. (FIGS. 12J-12L) Summary of multilineage contributions from data shown in FIG. 12I. n.s., not significant; *, $p<0.05$; n=3.

(FIG. 13A) After 10 days culture in STF medium with or without coated or soluble anti-LILRB2 polyclonal antibody, $1\times10^4$ input equivalent human CB CD34+ cells were transplanted into NSG mice. Engraftments of human CD45/CD71+ cells in bone marrow at 8 weeks are shown. n.s., not significant; *, $p<0.05$; n=8.

(FIGS. 13B-13D) Multilineage contribution of cultured human umbilical CB CD34+ cells. n.s., not significant; *, p<0.05; **, p<0.01; n=8.

(FIG. 14A) After 10 days culture in STF medium with or without same amounts of coated (25 µg/ml in 250 µl PBS) or soluble (5 µg/ml in 250 µl StemSpan media) anti-LILRB2 mAb, $1\times10^4$ input equivalent human CB CD133+ cells were transplanted into NSG mice. Engraftment of human CD45+ in peripheral blood at 3 and 7 weeks are shown. n.s., not significant; *, p<0.05; n=4. (FIG. 14B) Engraftments of human CD45/CD71+ in bone marrow of mice described in FIG. 14A at 8 weeks. n.s., not significant; n=4. (FIG. 14C) Multilineage contribution of cultured human umbilical CB CD133+ cells. Shown are representative flow cytometric profiles of bone marrow cells from one primary transplanted mouse of each group. (FIGS. 14D-14F) Summary of multilineage contributions based on data shown in FIG. 14C. n.s., not significant; n=4. (FIG. 14G) Engraftment of human CD45+ cells in peripheral blood of secondarily transplanted mice at 3, 7, 10, and 30 weeks. n.s., not significant; *, p<0.05; n=3. (FIG. 14H) Engraftment of human cells in bone marrow of secondarily transplanted mice at 30 weeks. n.s., not significant; n=3. (FIG. 14I) Representative flow cytometric profiles showing multilineage contribution of human umbilical CB CD133+ cells in the bone marrow of secondarily transplanted mice at 8 weeks post-transplant. (FIGS. 14J-14L) Summary of multilineage contributions based on data from FIG. 14I. n.s., not significant; *, p<0.05; n=3.

FIGS. 15A-15I. Net ex vivo expansion of cultured human umbilical CB CD133+ cells as determined by limiting dilution analysis. (FIGS. 15A-15B) Numbers of total nucleated cells (FIG. 15A) and CD34+ cells (FIG. 15B) before and after culture with 25 µg/ml coated anti-LILRB2 pAB. (FIGS. 15C-15D) Percentages of donor human CD45+ cells (FIG. 15C) in the peripheral blood at 1 and 2 months and (FIG. 15D) in bone marrow in recipient NSG mice transplanted with uncultured or expanded cells. (FIG. 15E) Net expansion of HSCs as determined by limiting dilution analysis. The numbers of input equivalent cells were used in the calculation. (FIGS. 15F-15I) Comparisons of multilineage repopulation of HSCs before and after ex vivo expansion. n.s., not significant; *, p<0.05; **, p<0.01; n=8.

The y-axis presents the data as the fold increase in HES1 expression over the value obtained for wells coated with retronectin and human IgG.

Figure 29:
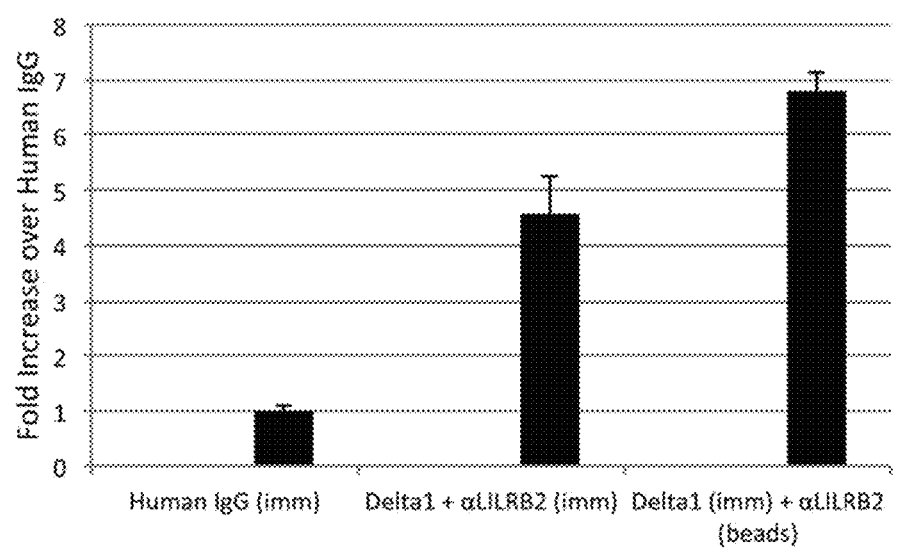

FIG. 29. Cord blood CD34+ cells were cultured for 4 hrs in non-tissue culture wells coated with retronectin and also coated with either i) IgG (human), ii) a combination of anti-LILRB2 antibody (αLILRB2) and Delta1, or (iii) Delta1, in combination with anti-LILRB2 presented on microbeads. HES1 expression was assessed by qPCR and normalized to expression of the β-glucuronidase (GUSB) reference gene. The y-axis presents the data as the fold increase in HES1 expression over the value obtained for wells coated with retronectin and human IgG.

DETAILED DESCRIPTION

Hematopoietic precursor cell transplantation represents an important therapy due to these cell's capacity to restore blood and immune cells in transplant recipients. For example, transplantation of precursor cells can be used to treat subj ects with inherited immunodeficient or autoimmune diseases and diverse hematopoietic disorders. Precursor cell transplantation can also be used to treat chemotherapy and radiation-treatment patients because prolonged neutropenia and pancytopenia is common following these treatment regimens. As one example, and of particular concern, chemotherapeutic treatments for AML, result in prolonged periods of profound neutropenia with infectious complications still common even in the setting of modern antimicrobial therapies with mortality rates as high as 20% in adolescent and young adults. Human bone marrow transplantation methods are also currently used as therapies for leukemia, lymphoma, and other life-threatening diseases.

Delayed myeloid engraftment is a known risk factor for cord blood (CB) transplant (CBT) recipients and is associated with low total nucleated cell count (TNC) and CD34+ cell doses provided in a single or double CB graft. The majority of non-relapse mortality in these patients occurs within the first 100 days post-transplant with infection being the most common cause of death.

In transplantation, high doses of precursor cells are needed to achieve rapid and sustained engraftment that is critical for the patient's survival and recovery; this is especially true when CB precursor cells are used. Although progress toward efficient ex vivo expansion of precursor cells has been made, significant improvements in the efficacy and reproducibility of this technology are needed before it can be widely used.

The present disclosure provides methods for producing immortalized cell populations of non-terminally differentiated precursor cells. In particular, the present disclosure provides methods of growing precursor cells in culture for a period beyond which the cells would otherwise stop proliferating and/or die, due to senescence and/or undergoing crisis leading to cell death.

The current disclosure provides improved methods to expand precursor cells through ex vivo expansion. The methods generate more precursor cells more quickly than previously-available methods and the generated precursor cells show enhanced early marrow repopulation in immune-deficient subjects and improved long term repopulation following transplant. The methods disclosed herein are based on culturing precursor cells with an immobilized LILRB2 agonist or an LILRB2 agonist in combination with a Notch agonist.

Preferably, the technique used for expansion is one that has been shown to result in an increase in the number of precursor cells such as HSC e.g., CD34+ cells, in the expanded sample relative to the unexpanded HSC sample. In certain embodiments, the methods result in a 50-, 75-, 100-150-, 200-, 250-, 300-, 350-, 400-, 450-, 500-, 1000, 2000-, 3000-, 4000-, 5000-fold (or more than) increase in the number of HSC in the expanded sample, relative to the unexpanded sample. The HSC can be positive for one or more of CD34, CD43, CD45RO, CD45RA, CD59, CD90, CD109, CD117, CD133, CD166, and HLA DR and/or negative for Lin and/or CD38. In a specific embodiment, the enhanced engraftment can be detected by detecting an increased percentage of human CD45+ cells in the bone marrow of mice infused with an aliquot of the expanded sample relative to mice infused with an aliquot of the unexpanded sample at, e.g., 10 days, 3 weeks or 9 weeks post-infusion (see Delaney et al., 2010, Nature Med. 16(2): 232-236). In some embodiments, the methods result in a 50-, 75-, 100-, 150-, 200-, 250-, 300-, 350-, 400-, 450-, 500, 1000-, 2000-, 3000-, 4000-, 5000-fold (or more than) increase in the number of CD34+ HSC in the expanded sample, relative to the unexpanded sample. Cell populations are also preferably expanded until a sufficient number of cells are obtained to provide for at least one infusion into a human subject.

1.1 LILRB2 and Notch Agonists

The present disclosure contemplates use of an immobilized LILRB2 agonist and/or an LILRB2 agonist in combination with a Notch agonist to expand precursor cells. An agonist is an agent that promotes, i.e., causes or increases, activation of LILRB2 and/or Notch pathway function. "LILRB2 pathway function" means a function mediated by the LILRB2 signaling (signal transduction) pathway, including inhibition mediated by immunoreceptor tyrosine-based inhibitory motifs (ITIMs) and/or recruitment of phosphatases SHP-1, SHP-2, or SHIP. "Notch pathway function" means a function mediated by the Notch signaling (signal transduction) pathway, including but not limited to nuclear translocation of the intracellular domain of Notch, nuclear translocation of RBP-JK or its *Drosophila* homolog Suppressor of Hairless; activation of bHLH genes of the Enhancer of Split complex, e.g., Mastermind; activation of the HES-1 gene or the KBF2 (also called CBF1) gene; inhibition of *Drosophila* neuroblast segregation; and binding of Notch to a Delta protein, a Jagged/Serrate protein, Fringe, Deltex or RBP-JKI Suppressor of Hairless, or homologs or analogs thereof. See generally the review article by Kopan et al., 2009, Cell 137:216-233 for a discussion of the Notch signal transduction pathway and its effects upon activation; see also Jarriault et al., 1998, Mol. Cell. Biol. 18:7423-7431.

Pathway activation is carried out by exposing a cell to one or more agonists. The agonists can be but are not limited to soluble molecules, molecules that are recombinantly expressed on a cell-surface, molecules on a cell monolayer to which the precursor cells are exposed, or molecules immobilized on a solid phase.

Agonists of the present disclosure include but are not limited to proteins and analogs and derivatives (including fragments) thereof; proteins that are other elements of the LILRB2 or Notch pathway and analogs and derivatives (including fragments) thereof activating antibodies thereto and fragments or other derivatives of such antibodies containing the binding region thereof; nucleic acids encoding the proteins and derivatives or analogs; as well as proteins and derivatives and analogs thereof which bind to or otherwise interact with LILRB2 or Notch proteins or other proteins in the LILRB2 or Notch pathways such that LILRB2 pathway activity or Notch pathway activity is promoted. Such agonists include but are not limited to proteins and derivatives thereof comprising relevant intracellular domains, nucleic acids encoding the foregoing, and proteins comprising the interacting domain of LILRB2 or Notch ligands. These proteins, fragments and derivatives thereof can be recombinantly expressed and isolated or can be chemically synthesized.

Antibodies for use with the methods disclosed herein can include whole antibodies or binding fragments of an antibody, e.g., Fv, Fab, Fab', F(ab')2, Fc, and single chain Fv fragments (ScFv) or any biologically effective fragments of an immunoglobulin that bind specifically to a LILRB2 or Notch motif.

Antibodies or antigen binding fragments include all or a portion of polyclonal antibodies, monoclonal antibodies, human antibodies, humanized antibodies, synthetic antibodies, chimeric antibodies, bispecific antibodies, mini bodies, and linear antibodies.

Antibodies from human origin or humanized antibodies have lowered or no immunogenicity in humans and have a lower number of non-immunogenic epitopes compared to non-human antibodies. Antibodies and their fragments will generally be selected to have a reduced level or no antigenicity in human subjects.

Antibodies that specifically bind an LILRB2 or Notch motif can be prepared using methods of obtaining monoclonal or polyclonal antibodies, methods of phage display, methods to generate human or humanized antibodies, or methods using a transgenic animal or plant engineered to produce antibodies as is known to those of ordinary skill in the art (see, for example, U.S. Pat. Nos. 6,291,161 and 6,291,158). Phage display libraries of partially or fully synthetic antibodies are available and can be screened for an antibody or fragment thereof that can bind to an LILRB2 or Notch motif. For example, binding domains may be identified by screening a Fab phage library for Fab fragments that specifically bind to a target of interest (see Hoet et al., Nat. Biotechnol. 23:344, 2005). Phage display libraries of human antibodies are also available. Additionally, traditional strategies for hybridoma development using a target of interest as an immunogen in convenient systems (e.g., mice, HuMAb Mouse®, TC Mouse™, KM-mouse®, llamas, chicken, rats, hamsters, rabbits, etc.) can be used to develop binding domains. In particular embodiments, antibodies specifically bind an LILRB2 or Notch motif and do not cross react with nonspecific components or unrelated targets. Once identified, the amino acid sequence or polynucleotide sequence coding for the antibody can be isolated and/or determined.

In another specific embodiment, the agonist is a cell which recombinantly expresses a protein or fragment or derivative thereof, which agonizes LILRB2 or Notch. The cell expresses the agonist in such a manner that it is made available to precursor cells in which LILRB2 or Notch signal transduction is to be activated, e.g., it is secreted, expressed on the cell surface, etc.

In yet another specific embodiment, the agonist is a peptidomimetic or peptide analog or organic molecule that binds to a member of the LILRB2 or Notch signaling pathway. Such an agonist can be identified by the chimeric LILRB2 receptor reporter system described herein and/or by binding assays selected from those known in the art, for example the cell aggregation assays described in Rebay et al., 1991, Cell 67:687-699 and in International Patent Publication No. WO 92119734.

In a preferred embodiment the agonist is a protein including at least a fragment of a protein encoded by an LILRB2- or Notch-interacting gene which mediates binding to a protein or a fragment of LILRB2 or Notch, which fragment contains the region responsible for binding to the agonist protein.

In some embodiments, the agonist is recombinantly expressed from a nucleic acid introduced into the precursor cells. In specific embodiments, the recombinantly expressed agonist is a chimeric protein which includes an intracellular domain of a receptor and an extracellular domain of another ligand-binding surface receptor. In such embodiments, the LILRB2 or Notch pathway can be activated by exposure to a ligand of such another ligand-binding surface receptor. The recombinantly expressed agonist can be expressed by precursor cells from an inducible promoter. In certain embodiments, the expression of the nucleic acid encoding the agonist is under the control of Cre/Lox system or FLP/FRT system. In one embodiment, the agonist is flanked by Cre sites.

In a specific embodiment, exposure of the cells to an agonist is not done by incubation with other cells recombinantly expressing a LILRB2 or Notch ligand on the cell surface (although in other embodiments, this method can be used), but rather is by exposure to a cell-free ligand, e.g., incubation with a cell-free ligand of LILRB2 or Notch, which ligand is immobilized on the surface of a solid phase, e.g., immobilized on the surface of a tissue culture dish.

In some embodiments, cells are expanded by culturing the cells with an LILRB2 agonist immobilized on a first solid phase and a Notch agonist immobilized on a second solid phase, wherein the first and second solid phases are the same.

In some embodiments, cells are expanded by culturing the cells with an LILRB2 agonist immobilized on a first solid phase and a Notch agonist immobilized on a second solid phase, wherein the second solid phase is not the first solid phase. In a specific embodiment, the first and second solid phases are different types of solid phases, selected from among any known in the art, including, but not limited to a culture dish, a culture flask, a culture plate, a bead, a particle, etc. In specific embodiments, the first solid phase is a surface of a tissue culture dish or flask, and the second solid phase is a bead, e.g. a magnetic microbead. In other specific embodiments, the first solid phase is a bead, e.g. a magnetic microbead, and the second solid phase is a surface of a tissue culture dish or flask. In an embodiment where the LILRB2 agonist and Notch agonist are immobilized on different solid phases, the precursor cells can be cultured with the LILRB2 agonist and the Notch agonist concurrently or sequentially.

1.2 LILRB2 Agonists

The methods disclosed herein include LILRB2 agonists. In particular embodiments, angiopoietins and angiopoietin-like proteins (Angptls) represent exemplary LILRB2 agonists. Until recently, Angptls were considered "orphan ligands" as no receptors were known. In 2012, a subset of the current inventors identified human leukocyte immunoglobulin-like receptor B2 (LILRB2) and its mouse ortholog paired Ig-like receptor (PirB) as receptors for several Angptls. Zheng et al., Nature. 2012; 485:656-660. It was also found that LILRB2 and PirB are expressed by human and mouse HSCs, respectively, and support their ex vivo expansion. Zheng et al., Nature. 2012; 485:656-660. LILRB2 sequence information includes: Accession: NP_001265335.2 (SEQ ID NO: 3); Accession:

NP_001265334.2 (SEQ ID NO: 4); Accession: NP_001265333.2 (SEQ ID NO: 5); Accession: NP_001265332.2 (SEQ ID NO: 6); and Accession: AAH36827.1 (SEQ ID NO: 7).

Several Angptls support the activity of precursor cells, such as HSCs in vitro and in vivo. For example, several Angptls inhibit differentiation and promote repopulation of HSCs in vitro and in vivo. Zheng et al., Cell Stem Cell. 2011; 9:119-130; Zheng et al., Blood. 2011; 117:470-479; Zhang and Lodish Curr Opin Hematol. 2008; 15:307-311; and Zhang et al., Blood. 2008; 111:3415-3423. LILRB2 and PirB are also required for leukemia development as they inhibit differentiation and promote self-renewal of leukemic progenitors. Zheng et al., Nature. 2012; 485:656-660. It was further demonstrated that the binding of Angptls to LILRB2/PirB induces activation of SHP-2 and CAMKs, both types of factors known to be critical for supporting the activity of HSCs Kitsos et al., J Biol Chem. 2005; 280:33101-33108; Chan et al., Exp Hematol. 2006; 34:1230-1239.

LILRB2 receptors contain ITIMs in their intracellular domains and are classified as inhibitory receptors because ITIM motifs can recruit phosphatases SHP-1, SHP-2, or SHIP to negatively regulate cell activation. Takai et al., J Biomed Biotechnol. 2011; 2011:275302; Daeron et al., Immunol Rev. 2008; 224:11-43. An important question is how Angptl binding leads to the activation of LILRB2. In Example 1, the molecular basis for the interaction between Angptls and LILRB2 is described. It is shown that mammalian-expressed Angptl2 exists as HMW species, which is needed for activation of LILRB2 and subsequent downstream signaling. A novel motif in the first and fourth Ig domains of LILRB2 that is critical to the Angptl2 binding was also identified. Moreover, that the binding of Angptl2 to LILRB2 is more potent and not completely overlapped with the binding of another ligand HLA-G is shown. Based on the new understanding of the Angptl/LILRB2 interaction, a serum-free culture containing defined cytokines and immobilized antiLILRB2 antibodies that supports a stable and reproducible ex vivo expansion of repopulating human CB precursor cells was developed.

Based on the foregoing, LILRB2 agonists of the current disclosure can particularly include high molecular weight agonists (above 200 kD; above 210 kD; above 215 kD; above 220 kD; above 225 kD; above 230 kD; above 235 kD; above 240 kD; above 245 kD; above 250 kD; above 255 kD; above 260 kD; above 265 kD; above 270 kD; above 275 kD; above 280 kD; above 285 kD; above 290 kD; above 295 kD; or above 300 kD) including high molecular weight Angptls. LILRB2 agonists can also include multimerized LILRB2 agonists, including mulitmerized Angptls.

In particular embodiments, LILRB2 agonists bind a motif in the Ig1 domain of LILRB2, a motif in the Ig2 domain of LILRB2, a motif in the Ig3 domain of LILRB2, and/or a motif in the Ig4 domain of LILRB2. In more particular embodiments, the LILRB2 agonists bind motifs in the Ig1 and Ig4 domains of LILRB2. In more particular embodiments, the LILRB2 agonists bind amino acids at positions 92-100 of the Ig1 domain. In more particular embodiments, the LILRB2 agonists bind amino acids at positions 390-396 of the Ig4 domain. In more particular embodiments, the LILRB2 agonists bind amino acids at positions 92-100 of the Ig1 domain and amino acids at positions 390-396 of the Ig4 domain. In more particular embodiments, the LILRB2 agonists bind amino acids at positions 94, 95 and 96 of the Ig1 domain and amino acids at positions 392 and 394 of the Ig4 domain.

Within the current disclosure, Angptls can be any member of a family of secreted glycosylated proteins that are similar in structure to angiopoietins (Oike et al., Int. J. Hematol. 80:21-8 (2004)). Similar to angiopoietins, Angptls contain an N-terminal CC domain and a C-terminal FBN-like domain. Unlike angiopoietins, Angptls do not bind to the tyrosine kinase receptor Tie2. Angptls include Angptls 2, 3, 4, 5, 6, and 7. Angptls also include microfibrillar-associated glycoprotein 4 (Mfap4), and analogs and equivalents thereof. Angptl2 has been described by Kim, et al. 1999, J Biol Chem 274, 26523-8). In addition, Angptls are available commercially (R&D Systems, Abnova Corp).

Exemplary Angptls are provided, for example in GenBank as Accession Number AAH12368 (human Angptl2 precursor; SEQ ID NO: 8) Accession Number AAH58287 (human Angptl3 precursor; SEQ ID NO: 9) Accession Number AAH23647 (human Angptl4; SEQ ID NO: 10) and Accession Number AAH49170 (human Angptl5; SEQ ID NO: 11). An exemplary sequence for Angptl7 is found in GenBank Accession No. AAH01881 (SEQ ID NO: 12). An exemplary sequence for Mfap4 is found in GenBank Accession No. NP002395 (SEQ ID NO: 13).

Suitable equivalents for Angptls include proteins and polypeptides having similar biological activity to these factors as wild-type or purified Angptls (e.g., recombinantly produced). Suitable analogs of Angptls include fragments retaining the desired activity and related molecules. One preferred analog is a fragment of the Angptl containing the CC domain, for example, the CC domain of Angptl2. Another analog is the FBN-like domain. Fragments of Angptls such as the CC domain and the FBN-like domain may be easier to express and to purify compared to full-length protein. Molecules capable of binding the corresponding Angptl receptor and initiating one or more biological actions associated with Angptl binding to its receptor are also within the scope of the disclosure.

Antibodies to the LILRB2 receptor can also be used. Exemplary commercially available antibodies include, anti-LILRB2 polyclonal antibody (pAb, #BAF2078, R&D systems) and anti-LILRB2 monoclonal antibody (mAb, #16-5149-85, eBioscience).

Exemplary production methods of LILRB2 agonists are described in, for example, U.S. Patent Publication Nos. 2014/0017784 and 2011/0196343.

In certain embodiments, to determine whether an LILRB2 binding protein, e.g., an anti-LILRB2 antibody, is an LILRB2 agonist, precursor cells, e.g., hematopoietic stem cells or hematopoietic progenitor cells, are cultured in the presence of the LILRB2 binding protein and then tested for increased Hes1 expression levels (relative to precursor cells cultured in the presence of a control molecule not having LILRB2 agonist activity), e.g., by q-PCR, wherein increased Hes1 expression levels in the cells cultured in the presence of the LILRB2 binding protein indicates that the LILRB2 binding protein is an LILRB2 agonist. In other embodiments, to determine whether an LILRB2 binding protein, e.g., an anti-LILRB2 antibody, is an LILRB2 agonist, precursor cells, e.g., hematopoietic stem cells or hematopoietic progenitor cells, are cultured in the presence of the LILRB2 binding protein and then injected into NSG mice, wherein increased engraftment of the cells cultured in the presence of the LILRB2 binding protein in NSG mice (relative to precursor cells cultured in the presence of a control molecule not having LILRB2 agonist activity) indicates that the LILRB2 binding protein is an LILRB2 agonist.

1.3 Notch Agonists

The current disclosure also describes stable and reproducible ex vivo expansion of precursor cells using a combination of Angptl agonists and Notch agonists.

Members of the Notch family encode large transmembrane proteins that play central roles in cell-cell interactions and cell-fate decisions during early development in a number of invertebrate systems (Simpson, 1995, Nature 375: 736-7; Artavanis-Tsakonis et al., 1995, Science. 268:225-232; Simpson, 1998, Semin. Cell Dev. Biol. 9:581-2; Go et al., 1998, Development. 125:2031-2040; Artavanis-Tsakonas and Simpson, 1991, Trends Genet. 7:403-408). The Notch receptor is part of a highly conserved pathway that enables a variety of cell types to choose between alternative differentiation pathways based on those taken by immediately neighboring cells. This receptor appears to act through an undefined common step that controls the progression of uncommitted cells toward the differentiated state by inhibiting their competence to adopt one of two alternative fates, thereby allowing the cell either to delay differentiation, or in the presence of the appropriate developmental signal, to commit to differentiate along the non-inhibited pathway.

Genetic and molecular studies have led to the identification of a group of genes which define distinct elements of the Notch signaling pathway. While the identification of these various elements has come from *Drosophila* using genetic tools, initial guide, subsequent analyses have led to the identification of homologous proteins in vertebrate species including humans. The molecular relationships between the known Notch pathway elements as well as their subcellular localization are depicted in Artavanis-Tsakonas et al., 1995, Science 268:225-232; Artavanis-Tsakonas et al., 1999, Science 284:770-776; and in Kopan et al., 2009, Cell 137:216-233. Proteins of the Delta family and proteins of the Serrate (including Jagged, the mammalian homolog of Serrate) family are extracellular ligands of Notch. The portion of Delta and Serrate responsible for binding to Notch is called the DSL domain, which domain is located in the extracellular domain of the protein. Epidermal growth factor-like repeats (ELRs) 11 and 12 in the extracellular domain of Notch are responsible for binding to Delta, Serrate and Jagged. See Artavanis-Tsakonas et al., 1995, Science 268: 225-232 and Kopan et al., 2009, Cell 137:216-233. Exemplary sequences relevant to Notch signaling include Accession Number: P46531.4 (SEQ ID NO: 14); Accession Number: AAG09716.1 (SEQ ID NO: 15); Accession Number: 2KB9_A (SEQ ID NO: 16) and Accession Number: 2VJ2_B (SEQ ID NO: 17).

The present disclosure contemplates use of a Notch agonist. Contemplated for use in the present disclosure are any of the Notch agonists disclosed in U.S. Pat. No. 7,399,633, or any other Notch agonists known in the art.

Notch agonists include but are not limited to Notch proteins and derivatives thereof comprising the intracellular domain, Notch nucleic acids encoding the foregoing, and proteins comprising the Notch-interacting domain of Notch ligands (e.g., the extracellular domain of Delta or Serrate). Other agonists include but are not limited to RBP JKI Suppressor of Hairless or Deltex. Fringe can be used to enhance Notch activity, for example in conjunction with Delta protein. These proteins, fragments and derivatives thereof can be recombinantly expressed and isolated or can be chemically synthesized.

In a preferred embodiment the agonist is a protein including at least a fragment of a protein encoded by a Notch-interacting gene which mediates binding to a Notch protein or a fragment of Notch, which fragment of Notch contains the region of Notch responsible for binding to the agonist protein, e.g., epidermal growth factor-like repeats 11 and 12 of Notch. Notch interacting genes mean the genes Notch, Delta, Serrate, Jagged, RBPJK, Suppressor of Hairless and Deltex, as well as other members of the Delta/Serrate family or Deltex family which may be identified by virtue of sequence homology or genetic interaction and more generally, members of the "Notch cascade" or the "Notch group" of genes, which are identified by molecular interactions (e.g., binding in vitro, or genetic interactions (as depicted phenotypically, e.g., in *Drosophila*). Exemplary fragments of Notch-binding proteins containing the region responsible for binding to Notch are described in U.S. Pat. Nos. 5,648, 464; 5,849,869; and 5,856,441. The Notch agonists utilized by the methods of the disclosure can be obtained commercially, produced by recombinant expression, or chemically synthesized.

In a specific embodiment, the Notch agonist is a dominant active mutant of a Notch protein (e.g., a Notch receptor lacking the extracellular, ligand binding domain). In another embodiment, the Notch agonist is not a dominant active mutant of a Notch protein.

In some embodiments, the Notch agonist is recombinantly expressed from a nucleic acid introduced into the precursor cell. Methods that can be used for recombinantly expressing a Notch agonist are described in sec. 5.3 of U.S. Pat. No. 7,399,633. In particular embodiments, the Notch agonist is a Notch protein (e.g., human or murine Notch-1, Notch-2, Notch-3 or Notch-4) including the intracellular domain of the Notch protein expressed recombinantly in precursor cells. In specific embodiments, the recombinantly expressed Notch agonist is a chimeric Notch protein which includes the intracellular domain of Notch receptor and the extracellular domain of another ligand-binding surface receptor (e.g., the EGF receptor). In such embodiments, the Notch pathway can be activated by exposure to a ligand of such another ligand-binding surface receptor (e.g., EGF). The recombinantly expressed Notch agonist can be expressed by precursor cells from an inducible promoter. In certain embodiments, the expression of the nucleic acid encoding the Notch agonist is under the control of Cre/Lox system or FLP/FRT system. In one embodiment, the Notch agonist is flanked by Cre sites.

In another specific embodiment, and as described in U.S. Pat. No. 5,780,300 to Artavanis-Tsakonas et al., Notch agonists include reagents that promote or activate cellular processes that mediate the maturation or processing steps required for the activation of Notch or a member of the Notch signaling pathway, such as the turin-like convertase required for Notch processing, Kuzbanian, the metalloprotease-disintegrin (ADAM) thought to be required for the activation of the Notch pathway upstream or parallel to Notch (Schlondorfiand Blobel, 1999, J. Cell Sci. 112:3603-3617), or, more generally, cellular trafficking and processing proteins such as the rab family of GTPases required for movement between cellular compartments (for a review on Rab GTPases, see Olkkonen and Stenmark, 1997, Int. Rev. Cytol. 176:1-85). The agonist can be any molecule that increases the activity of one of the above processes, such as a nucleic acid encoding a turin, Kuzbanian or rab protein, or a fragment or derivative or dominant active mutant thereof: or a peptidomimetic or peptide analog or organic molecule that binds to and activates the function of the above proteins.

U.S. Pat. No. 5,780,300 further discloses classes of Notch agonist molecules (and methods of their identification) which can be used to activate the Notch pathway in the practice of the present disclosure, for example molecules that trigger the dissociation of the Notch ankyrin repeats with RBP-JK, thereby promoting the translocation of RBP-JK from the cytoplasm to the nucleus.

Exemplary Notch agonists are the extracellular binding ligands Delta and Serrate (e.g., Jagged) which bind to the extracellular domain of Notch and activate Notch signal transduction, or a fragment (e.g., the extracellular domain) of Delta or Serrate (e.g., Jagged) that binds to the extracellular domain of Notch and activates Notch signal transduction. Nucleic acid and amino acid sequences of Delta family members and Serrate family members (e.g., Jagged family members) have been isolated from several species, including human, are known in the art, and are disclosed in International Patent Publication Nos. WO 93/12141, WO 96/27610, WO 97/01571, Gray et al., 1999, Am. J. Path. 154:785-794. Jagged is a mammalian homologue of Serrate. As used in this application, Serrate shall encompass Jagged unless the context indicates otherwise. In one embodiment, the Notch agonist is Delta$^{extIgG}$, which is a fragment of a Delta protein consisting of the extracellular domain of the protein fused to the Fc portion of IgG.

In certain embodiments, the Notch agonist is an anti-Notch antibody or antigen-binding fragment thereof. In specific embodiments, the Notch agonist is an anti-Notch-1 antibody or antigen-binding fragment thereof. In more specific embodiments, the Notch agonist is the anti-Notch-1 HMN1-519 antibody (commercially available from Biolegend, San Diego, Calif.). In other specific embodiments, the Notch agonist is an anti-Notch-2 antibody or antigen-binding fragment thereof. In more specific embodiments, the Notch agonist is the anti-Notch-2 HMN2-25 antibody (commercially available from Biolegend, San Diego, Calif.). In other specific embodiments, the Notch agonist is a combination of an anti-Notch-1 antibody and an anti-Notch-2 antibody.

Sequence information provided by public databases can be used to identify nucleic acid sequences encoding proteins disclosed herein and vice versa. Variants of the sequences disclosed and referenced herein are also included. Variants of proteins can include those having one or more conservative amino acid substitutions. As used herein, a "conservative substitution" involves a substitution found in one of the following conservative substitutions groups: Group 1: Alanine (Ala or A), Glycine (Gly or G), Serine (Ser or S), Threonine (Thr or T); Group 2: Aspartic acid (Asp or D), Glutamic acid (Glu or Z); Group 3: Asparagine (Asn or N), Glutamine (Gln or Q); Group 4: Arginine (Arg or R), Lysine (Lys or K), Histidine (His or H); Group 5: Isoleucine (Ile or I), Leucine (Leu or L), Methionine (Met or M), Valine (Val or V); and Group 6: Phenylalanine (Phe or F), Tyrosine (Tyr or Y), Tryptophan (Trp or W).

Additionally, amino acids can be grouped into conservative substitution groups by similar function or chemical structure or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cysteine (Cys or C); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company.

Variants of the protein sequences disclosed or referenced herein also include sequences with at least 70% sequence identity, at least 80% sequence identity, at least 85% sequence, at least 90% sequence identity, at least 95% sequence identity, at least 96% sequence identity, at least 97% sequence identity, at least 98% sequence identity, or at least 99% sequence identity to the protein sequences disclosed or referenced herein.

"% sequence identity" refers to a relationship between two or more sequences, as determined by comparing the sequences. In the art, "identity" also means the degree of sequence relatedness between proteins as determined by the match between strings of such sequences. "Identity" (often referred to as "similarity") can be readily calculated by known methods, including (but not limited to) those described in: Computational Molecular Biology (Lesk, A. M., ed.) Oxford University Press, N Y (1988); Biocomputing: Informatics and Genome Projects (Smith, D. W., ed.) Academic Press, N Y (1994); Computer Analysis of Sequence Data, Part I (Griffin, A. M., and Griffin, H. G., eds.) Humana Press, N J (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215:403-410 (1990); DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters which originally load with the software when first initialized.

1.4 Immobilized/Solid Support

In some embodiments, during the culturing step, precursor cells are cultured in the presence of immobilized LILRB2 and/or Notch agonists, in particular embodiments the extracellular domains of an agonist, and in further particular embodiments, fused to a fusion partner. In specific embodiments, during the culturing step, precursor cells are cultured on a solid phase coated with LILRB2 and/or Notch agonists.

In certain embodiments, the isolated precursor cells are expanded in the presence of a fibronectin or a fragment thereof (e.g., CH-296; (Dao et al., 1998, Blood 92(12):4612-21)) or RetroNectin® (a recombinant human fibronectin fragment; Clontech Laboratories, Inc., Madison, Wis.)). In certain embodiments, fibronectin is excluded from the tissue culture dishes or is replaced by another extracellular matrix protein. See also U.S. Pat. No. 7,399,633 to Bernstein et al. for additional exemplary culture conditions for precursor cell expansion. For example, the isolated precursor cells can be expanded in the presence of an immobilized fibronectin or a fragment thereof (e.g., immobilized on the same solid phase as LILRB2 and/or Notch agonist), or immobilized on a solid phase that is different from the solid phase on which the LILRB2 and/or Notch agonist is immobilized.

1.5 Growth Factors & Other Culture Components

In some embodiments, precursor cells are expanded in the presence of one or more growth factors, two or more growth factors, three or more growth factors, or four or more growth factors (e.g., in a fluid medium).

In some embodiments, the amount or concentration of growth factors suitable for expanding precursor cells of the present disclosure is the amount or concentration effective to promote proliferation of HSC but substantially no differentiation of HSC.

Exposing precursor cells to one or more growth factors can be done prior to, concurrently with, or following exposure of the cells to a LILRB2 and/or Notch agonist. In some embodiments, precursor cells are exposed to one or more growth factors for at least a portion of the time or the minimal culture time, most preferably the majority or all of the time, that precursor cells are exposed to a LILRB2 and/or Notch agonist. The minimal culture time is the amount of time at which the cell would die or stop proliferating in the absence of LILRB2 and/or Notch agonist and the growth factors (e.g., 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, or 25 weeks). In specific embodiments, the minimal culture time is from 3 to 4 weeks.

In specific exemplary embodiments, the growth factors present in the expansion medium include one or more of the following growth factors: stem cell factor (SCF; also known as the c-kit ligand or mast cell growth factor), Flt-3 ligand (Flt-3L), interleukin-6 (IL-6), interleukin-3 (IL-3), interleukin-7 (IL-7), interleukin-11 (IL-11), thrombopoietin (TPO), granulocyte-macrophage colony stimulating factor (GM-CSF), granulocyte colony stimulating factor (G-CSF), insulin growth factor-2 (IFG-2), and fibroblast growth factor-1 (FGF-1).

In some embodiments, the growth factors present in the expansion medium include one or more of the following growth factors: IL-1, IL-3, IL-6, IL-11, G-CSF, GM-CSF, SCF, FIT3-L, TPO, erythropoietin and analogs thereof (wherein the analogs include any structural variants of the growth factors having the biological activity of the naturally occurring growth factor and cytokine receptor agonists, e.g., agonist antibody against the TPO receptor such as VB22B sc(Fv)2 described in WO 20071145227) (see page 13 of U.S. Patent Publication No. 2010/0183564). In one embodiment, SCF, Flt3-L and TPO are used in the expansion methods provided herein. In another embodiment, IL-6, SCF, Flt3-L and TPO are used in the expansion methods provided herein. In some embodiments, one or more growth factors are used in a serum-free medium.

The amount or concentration of growth factors suitable for expanding precursor cells of the present disclosure will depend on the activity of the growth factor preparation, and the species correspondence between the growth factors and precursor cells, etc. The amount of growth factors can be in the range of 5-1000 ng/ml. Generally, when the growth factor(s) and precursor cells are of the same species, the total amount of growth factor in the culture medium ranges from 1 ng/ml to 100 μg/ml, more preferably from 5 ng/ml to 1 μg/ml, and most preferably from about 5 ng/ml to 250 ng/ml.

In certain embodiments, the foregoing growth factors are present in the culture condition for expanding precursor cells at the following concentrations: 25-300 ng/ml SCF, 25-300 ng/ml Flt-3 ligand, 25-100 ng/ml TPO, 25-100 ng/ml IL-6 and 10 ng/ml IL-3. In more specific embodiments, 50, 100 or 200 ng/ml SCF, 50, 100 or 200 ng/ml of Flt-3 ligand, 50 or 100 ng/ml TPO, 50 or 100 ng/ml IL-6 and about 10 ng/ml IL-3 can be used.

In one embodiment, precursor cells are expanded by exposing precursor cells to an LILRB2 agonist and 50 ng/ml SCF; 10 ng/ml TPO; and 50 ng/ml FLT3-ligand. In one embodiment, precursor cells are expanded by exposing precursor cells to an LILRB2 agonist and 50 ng/ml SCF; 10 ng/ml TPO; and 50 ng/ml FLT3-ligand in StemSpan media (Stemcell Technologies, Inc.). In another embodiment, precursor cells are expanded by exposing precursor cells to an LILRB2 agonist and 50 ng/ml SCF; 10 ng/ml TPO; and 50 ng/ml FLT3-ligand for 10 days.

In further embodiments, precursor cells are expanded by exposing precursor cells to an LILRB2 agonist, a Notch agonist and 50 ng/ml SCF; 50 ng/ml Flt-3 ligand; 50 ng/ml interleukin-6 (IL-6); 50 ng/ml TPO; 20 ng/ml FGF1; 10 ng/ml interleukin-3 (IL-3); and 10 μg/ml heparin. In one embodiment, precursor cells are expanded by exposing precursor cells to an LILRB2 agonist, a Notch agonist and 50 ng/ml SCF; 50 ng/ml Flt-3 ligand; 50 ng/ml interleukin-6 (IL-6); 50 ng/ml TPO; 20 ng/ml FGF1; 10 ng/ml interleukin-3 (IL-3); and 10 μg/ml heparin in StemSpan media (Stemcell Technologies, Inc.).

Exposing precursor cells to a Notch agonist can be done prior to, concurrently with, or following exposure of the cells to an LILRB2 agonist. In one embodiment, precursor cells are exposed to both an LILRB2 agonist and a Notch agonist for the entire period of ex vivo expansion of precursor cells. In some embodiments, precursor cells are exposed to both an LILRB2 agonist and a Notch agonist for more than 80%, 85%, 90%, 95%, 98%, or 99% of the period of ex vivo expansion of precursor cells. In another embodiment, precursor cells are exposed to an LILRB2 agonist and a Notch agonist for less than the entire period of ex vivo expansion of precursor cells. In yet another embodiment, precursor cells are exposed to an LILRB2 agonist for the entire period of ex vivo expansion of precursor cells, but are exposed to a Notch agonist for less than the entire period of ex vivo expansion (e.g., for less than 100%, 99%, 98%, 95%, 90%, 85%, 80%, 75%, 70%, 60%, or 50% of the ex vivo expansion period). Alternatively, precursor cells are exposed to a Notch agonist for the entire period of ex vivo expansion of precursor cells, but are exposed to an LILRB2 agonist for less than the entire period of ex vivo expansion (e.g., for less than 100%, 99%, 98%, 95%, 90%, 85%, 80%, 75%, 70%, 60%, or 50% of the ex vivo expansion period).

Culturing precursor cells can take place under any suitable culture medium/conditions described in U.S. Patent Publication No. 2004/0067583, U.S. Pat. No. 7,399,633, or U.S. Patent Publication No. 2010/0183564 or as is known in the art (see, e.g., Freshney Culture of Animal Cells, Wiley-Liss, Inc., New York, N.Y. (1994)). The time in culture is a time sufficient to produce an expanded precursor cell population. For example, precursor cells can be cultured in a serum-free medium in the presence of an LILRB2 agonist and/or a Notch agonist, and, optionally, one or more growth factors or cytokines for 2, 3, 4, 5, 6, 7, 8, 9, 10, 11, 12, 13, 14, 15, 16, 17, 18, 19, 20, 21, 22, 23, 24, 25, 26, 27, 28, 29, 30, or 35 days; or, preferably, for at least 10 or at least 15 days or at least 16 days. Optionally, at any point during the culturing period, the culture medium can be replaced with fresh medium or fresh medium can be added. In one embodiment, the fresh culture medium is added every 3 or 4 days.

In other embodiments, precursor cells are cultured for 1 week, 2 weeks, 3 weeks, 4 weeks, 5 weeks, 6 weeks, 7 weeks, 8 weeks, 9 weeks or 10 weeks; or, preferably, the precursor cells are cultured for at least 3 or 4 weeks (in the presence of the combination of an LILRB2 agonist and/or a Notch agonist, and, optionally, one or more growth factors). In yet other embodiments, precursor cells are cultured for less than 4 weeks (in the presence of an LILRB2 agonist and/or a Notch agonist, and, optionally, one or more growth factors). In yet other embodiments, precursor cells are cultured for more than 10 weeks, e.g., 12, 15, 18, 20 or 25 weeks (in the presence of an LILRB2 agonist and/or a Notch agonist, and, optionally, one or more growth factors).

1.6 Source, Collection, Isolation and Treatment of Precursor Cells for Expansion The present disclosure provides methods for immortalizing and optionally differentiating precursor cells, by circumventing or delaying the entry of the precursor cells into cell cycle arrest or into a nonreplicative phase. Precursor cells for immortalization according to the disclosure are non-terminally-differentiated cells and can be from any species, including but not limited to human, animal, plant, mammal, primate, mouse, rat, dog, cat, horse, cow, fowl, insect, *Drosophila*, and *C. elegans*. Most preferably, the precursor cells are vertebrate, more preferably mammalian, and most preferably human. In a preferred embodiment, the precursor cells are have not gone through a "crisis" or "senescence" phase resulting in cell line characteristics (e.g. transformation resulting in a stable phenotypic change (see Freshney, 1994, In "Culture of Animal Cells—A manual of Basic Technique," 3.sup.rd Edition at p. 12, John Wiley & Sons, Inc.). In a preferred embodiment, the precursor cells are primary cells. The term "primary cells" indicates that the cells are have not been through a subculture following their explantation from a tissue source, such as a mammalian subject.

Generally, though not necessarily, the precursor cells are pluripotent stem cells or multipotent progenitor cells. In one embodiment, the precursor cells are stem cells. In another embodiment, the precursor cells are progenitor cells. The precursor cells can be isolated from a cell population, if desired, before or after immortalization.

In a specific embodiment, the precursor cells are hematopoietic stem cells. In a specific embodiment, the precursor cells are hematopoietic progenitor cells.

In a specific embodiment, the precursor cells are a population of cells enriched for hematopoietic stem cells. In another embodiment, the precursor cells are a population of cells enriched for hematopoietic stem and progenitor cells.

Sources of precursor cells include but are not limited to: umbilical CB, placental blood, peripheral blood (e.g., mobilized peripheral blood), bone marrow (e.g., from femurs, hips, ribs, sternum and other bones), embryonic cells (including embryonic stem cells and hematopoeitic precursors of HSC derived from embryonic stem cells, induced pluripotent stem cells or HSC or hematopoietic precursors derived by reprogramming (see Gazit et al., Stem Cell Reports, Vol. 1, 266-280, 2013), aortal-gonadal-mesonephros derived cells, lymph, liver (e.g., fetal liver), thymus, and spleen. Sources of precursor cells further include fetal blood, neonatal blood (from an infant in the first 28 days after birth), blood from an infant under 12 months of age, blood from a toddler between 1 year and 3 years of age, blood form a child between 3 and 18 years of age, and adult blood (i.e., derived from a subject who is older than 18 years of age). As will be understood by one of ordinary skill in the art, all collected samples can be screened for undesirable components and discarded, treated or used according to accepted current standards.

Umbilical CB and/or placental blood can be obtained by any method known in the art. The use of cord or placental blood as a source of CB stem cells provides numerous advantages, including that the cord and placental blood can be obtained easily and without trauma to the donor. See, e.g., U.S. Pat. No. 5,004,681 for a discussion of collecting cord and placental blood at the birth of a human. In one embodiment CB collection is performed by the method disclosed in U.S. Pat. No. 7,147,626.

Collections should be made under sterile conditions. Immediately upon collection, cord or placental blood should be mixed with an anticoagulant. Such an anticoagulant can be any known in the art, including but not limited to CPO (citrate-phosphate-dextrose), ACD (acid citrate-dextrose), Alsever's solution (Alsever et al., 1941, N.Y. St. J. Med. 41:126), De Gowin's Solution (De Gowin, et al., 1940, J. Am. Med. Ass. 114:850), Edglugate-Mg (Smith, et al., 1959, J. Thorac. Cardiovasc. Surg. 38:573), Rous-Tumer Solution (Rous and Turner, 1916, J. Exp. Med. 23:219), other glucose mixtures, heparin, ethyl biscoumacetate, etc. See, generally, Hum, 1968, Storage of Blood, Academic Press, New York, pp. 26-160. In particular embodiments, ACD can be used.

The CB can preferably be obtained by direct drainage from the cord and/or by needle aspiration from the delivered placenta at the root and at distended veins. See, generally, U.S. Pat. No. 5,004,681. Preferably, the collected human CB and/or placental blood is free of contamination.

In certain embodiments, HSC are obtained from the fetal blood from the fetal circulation at the placental root with the use of needle guided ultrasound, by placentocentisis, or by fetoscopy as described in sec. 5.4.5 of U.S. Pat. No. 7,399, 633. In specific embodiments, HSC are obtained from Wharton's jelly as described in sec. 5.4.5 of U.S. Pat. No. 7,399,633.

Peripheral blood is preferably mobilized prior to its collection. Peripheral blood can be mobilized by any method known in the art. Peripheral blood can be mobilized by treating the subject from whom precursor cells are to be collected with any agent(s), described herein or known in the art, that increase the number of precursor cells circulating in the peripheral blood of a subject. For example, in some embodiments, peripheral blood is mobilized by treating the subject from whom precursor cells are to be collected with one or more cytokines or growth factors (e.g., G-CSF, kit ligand (KL), IL-1, IL-7, IL-8, IL-11, Flt3 ligand, SCF, thrombopoietin, or GM-CSF (such as sargramostim)). Different types of G-CSF that can be used in the methods for mobilization of peripheral blood include, without limitation, filgrastim and longer acting G-CSF-pegfilgrastim. In certain embodiments, peripheral blood is mobilized by treating the subject from whom precursor cells are to be collected with one or more chemokines (e.g., macrophage inflammatory protein-I a (MIP1a/CCL3)), chemokine receptor ligands (e.g., chemokine receptor 2 ligands GROP and GROPM), chemokine receptor analogs (e.g., stromal cell derived factor-1a (SDF-1a) peptide analogs such as CTCE-0021, CTCE-0214, or SDF-1a such as Met-SDF-1p), or chemokine receptor antagonists (e.g., chemokine (C—X—C motif) receptor 4 (CXCR4) antagonists such as AMD3100). In some embodiments, peripheral blood is mobilized by treating the subject from whom precursor cells are to be collected with one or more anti-integrin signaling agents (e.g., function blocking anti-very late antigen 4 (VLA-4) antibody, or anti-vascular cell adhesion molecule 1 (VCAM-1)). In other embodiments, peripheral blood is mobilized by treating the subject from whom precursor cells are to be collected with one or more cytotoxic drugs such as cyclophosphamid, etoposide or paclitaxel. In particular embodiments, peripheral blood can be mobilized by administering to a subject one or more of the agents listed above for a certain period of time. For example, the subject can be treated with one or more agents (e.g., G-CSF) via injection (e.g., subcutaneous, intravenous or intraperitoneal), once daily or twice daily, for 1, 2, 3, 4, 5, 6, 7, 8, 9, 10, 11, 12, 13 or 14 days prior to collection of precursor cells. In specific embodiments, precursor cells are collected within 1, 2, 3, 4, 5, 6, 7, 8, 12, 14, 16, 18, 20 or 24 hours after the last dose of an agent used for mobilization of peripheral blood. In some embodiments, peripheral blood is mobilized by treating the subject from whom precursor cells are to be collected with two or more different types of agents described above or known in the art, such as a growth factor (e.g., G-CSF) and a chemokine receptor antagonist (e.g., CXCR4 receptor antagonist such as AMD3100), or a growth factor (e.g., G-CSF or KL) and an anti-integrin agent (e.g., function blocking VLA-4 antibody). In particular embodiments, different types of mobilizing agents are administered concurrently or sequentially. Methods of mobilization of peripheral blood are known in the art (see, e.g., Craddock et al., 1997, Blood 90(12):4779-4788; Jin et al., 2008, Journal of Translational Medicine 6:39; Pelus, 2008, Curr. Opin. Hematol. 15(4):285-292; Papayannopoulou et al., 1998, Blood 91(7):2231-2239; Tricot et al., 2008, Haematologica 93(11):1739-1742; Weaver et al., 2001, Bone Marrow Transplantation 27(2): S23-S29).

Precursor cells from bone marrow can be obtained, e.g., directly from bone marrow from the posterior iliac crest by needle aspiration (see, e.g., Kodo et al., 1984, J. Clin Invest. 73:1377-1384), or from the blood following pre-treatment with cytokines (such as G-CSF) that induce cells to be released from the bone marrow compartment. Precursor cells from peripheral blood can be collected from the blood through a syringe or catheter inserted into a subject's vein. For example, the peripheral blood can be collected using an apheresis machine. Blood flows from the vein through the catheter into an apheresis machine, which separates the precursor cells from the rest of the blood and then returns the blood to the subject's body. Apheresis can be performed for several days (e.g., 1 to 5 days) until enough precursor cells have been collected.

Once precursor cells are isolated or collected, the blood can be processed to produce an enriched precursor cells population. Enriched precursor cells produced from umbilical CB or placental blood can form a population of CB stem cells. Preferably, the enriched precursor cells are enriched in CD34+ HSC (and, thus, T cell depleted). Enrichment thus can refer to a process wherein the percentage of HSC in the sample is increased (relative to the percentage in the sample before the enrichment procedure). Purification is one example of enrichment. In certain embodiments, the increase in the number of CD34+ cells (or other suitable antigen-positive cells) as a percentage of cells in the enriched sample, relative to the sample prior to the enrichment procedure, is at least 25-, 50-, 75-, 100-, 150-, 200, 250-, 300-, 350-fold, and preferably is 100-200 fold. In a preferred embodiment, the CD34+ cells are enriched using a monoclonal antibody to CD34, which antibody is conjugated to a magnetic bead, and a magnetic cell separation device to separate out the CD34+ cells. In some embodiments, using anti-CD34 antibodies, HSC are enriched from 1-2% of a normal bone marrow cell population to approximately 50-80% of the population, as described in sec. 5.4.1.1 of U.S. Pat. No. 7,399,633.

Any technique known in the art for cell separation/selection can be used to carry out enrichment for a cell type such as HSC. For example, methods which rely on differential expression of cell surface markers can be used.

Procedures for separation may include magnetic separation, using antibody-coated magnetic beads; fluorescence activated cell sorting (FACS); affinity chromatography; cytotoxic agents joined to a monoclonal antibody or used in conjunction with a monoclonal antibody, e.g., complement and cytotoxins; and "panning" with antibody attached to a solid matrix, e.g., plate, or other convenient technique. Techniques providing accurate separation/selection include fluorescence activated cell sorters, which can have varying degrees of sophistication, e.g., a plurality of color channels, low angle and obtuse light scattering detecting channels, impedance channels, etc.

Antibodies may be conjugated with markers, such as magnetic beads, which allow for direct separation, biotin, which can be removed with avidin or streptavidin bound to a support, fluorochromes, which can be used with a fluorescence activated cell sorter, or the like, to allow for ease of separation of the particular cell type. Any technique may be employed which is not unduly detrimental to the viability of the remaining cells. In one embodiment, the enrichment of HSC is affected by contacting a precursor cell sample with a solid substrate (e.g., beads, flask, magnetic particles) to which antibodies are bound, and by removing any unbound cells, wherein the HSC can be found either in the cells bound to the solid substrate or in the unbound cells depending on the antibodies used.

In one embodiment of the present disclosure, a precursor cell sample (e.g., a fresh CB unit) is processed to select for, i.e., enrich for, CD34+ cells using anti-CD34 antibodies directly or indirectly conjugated to magnetic particles in connection with a magnetic cell separator, for example, the CliniMACS® Cell Separation System (Miltenyi Biotec, Bergisch Gladbach, Germany), which employs nano-sized super-paramagnetic particles composed of iron oxide and dextran coupled to specific monoclonal antibodies. The CliniMACS® Cell Separator is a closed sterile system, outfitted with a single-use disposable tubing set.

Similarly, CD133+ cells can be enriched using anti-CD133 antibodies. In a specific embodiment, CD34+CD90+ cells are enriched for. Similarly, cells expressing CD43, CD45RO, CD45RA, CD59, CD90, CD109, CD117, CD166, HLA DR, or a combination of the foregoing, can be enriched for using antibodies against the antigen.

In one embodiment, HSC express CD34 (CD34+) and lack CD38 expression (CD38). In some embodiments, HSC are selected and/or enriched for CD34+CD38– cells. In specific embodiments, HSC are CD34+ and CD3T, CD38–, HLA DK and/or Thy-1$^{lo}$. In some embodiments, HSC are selected and/or enriched for CD34+ and CD33, CD38-, HLA DK and/or Thy-1$^{lo}$ cells. In particular embodiments, human HSC are CD45Ra−, CD19− and/or c-kit+. In some embodiments, HSC are selected and/or enriched for CD45Ra−, CD19− and/or c-kit+ cells. In one embodiment, HSC express vascular endothelial growth factor receptor 2 (VEGFR2). In some embodiments, HSC are selected and/or enriched for VEGFR2, which can be used as a marker for HSC.

HSC can also be enriched as described in sec. 5.4.1.1 of U.S. Pat. No. 7,399,633. In particular, human HSC can be enriched by incubating a sample with antibodies that recognize one or more of glycophorin A, CD3, CD24, CD16, CD14, CD34, CD45Ra, CD36, CD56, CD2, CD19, CD20, CD66a and CD66b, and separating the antibody-bound cells from non-antibody bound cells. In some of these embodiments, the non-antibody bound cell population would be enriched for HSC. In some embodiments My10 and HLA-DR are used to obtain enriched HSC. In some embodiments, T lymphocyte depletion is used to enrich for HSC, e.g., by pretreating cells with a monoclonal antibody that recognizes a T cell antigen plus complement. In one embodiment, glycophorin A antibody is used to select for or against erythrocytes. In other embodiments, antibodies against CD14, CD16, CD66a and CD66b are used to select for or against monocytes. In other embodiments, antibodies against CD24, CD3, CD19, CD20, CD56, CD2 are used to select for or against B and T lymphocytes and NK cells. In yet another embodiment, antibodies against CD45RA and CD36 are used to select for or against T-cells, B-cells, granulocytes, platelets, monocytes, differentiated erythroid precursors, and some committed mature progenitors. Markers of pre-B progenitor cells can be MHC class II antigens. CD21 is a marker of mature B cells. In specific embodiments, antibodies which can be used for enrichment of HSC include My-10 and 3C5 (which recognize CD34), or RFB-1 (which recognizes CD99 and identifies populations of BFU-E cells). Other antibodies against the above-mentioned hematopoietic antigens are disclosed in U.S. Pat. No. 5,877,299.

The above-mentioned antibodies can be used alone or in combination with procedures such as "panning" (Broxmeyer et al., 1984, J. Clin. Invest. 73:939-953) or fluorescence activated cell-sorting (FACS) (Williams et al., 1985, J. Immunol. 135:1004; Lu et al., 1986, Blood 68(1):126-133) to isolate the cells containing surface determinants recognized by these antibodies, as described in sec. 5.4.1.1 of U.S. Pat. No. 7,399,633.

In a specific embodiment, the HSC (e.g., from umbilical CB and/or placental blood) sample are red cell depleted, and the number of CD34+ cells in the red cell depleted fraction is calculated. Preferably, the HSC (e.g. umbilical CB and/or placental blood) samples containing more than 3.5 million CD34+ cells are enriched by the enrichment methods described above. After HSC have been isolated according to the enrichment methods described above or other methods known in the art, the enriched HSC can be expanded in order to increase the number of HSC, e.g., CD34+ cells. In less preferred embodiments, the methods described herein can be applied without prior enrichment, or prior to enrichment.

In some embodiments, precursor cells that are subjected to expansion using the methods described herein are fresh, i.e., they have not been previously cryopreserved and thawed. In other embodiments, precursor cells that are subjected to expansion using the methods described herein have been cryopreserved and thawed. The precursor cells can be derived, e.g., from peripheral blood (such as mobilized peripheral blood), bone marrow, umbilical CB, or placental blood.

1.7 Methods of Use

Methods disclosed herein include treating subjects (humans, veterinary animals (dogs, cats, reptiles, birds, etc.) livestock (horses, cattle, goats, pigs, chickens, etc.) and research animals (monkeys, rats, mice, fish, etc.) with precursor cells expanded as disclosed herein. Treating subjects includes delivering therapeutically effective amounts. Therapeutically effective amounts include those that provide effective amounts, prophylactic treatments and/or therapeutic treatments.

An "effective amount" is the amount of precursor cells necessary to result in a desired physiological change in the subject. Effective amounts are often administered for research purposes. In particular embodiments, an effective amount results in an increased number of SCID repopulating cells in an expanded sample determined by limiting-dilution analysis as shown by enhanced engraftment in NOD/SCID mice infused with the expanded sample, relative to that seen with the unexpanded sample, where the unexpanded sample and expanded sample are from different aliquots of the same sample, wherein the expanded sample but not the unexpanded sample is subjected to the expansion technique. Effective amounts can also be determined using animal models for long-term engrafting potential of HSC such as the SCID-hu bone model (Kyoizumi et al. (1992) Blood 79:1704; Murray et al. (1995) Blood 85(2) 368-378) and the in utero sheep model (Zanj ani et al. (1992) J. Clin. Invest. 89:1179)). For a review of animal models of human hematopoiesis, see Srour et al. (1992) J. Hematother. 1:143-153 and the references cited therein. Effective amounts can also be assessed in vitro models such as the long-term culture-initiating cell (LTCIC) assay, based on a limiting dilution analysis of the number of clonogenic cells produced in a stromal co-culture after 5 to 8 weeks (Sutherland et al. (1990) Proc. Nat'l Acad. Sci. 87:3584-3588). The LTCIC assay has been shown to correlate with another commonly used stem cell assay, the cobblestone area forming cell (CAFC) assay, and with long-term engrafting potential in vivo (Breems et al. (1994) Leukemia 8:1095).

A "prophylactic treatment" includes a treatment administered to a subject who does not display signs or symptoms of a deficient cell population or displays only early signs or symptoms of a deficient cell population such that treatment is administered for the purpose of diminishing, preventing, or decreasing the risk of developing the deficient cell population further. Thus, a prophylactic treatment functions as a preventative treatment against a deficient cell population.

A "therapeutic treatment" includes a treatment administered to a subject who displays symptoms or signs of a deficient cell population and is administered to the subject for the purpose of diminishing or eliminating those signs or symptoms of the deficient cell population. The therapeutic treatment can reduce, control, or eliminate the presence of the deficient cell population.

For administration, therapeutically effective amounts (also referred to herein as doses) can be initially estimated based on results from in vitro assays and/or animal model studies. The actual dose amount administered to a particular subject can be determined by a physician, veterinarian or researcher taking into account parameters such as physical and physiological factors including target, body weight, severity of cell deficiency, previous or concurrent therapeutic interventions, idiopathy of the subject and route of administration.

Therapeutically effective amounts can include as few as several hundred cells (or fewer) to as many as several million or more. In specific embodiments, therapeutically effective amounts range from $10^3$ to $10^8$ cells per 100 kg. In additional embodiments, and in human subjects, therapeutically effective amounts can include between $10^3$ to $10^8$ cells per 100 kg per infusion; $10^4$ to $10^9$ cells per 100 kg per infusion; or $10^5$ and $10^{13}$ cells per 100 kg per infusion. In another embodiment, therapeutically effective amounts can include $1\times10^8$ to $5\times10^{12}$ cells per 100 kg per infusion. In another embodiment, therapeutically effective amounts can include between $1\times10^9$ and $5\times10^{11}$ cells per 100 kg person per infusion. For example, dosages such as $4\times10^9$ cells per 100 kg and $2\times10^{11}$ cells can be infused per 100 kg.

In some embodiments, a single administration of precursor cells are provided. In other embodiments, multiple administrations are used. Multiple administrations can be provided over periodic time periods such as an initial treatment regime of 3 to 7 consecutive days, and then repeated at other times.

Methods of introduction include but are not limited to intradermal, intramuscular, intraperitoneal, intravenous, subcutaneous, intranasal, and epidural routes. The precursor cells may be administered by any convenient route, for example by infusion or bolus injection, by absorption through epithelial or mucocutaneous linings (e.g., oral mucosa, rectal and intestinal mucosa, etc.) and may be administered together with other biologically active agents. Intravenous administration also affords ease, convenience and comfort at higher levels than other modes of administration. In certain applications, systemic administration by intravenous infusion is more effective overall. In another embodiment, the precursor cells are administered to an individual by infusion into the superior mesenteric artery or celiac artery. The precursor cells may also be delivered locally by irrigation down the recipient's airway or by direct injection into the mucosa of the intestine.

The expanded precursor cells can be used for a variety of applications. In one embodiment, the precursor cells are used for transplantation, sometimes referred to as cell-based therapies or cell replacement therapies, such as bone marrow transplants, gene therapies, tissue engineering, and in vitro organogenesis. As one example, hematopoietic progenitor cell expansion for bone marrow transplantation is a potential application of human bone marrow cultures. Human autologous and allogeneic bone marrow transplantation are currently used as therapies for diseases such as leukemia, lymphoma, and other life-threatening diseases. For these procedures, however, a large amount of donor bone marrow must be removed to ensure that there are enough cells for engraftment. The methods of the present disclosure circumvent this problem. Methods of transplantation are known to those skilled in the art.

Several terms are used herein with respect to transplantation therapies, also known as cell-based therapies or cell replacement therapy. The terms autologous transfer, autologous transplantation, autograft and the like refer to treatments wherein the cell donor is also the recipient of the cell replacement therapy. The terms allogeneic transfer, allogeneic transplantation, allograft and the like refer to treatments wherein the cell donor is of the same species as the recipient of the cell replacement therapy, but is not the same individual. A cell transfer in which the donor's cells have been histocompatibly matched with a recipient is sometimes referred to as a syngeneic transfer. The terms xenogeneic transfer, xenogeneic transplantation, xenograft and the like refer to treatments wherein the cell donor is of a different species than the recipient of the cell replacement therapy.

Transplantation of precursor cells may be useful in the treatment of hematopoietic disorders and diseases. In one embodiment, the precursor cells are used to treat or prevent a hematopoietic disorder or disease characterized by a failure or dysfunction of normal blood cell production and maturation cell. In another embodiment, the precursor cells are used to treat or prevent a hematopoietic disorder or disease resulting from a hematopoietic malignancy. In yet another embodiment, the precursor cells are used to treat or prevent a hematopoietic disorder or disease resulting from immunosuppression, particularly immunosuppression in subjects with malignant, solid tumors. In yet another embodiment, the precursor cells are used to treat or prevent an autoimmune disease affecting the hematopoietic system. In yet another embodiment, the precursor cells are used to treat or prevent a genetic or congenital hematopoietic disorder or disease.

Additional examples of particular hematopoietic diseases and disorders which can be treated by precursor cells expanded by the methods disclosed herein include: (i) diseases resulting from a failure or dysfunction of normal blood cell production and maturation (e.g., hyperproliferative stem cell disorders; aplastic anemia; pancytopenia; agranulocytosis; thrombocytopenia; red cell aplasia; Blackfan-Diamond syndrome due to drugs, radiation, or infection idiopathic); (ii) Hematopoietic malignancies (e.g., acute lymphoblastic (lymphocytic) leukemia; chronic lymphocytic leukemia; acute myelogenous leukemia; chronic myelogenous leukemia; acute malignant myelosclerosis; multiple myelom; a polycythemia vera; agnogenic myelometaplasia; Waldenstrom's macroglobulinemia; Hodgkin's lymphoma; non-Hodgkin's lymphoma); (iii) immunosuppression in patients with malignant, solid tumors (e.g., malignant melanoma; carcinoma of the stomach; ovarian carcinoma; breast carcinoma; small cell lung carcinoma; retinoblastoma; testicular carcinoma; glioblastoma; rhabdomyosarcoma; neuroblastoma; Ewing's sarcoma; lymphoma; (iv) autoimmune diseases (e.g., rheumatoid arthritis; diabetes type I; chronic hepatitis; multiple sclerosis; systemic lupus erythematosus; (v) genetic (congenital) disorders (e.g., anemias; familial aplastic; Fanconi's syndrome; Bloom's syndrome; pure red cell aplasia (PRCA); dyskeratosis congenital; Blackfan-Diamond syndrome; congenital dyserythropoietic syndromes I-IV; Chwachmann-Diamond syndrome; dihydrofolate reductase deficiencies; formamino transferase deficiency; Lesch-Nyhan syndrome; congenital spherocytosis; congenital elliptocytosis; congenital stomatocytosis; congenital Rh null disease; paroxysmal nocturnal hemoglobinuria; G6PD (glucose-6-phosphate dehydrogenase) variants 1, 2, 3; pyruvate kinase deficiency; congenital erythropoietin sensitivity deficiency; sickle cell disease and trait; thalassemia alpha, beta, gamma; met-hemoglobinemia; congenital disorders of immunity; severe combined immunodeficiency disease (SCID); bare lymphocyte syndrome; ionophore-responsive combined immunodeficiency; combined immunodeficiency with a capping abnormality; nucleoside phosphorylase deficiency; granulocyte actin deficiency; infantile agranulocytosis; Gaucher's disease; adenosine deaminase deficiency; Kostmann's syndrome; reticular dysgenesis; congenital leukocyte dysfunction syndromes); (vi) others (e.g., osteopetrosis; myelosclerosis; acquired hemolytic anemias; acquired immunodeficiencies; infectious disorders causing primary or secondary immunodeficiencies bacterial infections (e.g., Brucellosis, Listerosis, tuberculosis, leprosy); parasitic infections (e.g., malaria, Leishmaniasis); fungal infections; disorders involving disproportions in lymphoid cell sets and impaired immune functions due to aging; phagocyte disorders; Kostmann's agranulocytosis; chronic granulomatous disease; Chediak-Higachi syndrome; neutrophil actin deficiency; neutrophil membrane GP-180 deficiency; metabolic storage diseases; mucopolysaccharidoses; mucolipidoses; miscellaneous disorders involving immune mechanisms; Wiskott-Aldrich Syndrome; al-antitrypsin deficiency).

Expanded precursor cells are also useful as a source of cells for specific hematopoietic lineages. The maturation, proliferation and differentiation of expanded hematopoietic cells into one or more selected lineages may be effected through culturing the cells with appropriate factors including, but not limited to, erythropoietin (EPO), colony stimulating factors, e.g., GM-CSF, G-CSF, or M-CSF, SCF, interleukins, e.g., IL-1, -2, -3, -4, -5, -6, -7, -8, -13, etc., or with stromal cells or other cells which secrete factors responsible for stem cell regeneration, commitment, and differentiation. As is understood by one of ordinary skill in the art, differentiated precursor cells may be used in accordance with the methods of use described herein.

The disclosure includes formulating expanded precursor cells for administration to a subject as a pharmaceutical composition comprising a therapeutically effective amount of the precursor cells. In one embodiment, the precursor cells are substantially purified. Formulation of pharmaceutical compositions is well known in the art. In particular embodiments, pharmaceutical compositions can include pharmaceutically acceptable carrier or excipients such as saline, buffered saline, dextrose, water, glycerol, ethanol, and combinations thereof. Pharmaceutical compositions can also contain minor amounts of wetting or emulsifying agents, or pH buffering agents. The pharmaceutical composition can be a liquid solution, suspension, or emulsion. In particular embodiments, pharmaceutical compositions can also include a solubilizing agent and/or a local anesthetic such as lignocaine to ease pain at a site of the injection.

2. EXEMPLARY EMBODIMENTS

1. A method for expanding precursor cells comprising culturing the precursor cells in the presence of a media comprising an immobilized LILRB2 agonist with a molecular weight of at least 225 kD wherein the culturing is effective to maintain expansion of the precursor cells beyond a time at which precursor cells cultured in the media lacking an immobilized LILRB2 agonist with a molecular weight of at least 225 kD stop proliferating and/or die.
2. A method of embodiment 1 wherein the LILRB2 agonist has a molecular weight of at least 250 kD
3. A method of embodiment 1 or 2 wherein the LILRB2 agonist is multimerized.
4. A method of embodiments 1, 2 or 3 wherein the LILRB2 agonist is an angiopoietin-like protein (Angptl) or fragment thereof.
5. A method of embodiment 4 wherein the Angptl or fragment thereof comprises the coiled-coil domain of the Angptl.
6. A method of embodiment 4 or 5 wherein the LILRB2 agonist is Angptl 1 or a fragment thereof, Angptl2 or a fragment thereof, Angptl3 or a fragment thereof, Angptl4 or a fragment thereof, Angptl5 or a fragment thereof, Angptl7 or a fragment thereof, or Mfap4 or a fragment thereof.
7. A method of embodiment 1 wherein the LILRB2 agonist is an LILRB2 receptor antibody.
8. A method of embodiment 7 wherein the LILRB2 antibody is a monoclonal antibody or a polyclonal antibody.
9. A method of any one of embodiments 1-8 wherein the LILRB2 agonist binds the Ig1 domain of LILRB2.
10. A method of any of embodiments 1-8 wherein the LILRB2 agonist binds the Ig4 domain of LILRB2.
11. A method of any of embodiments 1-8 wherein the LILRB2 agonist binds the Ig1 domain and the Ig4 domain of LILRB2.
12. A method of any of embodiments 1-8 wherein the LILRB2 agonist binds the amino acids at positions 92-100 of LILRB2 within the Ig1 domain.
13. A method of any of embodiments 1-8 wherein the LILRB2 agonist binds the amino acids at positions 94, 95 and/or 96 of LILRB2 within the Ig1 domain.
14. A method of any of embodiments 1-8 wherein the LILRB2 agonist binds the amino acids at positions 390-396 of LILRB2 within the Ig4 domain.
15. A method of any of embodiments 1-8 wherein the LILRB2 agonist binds the amino acids at 392 and 393 of LILRB2 within the Ig4 domain.
16. A method of any of embodiments 1-15 wherein the media is serum free.
17. A method of any of embodiments 1-16 wherein the media comprises 1-100 µg/ml immobilized LILRB2 agonist.
18. A method of embodiment 17 wherein the media comprises 25 µg/ml immobilized LILRB2 agonist.
19. A method of embodiment 17 or 18 wherein the media further comprises SCF; TPO and Flt3-ligand.
20. A method of embodiment 17 or 18 wherein the media further comprises 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 ng/ml SCF; 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 ng/ml TPO and 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 ng/ml Flt3-ligand.
21. A method of embodiment 20 wherein the media comprises 10 ng/ml SCF.
22. A method of embodiment 20 wherein the media comprises 5 ng/ml TPO.
23. A method of embodiment 20 wherein the media comprises 10 ng/ml Flt3-ligand.
24. A method of embodiment 20 wherein the media comprises growth factors: 10 ng/ml SCF; 5 ng/ml TPO; and 10 ng/ml Flt3-ligand.
25. A method of any one of embodiments 1-25 wherein the precursor cells are hematopoietic stem cells or hematopoietic progenitor cells.
26. A method of any one of embodiments 1-25 wherein the precursor cells are hematopoietic stem cells.
27. A method of any one of embodiments 1-25 wherein the precursor cells are obtained from bone marrow, umbilical cord blood, placental blood, or Wharton's jelly.
28. A method of any one of embodiments 1-25 wherein the precursor cells are obtained from fetal or neonatal blood.
29. A method for expanding precursor cells comprising culturing the precursor cells in the presence of a media comprising an LILRB2 agonist and a Notch agonist wherein the culturing is effective to maintain expansion of the precursor cells beyond a time at which precursor cells cultured in the media lacking an LILRB2 agonist and a Notch agonist stop proliferating and/or die.
30. A method of embodiment 29 wherein the LILRB2 agonist is immobilized in the culture media.

31. A method of embodiment 29 or 30 wherein the Notch agonist is immobilized in the culture media.

32. A method of embodiment 29, 30 or 31 wherein the LILRB2 agonist has a molecular weight of at least 225 kD or at least 250 kD.

33. A method of any one of embodiments 29-32 wherein the LILRB2 agonist is multimerized.

34. A method of any one of embodiments 29-33 wherein the LILRB2 agonist is an angiopoietin-like protein (Angptl) or fragment thereof.

35. A method of embodiment 34 wherein the Angptl or fragment thereof comprises the coiled-coil domain of the Angptl.

36. A method of embodiment 34 or 35 wherein the LILRB2 agonist is Angptl 1 or a fragment thereof, Angptl2 or a fragment thereof, Angptl3 or a fragment thereof, Angptl4 or a fragment thereof, Angptl5 or a fragment thereof, Angptl7 or a fragment thereof, or Mfap4 or a fragment thereof.

37. A method of any one of embodiments 29-33 wherein the LILRB2 agonist is an LILRB2 receptor antibody.

38. A method of embodiment 37 wherein the LILRB2 antibody is a monoclonal antibody or a polyclonal antibody.

39. A method of any one of embodiments 29-38 wherein the LILRB2 agonist binds the Ig1 domain of LILRB2.

40. A method of any one of embodiments 29-38 wherein the LILRB2 agonist binds the Ig4 domain of LILRB2.

41. A method of any one of embodiments 29-38 wherein the LILRB2 agonist binds the Ig1 domain and the Ig4 domain of LILRB2.

42. A method of any one of embodiments 29-38 wherein the LILRB2 agonist binds the amino acids at positions 92-100 of LILRB2 within the Ig1 domain.

43. A method of any one of embodiments 29-38 wherein the LILRB2 agonist binds the amino acids at positions 94, 95 and/or 96 of LILRB2 within the Ig1 domain.

44. A method of any one of embodiments 29-38 wherein the LILRB2 agonist binds the amino acids at positions 390-396 of LILRB2 within the Ig4 domain.

45. A method of any one of embodiments 29-38 wherein the LILRB2 agonist binds the amino acids at 392 and 393 of LILRB2 within the Ig4 domain.

46. A method of any one of embodiments 29-45 wherein the Notch agonist is an extracellular, Notch-interacting domain of a Delta protein.

47. A method of any one of embodiments 29-45 wherein the Notch agonist is Delta$^{ext-IgG}$.

48. A method of any one of embodiments 29-45 wherein the Notch agonist is in dimeric form.

49. A method of any one of embodiments 29-49 wherein the media is serum free.

50. A method of any one of embodiments 29-50 wherein the media comprises 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 µg/ml immobilized LILRB2 agonist.

51. A method of embodiment 50 wherein the media comprises 25 µg/ml immobilized LILRB2 agonist.

52. A method of embodiment 50 wherein the media comprises 0.025, 0.050, 0.075, 0.01, 0.05, 0.08 0.1, 0.5, 0.75, 1, 2, 3, 4, 5, 10, 15, 20, 25, 30, 35, 40, 45, 50, 55, 60, 65, 70, 75, 80, 85, 90, 95 or 100 µg/ml immobilized LILRB2 agonist.

53. A method of any one of embodiments 29-52 wherein the media comprises 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 µg/ml Notch agonist.

54. A method of embodiment 53 wherein the media comprises 0.5 to 2.5 µg/ml Notch agonist.

55. A method of any one of embodiments 29-52 wherein the media further comprises SCF; TPO and Flt3-ligand.

56. A method of embodiment 55 wherein the media further comprises 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 ng/ml SCF; 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 ng/ml TPO and 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 ng/ml Flt3-ligand.

57. A method of embodiment 56 wherein the media comprises 10 ng/ml SCF.

58. A method of embodiment 56 wherein the media comprises 5 ng/ml TPO.

59. A method of embodiment 56 wherein the media comprises 10 ng/ml Flt3-ligand.

60. A method of embodiment 56 wherein the media comprises 10 ng/ml SCF; 5 ng/ml TPO; and 10 ng/ml Flt3-ligand.

61. A method of any one of embodiments 29-52 wherein the media further comprises SCF, Flt3-ligand, IL-6, TPO, FGF1 and IL-3.

62. A method of embodiment 61 wherein the media comprises SCF, Flt3-ligand, IL-6, TPO, FGF1, IL-3 and heparin.

63. A method of embodiment 61 wherein the media further comprises 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 ng/ml SCF, 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 ng/ml Flt3-ligand, 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 ng/ml IL-6, 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 ng/ml TPO, 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 ng/ml FGF1 and 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 ng/ml IL-3.

64. A method of embodiment 63 wherein the media further comprises 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 µg/ml heparin.

65. A method of embodiment 61 wherein the media further comprises 50 ng/ml SCF, 50 ng/ml Flt3-ligand, 50 ng/ml IL-6, 50 ng/ml TPO, 20 ng/ml FGF1 and 10 ng/ml IL-3.

66. A method of embodiment 65 wherein the media further comprises 10 µg/ml heparin.

67. A method of any one of embodiments 29-66 wherein the media further comprises retronectin.

68. A method of embodiment 67 wherein the media further comprises 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 µg/ml retronectin.

69. A method of embodiment 68 wherein the media further comprises 5 µg/ml retronectin.

70. A method of any one of embodiments 29-69 wherein the precursor cells are hematopoietic stem cells or hematopoietic progenitor cells.

71. A method of any one of embodiments 29-69 wherein the precursor cells are hematopoietic stem cells.

72. A method of any one of embodiments 29-69 wherein the precursor cells are obtained from bone marrow, umbilical cord blood, placental blood, or Wharton's jelly.

73. A method any one of embodiments 29-69 wherein the precursor cells are obtained from fetal or neonatal blood.

74. A method for producing precursor cells for hematopoietic transplantation comprising culturing the precursor cells in the presence of a media comprising an immobilized LILRB2 agonist with a molecular weight of at least 225 kD wherein the culturing is effective to produce precursor cells suitable able to treat a subject when formulated for administration and administered in an effective amount.

75. A method of embodiment 74 wherein the LILRB2 agonist has a molecular weight of at least 250 kD 76. A method of embodiment 74 or 75 wherein the LILRB2 agonist is multimerized.

77. A method of embodiment 74, 75 or 76 wherein the LILRB2 agonist is an angiopoietin-like protein (Angptl) or fragment thereof.

78. A method of embodiment 77 wherein the Angptl or fragment thereof comprises the coiled-coil domain of the Angptl.

79. A method of embodiment 77 or 78 wherein the LILRB2 agonist is Angptl 1 or a fragment thereof, Angptl2 or a fragment thereof, Angptl3 or a fragment thereof, Angptl4 or a fragment thereof, Angptl5 or a fragment thereof, Angptl7 or a fragment thereof, or Mfap4 or a fragment thereof.

80. A method of embodiment 74 wherein the LILRB2 agonist is an LILRB2 receptor antibody.

81. A method of embodiment 80 wherein the LILRB2 antibody is a monoclonal antibody or a polycloncal antibody.

82. A method of any one of embodiments 74-81 wherein the LILRB2 agonist binds the Ig1 domain of LILRB2.

83. A method of any one of embodiments 74-81 wherein the LILRB2 agonist binds the Ig4 domain of LILRB2.

84. A method of any one of embodiments 74-81 wherein the LILRB2 agonist binds the Ig1 domain and the Ig4 domain of LILRB2.

85. A method of any one of embodiments 74-81 wherein the LILRB2 agonist binds the amino acids at positions 92-100 of LILRB2 within the Ig1 domain.

86. A method of any one of embodiments 74-81 wherein the LILRB2 agonist binds the amino acids at positions 94, 95 and/or 96 of LILRB2 within the Ig1 domain.

87. A method of any one of embodiments 74-81 wherein the LILRB2 agonist binds the amino acids at positions 390-396 of LILRB2 within the Ig4 domain.

88. A method of any one of embodiments 74-81 wherein the LILRB2 agonist binds the amino acids at 392 and 393 of LILRB2 within the Ig4 domain.

89. A method of any one of embodiments 74-88 wherein the media is serum free.

90. A method of any one of embodiments 74-89 wherein the media comprises 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 µg/ml immobilized LILRB2 agonist.

91. A method of embodiment 90 wherein the media comprises 25 µg/ml immobilized LILRB2 agonist.

92. A method of embodiment any one of embodiments 74-91 wherein the media further comprises SCF; TPO and Flt3-ligand.

93. A method of embodiment 92 wherein the media further comprises 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 ng/ml SCF; 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 ng/ml TPO and 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 ng/ml Flt3-ligand.

94. A method of embodiment 93 wherein the media comprises 10 ng/ml SCF.

95. A method of embodiment 93 wherein the media comprises 5 ng/ml TPO.

96. A method of embodiment 93 wherein the media comprises 10 ng/ml Flt3-ligand.

97. A method of embodiment 93 wherein the media comprises 10 ng/ml SCF; 5 ng/ml TPO; and 10 ng/ml Flt3-ligand.

98. A method of any one of embodiments 74-97 wherein the precursor cells are hematopoietic stem cells or hematopoietic progenitor cells.

99. A method of any one of embodiments 74-97 wherein the precursor cells are hematopoietic stem cells.

100. A method of any one of embodiments 74-97 wherein the precursor cells are obtained from bone marrow, umbilical cord blood, placental blood, or Wharton's jelly.

101. A method of any one of embodiments 74-97 wherein the precursor cells are obtained from fetal or neonatal blood.

102. A method for expanding precursor cells comprising culturing the precursor cells in the presence of a media comprising an LILRB2 agonist and a Notch agonist wherein the culturing is effective to maintain expansion of the precursor cells beyond a time at which precursor cells cultured in the media lacking an LILRB2 agonist and a Notch agonist stop proliferating and/or die.

103. A method of embodiment 102 wherein the LILRB2 agonist is immobilized in the culture media.

104. A method of embodiment 102 or 103 wherein the Notch agonist is immobilized in the culture media.

105. A method of embodiment 102, 103 or 104 wherein the LILRB2 agonist has a molecular weight of at least 225 kD or at least 250 kD.

106. A method of any one of embodiments 102-105 wherein the LILRB2 agonist is multimerized.

107. A method of any one of embodiments 102-106 wherein the LILRB2 agonist is an angiopoietin-like protein (Angptl) or fragment thereof.

108. A method of any one of embodiments 102-107 wherein the Angptl or fragment thereof comprises the coiled-coil domain of the Angptl.

109. A method of any one of embodiments 102-108 wherein the LILRB2 agonist is Angptl 1 or a fragment thereof, Angptl2 or a fragment thereof, Angptl3 or a fragment thereof, Angptl4 or a fragment thereof, Angptl5 or a fragment thereof, Angptl7 or a fragment thereof, or Mfap4 or a fragment thereof.

110. A method of any one of embodiments 102-106 wherein the LILRB2 agonist is an LILRB2 receptor antibody.

111. A method of embodiment 110 wherein the LILRB2 antibody is a monoclonal antibody or a polycloncal antibody.

112. A method of any one of embodiments 102-111 wherein the LILRB2 agonist binds the Ig1 domain of LILRB2.

113. A method of any one of embodiments 102-111 wherein the LILRB2 agonist binds the Ig4 domain of LILRB2.

114. A method of any one of embodiments 102-111 wherein the LILRB2 agonist binds the Ig1 domain and the Ig4 domain of LILRB2.

115. A method of any one of embodiments 102-111 wherein the LILRB2 agonist binds the amino acids at positions 92-100 of LILRB2 within the Ig1 domain.

116. A method of any one of embodiments 102-111 wherein the LILRB2 agonist binds the amino acids at positions 94, 95 and/or 96 of LILRB2 within the Ig1 domain.

117. A method of any one of embodiments 102-111 wherein the LILRB2 agonist binds the amino acids at positions 390-396 of LILRB2 within the Ig4 domain.

118. A method of any one of embodiments 102-111 wherein the LILRB2 agonist binds the amino acids at 392 and 393 of LILRB2 within the Ig4 domain.

119. A method of any one of embodiments 102-118 wherein the Notch agonist is an extracellular, Notch-interacting domain of a Delta protein.

120. A method of any one of embodiments 102-118 wherein the Notch agonist is Delta$^{ext-IgG}$.

121. A method of any one of embodiments 102-118 wherein the Notch agonist is in dimeric form.

122. A method of any one of embodiments 102-121 wherein the media is serum free.

123. A method of any one of embodiments 102-122 wherein the media comprises 0.025-100 µg/ml immobilized LILRB2 agonist.

124. A method of embodiment 123 wherein the media comprises 25 µg/ml immobilized LILRB2 agonist.

125. A method of embodiment any one of embodiments 102-124 wherein the media comprises 0.08 to 25 µg/ml immobilized LILRB2 agonist.

126. A method of any one of embodiments 102-125 wherein the media comprises 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 µg/ml Notch agonist.

127. A method of embodiment 126 wherein the media comprises 0. 5 to 2.5 µg/ml Notch agonist.

128. A method of any one of embodiments 102-127 wherein the media further comprises SCF; TPO and Flt3-ligand.

129. A method of embodiment 128 wherein the media further comprises 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 ng/ml SCF; 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 ng/ml TPO and 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 ng/ml Flt3-ligand.

130. A method of embodiment 129 wherein the media comprises 10 ng/ml SCF.

131. A method of embodiment 129 wherein the media comprises 5 ng/ml TPO.

132. A method of embodiment 129 wherein the media comprises 10 ng/ml Flt3-ligand.

133. A method of embodiment 129 wherein the media comprises: 10 ng/ml SCF; 5 ng/ml TPO; and 10 ng/ml Flt3-ligand.

134. A method of any one of embodiments 102-127 wherein the media further comprises SCF, Flt3-ligand, IL-6, TPO, FGF1 and IL-3.

135. A method of embodiment 134 wherein the media comprises SCF, Flt3-ligand, IL-6, TPO, FGF1, IL-3 and heparin.

136. A method of any one of embodiments 102-127 wherein the media further comprises 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 ng/ml SCF, 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 ng/ml Flt-ligand, 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 ng/ml IL-6, 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 ng/ml TPO, 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 ng/ml FGF1 and 1-100 ng/ml IL-3.

137. A method of embodiment 136 wherein the media further comprises 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 µg/ml heparin.

138. A method of embodiment 136 or 137 wherein the media further comprises 50 ng/ml SCF, 50 ng/ml Flt3-ligand, 50 ng/ml IL-6, 50 ng/ml TPO, 20 ng/ml FGF1 and 10 ng/ml IL-3.

139. A method of embodiment 138 wherein the media further comprises 10 µg/ml heparin.

140. A method of any one of embodiments 102-139 wherein the media further comprises retronectin.

141. A method of embodiment 140 wherein the media further comprises 0.025, 0.050, 0.075, 0.01, 0.05, 0.1, 0.5, 0.75, 1, 2, 3, 4, 5, 10, 15, 20, 25, 30, 35, 40, 45, 50, 55, 60, 65, 70, 75, 80, 85, 90, 95 or 100 µg/ml retronectin.

142. A method of embodiment 141 wherein the media further comprises 5 µg/ml retronectin.

143. A method of any one of embodiments 102-142 wherein the precursor cells are hematopoietic stem cells or hematopoietic progenitor cells.

144. A method of any one of embodiments 102-142 wherein the precursor cells are hematopoietic stem cells.

145. A method of any one of embodiments 102-142 wherein the precursor cells are obtained from bone marrow, umbilical cord blood, placental blood, or Wharton's jelly.

146. A method of any one of embodiments 102-142 wherein the precursor cells are obtained from fetal or neonatal blood.

147. A chimeric receptor reporter system comprising cells expressing a fusion protein comprising at least one extracellular domain of LILRB2 and transmembrane and cytoplasmic domains of PILRβ wherein binding of an activating ligand to the extracellular domain of LILRB2 results in reporter gene expression.

148. A chimeric receptor reporter system of embodiment 147 wherein the at least one extracellular domain of LILRB2 is the Ig1 domain, the Ig2 domain, the Ig3 domain and/or the Ig4 domain.

149. A chimeric receptor reporter system of embodiment 147 wherein the at least one extracellular domain of LILRB2 is the Ig1 domain.

150. A chimeric receptor reporter system of embodiment 147 wherein the Ig1 domain includes amino acids 24-119 of LILB2.

151. A chimeric receptor reporter system of embodiment 147 wherein the at least one extracellular domain of LILRB2 is the Ig2 domain.

152. A chimeric receptor reporter system of embodiment 147 wherein the Ig2 domain includes amino acids 120-219 of LILB2.

153. A chimeric receptor reporter system of embodiment 147 wherein the at least one extracellular domain of LILRB2 is the Ig3 domain.

154. A chimeric receptor reporter system of embodiment 147 wherein the Ig3 domain includes amino acids 221-320 of LILB2.

155. A chimeric receptor reporter system of embodiment 147 wherein the at least one extracellular domain of LILRB2 is the Ig4 domain.

156. A chimeric receptor reporter system of embodiment 147 wherein the Ig4 domain includes amino acids 321-458 of LILB2.
157. A chimeric receptor reporter system of embodiment 147 wherein the at least one extracellular domain of LILRB2 includes the Ig1 domain and the Ig2 domain.
158. A chimeric receptor reporter system of embodiment 147 wherein the Ig1 domain and the Ig2 domain includes amino acids 24-219 of LILB2.
159. A chimeric receptor reporter system of embodiment 147 wherein the at least one extracellular domain of LILRB2 includes the Ig3 domain and the Ig4 domain.
160. A chimeric receptor reporter system of embodiment 147 wherein the Ig3 domain and the Ig4 domain includes amino acids 221-458 of LILB2.
161. A chimeric receptor reporter system of embodiment 147 wherein the fusion protein includes amino acids 24-458 of LILRB2.
162. A chimeric receptor reporter system of any one of embodiments 147-161 wherein the cells are T cell hybridoma cells.
163. A chimeric receptor reporter system of embodiment 162 wherein reporter gene expression results from NFAT activation.
164. A chimeric receptor reporter system of embodiment 162 or 163 wherein reporter gene expression is under the control of a NFAT-responsive promoter.
165. A method of any one of embodiments 1-25 wherein the precursor cells are embryonic stem cells; hematopoeitic precursors of HSC derived from embryonic stem cells; induced pluripotent stem cells; or HSC or hematopoietic precursors derived by reprogramming.
166. A method of any one of embodiments 29-69 wherein the precursor cells are embryonic stem cells; hematopoeitic precursors of HSC derived from embryonic stem cells; induced pluripotent stem cells; or HSC or hematopoietic precursors derived by reprogramming.
167. A method of any one of embodiments 74-97 wherein the precursor cells are embryonic stem cells; hematopoeitic precursors of HSC derived from embryonic stem cells; induced pluripotent stem cells; or HSC or hematopoietic precursors derived by reprogramming.
168. A method of any one of embodiments 102-142 wherein the precursor cells are embryonic stem cells; hematopoeitic precursors of HSC derived from embryonic stem cells; induced pluripotent stem cells; or HSC or hematopoietic precursors derived by reprogramming.

The Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

3. EXAMPLES

3.1 Example 1

A better understanding of the interaction between extrinsic factors and surface receptors on HSC will greatly benefit stem cell research and applications. Recently it was shown that several Angptls bind and activate the immune inhibitory receptor LILRB2 to support ex vivo expansion of HSC. However, the molecular basis for the interaction between Angptls and LILRB2 was unclear. Example 1 demonstrates that Angptl2 expressed in mammalian cells forms high molecular weight (HMW) species, and ligand multimerization is required for activation of LILRB2 for downstream signaling. A novel motif in the first and fourth Ig domains of LILRB2 was identified that is necessary for the receptor to be bound and activated by Angptl2. The binding of Angptl2 to LILRB2 is more potent than and not completely overlapped with the binding of another ligand HLA-G. Immobilized anti-LILRB2 antibodies induce a more potent activation of LILRB2 than Angptl2. Example 1 describes a serum-free culture containing defined cytokines and immobilized anti-LILRB2 that supports a net expansion of repopulating human CB HSCs. The elucidation of the mode of Angptl binding to LILRB2 enabled the development of this new approach for ex vivo expansion of human HSCs.

3.1.1. Example 1—Methods

Chimeric receptor reporter cells. The chimeric receptors including individual or all Ig-domains or their mutants of the extracellular domain of LILRB2 and the transmembrane and cytoplasmic domains of activating PILRβ were infected into mouse T cell hybridoma cells carrying NFAT-GFP reporter gene and DAP12 by using a retrovirus vector. Amino acid 24-458 of hLILRB2 was used to construct the full-length LILRB2 chimeric reporter. The amino acid sequences for the individual Ig domains or Ig combinations are: Ig1 (aa 24-119), Ig2 (aa 120-219), Ig3 (aa 221-320), Ig4 (aa 321-458), Ig1+2 (aa 24-219), and Ig3+4 (aa 221-458). These chimeric LILRB2-PILRβ receptor reporter cells ($5\times10^4$/well) were incubated with ligands for indicated time, and GFP was analyzed by flow cytometry. Purified Angptl2-FLAG by M2 resin or Angptl2 in conditioned medium collected from transfected 293T cells were used as indicated. For experiments using coated wells, indicated bacterially-expressed GST-Angptl2, anti-LILRB2 polyclonal antibody (pAb, #BAF2078, R&D systems), or anti-LILRB2 monoclonal antibody (mAb, #16-5149-85, eBioscience) or control antibody was pre-coated on 96 well-plates for 3 hrs in 37° C. unless otherwise indicated. When antibodies were cross-linked, 10 µg/ml pAb was incubated with 10 µg/ml streptavidin at 4° C. overnight.

Mice. NOD/SCID IL2R gamma-/-(NSG) mice were purchased and maintained at the University of Texas Southwestern Medical Center animal facilities. All animal experiments were performed with the approval of UT Southwestern Committee on Animal Care.

Plasmids and proteins. Wild-type or mutant LILRB2s were constructed into pLVX-IRES-ZsGreen (Clontech). Plasmid CMV-Kozak-human Angptl2 encoding Angptl2 or HLA-G extracellular domain (ECD) with a FLAG tag at the C-terminus was transfected into 293T cells using Lipofectamine 2000, and the conditioned medium at 48 h was collected. Angptl2-FLAG was purified using M2 resin. Bacterially-expressed GST-Angptls-FLAG was constructed in pGEX vector, and expressed and purified from bacteria. Concentrations of Angptl proteins were adjusted to the same level for flow cytometry-based binding experiments. Purified recombinant HLA-G was purchased from Origene (#TP305216).

SDS-PAGE and native polyacrylamide gel electrophoresis (PAGE). For reduced SDS-PAGE, samples were mixed with 4×loading buffer with βmercaptoethanol (BME) and loaded on 10% SDS gels. For non-reduced SDS-PAGE, samples were mixed with 4×loading buffer without BME and loaded on 10% SDS gels. For native PAGE, the PAGE gel did not contain SDS. Samples were mixed with 4×loading buffer without BME.

Fast protein liquid chromatography (FPLC). Purified GST-Angptl2 expressed from bacteria was loaded onto a 16/60 Superdex 200 gel filtration column and eluted with PBS and 2 mM EDTA. Fractions (0.6 ml) were collected, and the amount of Angptl2 in each fraction was analyzed by western blot analysis.

Human cell culture. Fresh and cryopreserved human CB cells were purchased from AllCells. All of the cells were from pooled donors. Purities of CD34+ or CD133+ cells as analyzed by flow cytometry were higher than 90%. After thawing, the cell viability tested by trypan blue exclusion was higher than 72%. The thawed cells were centrifuged and resuspended in StemSpan medium before being aliquoted for immediate transplantation or culture. StemSpan supplemented with 50 ng/ml human SCF, 10 ng/ml human TPO, and 50 ng/ml human Flt3-L with soluble or immobilized anti-LILRB2 monoclonal antibody (#165149-85, eBioscience) or polyclonal antibody (#BAF2078, R&D Systems) was used as culture medium. Fresh human CB CD34+ cells or cryopreserved CD133+ cells as indicated were plated at $5 \times 10^3$ cells/well in one well of a U-bottom 96-well plate (3799; Corning) with 200 μl of the indicated medium for 2 days. On day 3, cells were pooled from individual wells and transferred to 6-well plates at $5 \times 10^4$ cells/ml. Fresh medium was added at days 4 and 7 to keep the cell density at $2 \times 10^5$ cells/ml (day 4) or $7 \times 10^5$ cells/ml (day 7). Cells were cultured at 37° C. in 5% $CO_2$ and normal O2 or 5% O2 (low $O_2$) levels. For transplantation, cells from all the culture wells were pooled before the indicated numbers of cells were transplanted into each mouse.

NSG transplant. Uncultured or cultured progenies of human CB CD133+ or CD34+ cells at indicated days were pooled together and the indicated portions were injected intravenously via the retro-orbital route into sub-lethally irradiated (250 rad) 8-10 week old NSG mice. Eight weeks or as indicated after transplantation, bone marrow nucleated cells from transplanted animals were analyzed by flow cytometry for the presence of human cells. For secondary transplantations, bone marrow aspirates from one hind leg of a primary recipient were used to transplant two secondary recipients as described in Bryder et al., Am J Pathol. 2006; 169:338-346. Calculation of long-term repopulating cells (competitive repopulating unit, CRU) in limiting dilution experiments was conducted using L-Calc software (StemCell Technologies). See, for example, Brunstein and Wagner, Annu Rev Med. 2006; 57:403-417; Chou et al., Cell Stem Cell. 2010; 7:427-428; and Delaney et al., Nat Med. 2010; 16:232-236.

For limiting dilution analysis, mice were considered to be positive for human HSC engraftment when at least 1% (for primary transplantation) or 0.1% (for secondary transplantation) CD45/71+ human cells were detected among the mouse bone marrow cells, unless otherwise indicated.

Flow cytometry. To measure Angptl2/LILRB2 binding, plasmids for expression of LILRB2 or mutants driven from a CMV promoter were transfected into 293T cells. Cells were harvested at 48 h for analysis. Alternatively, mononuclear human CB cells were incubated with Fc block and equal amounts of FLAG-tagged Angptl2 at 4° C. for 60 min, followed by staining with anti-Flag-APC and propidium iodide. Anti-LILRB2-PE was used as indicated. Cells were analyzed using either a FACSCalibur or FACSAria instrument (Becton Dickinson).

Human hematopoietic engraftment in NSG mice was assessed following the protocol described in Himburg et al., Nat Med. 2010; 16:475-482. Briefly, bone marrow cells from recipient NSG mice were stained with antihuman CD45-PE, CD71-PE, CD15-FITC, and CD66b-FITC to quantify the total human hematopoietic (CD45/71+) cell population as well as the subset of exclusively granulopoietic (CD15/66b+) cells within this population. Cells were stained with anti-human CD34-FITC and anti-human CD19-PE and CD20-PE to quantify human progenitor (CD34+) and B-lineage (CD34-CD19/20+) populations. Anti-human CD3 was used to analyze human T-lineage reconstitution. Anti-human CD34-FITC and anti-human CD90-APC was used to quantitate CD34+ or CD34+CD90+ cells in culture. All antihuman antibodies were purchased from Becton Dickinson.

Retrovirus infection. The retroviral plasmids with PCL-ECO (2:1) were transfected using Lipofectamine 2000 (Invitrogen) into 293T cells. The resulting retroviral supernatant was collected 48-72 hours later and was used for infection. Target cells were resuspended in viral supernatants ($1 \times 10^5$ cells/ml) with 4 μg/ml polybrene and centrifuged at 2000 rpm for 120 min before culturing for 24 hours in RPMI-1640 medium (Sigma) plus 10% FBS and 100 U/ml penicillin/streptomycin. Cells were then resuspended in viral supernatant for another round of infection.

Live cell immunofluorescence and confocal microscopy. The LILRB2 chimeric receptor reporter cells were treated with PBS or coated monoclonal anti-LILRB2 antibody for 6 hours at 37° C. These cells were washed by PBS twice and stained with rat anti-human LILRB2 antibody for 15 minutes at 4° C. The cells were further stained with goat anti-rat Cy3 for 15 minutes at 4° C. and mounted on a slide for examination by a Zeiss LSM 710 confocal microscope. Each image was scanned in Z-series from top to bottom of cells.

3.1.2. Example 1—Results

Figure 1A:
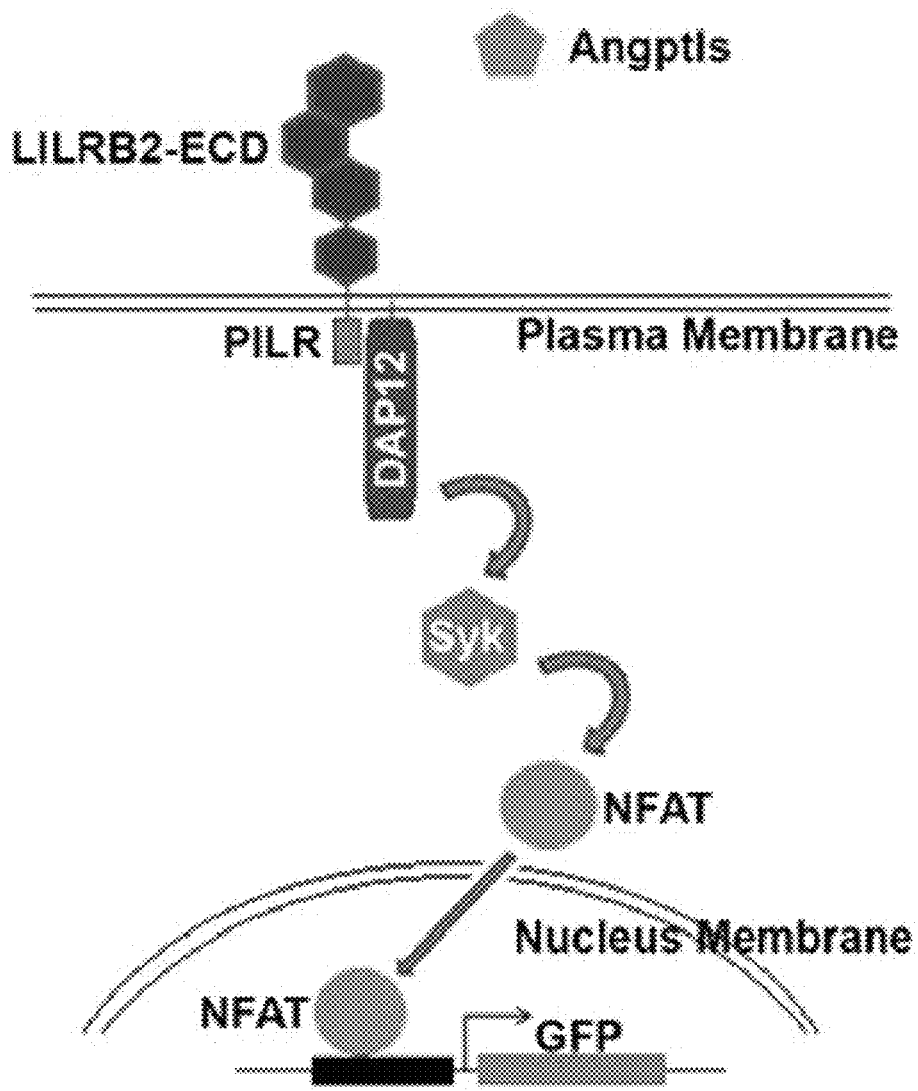
FIGS. 1A-1H. High molecular weight Angptl2 activates LILRB2 signaling.

Multimerized Angptl2 activates LILRB2. Because there is no definitive downstream reporter for LILRB-mediated signaling, a stable reporter cell system was employed to test whether Angptl2 can bind to and activate LILRB2. In this chimeric receptor reporter system, the extracellular domain (ECD) of LILRB2 is fused with transmembrane/intracellular domains of paired immunoglobulin-like receptor β (PILRβ) that associates with the adaptor protein DAP12 containing ITAM. When the chimeric receptor is activated by Angptl2 binding to the ECD of LILRB2, ZAP70 or Syk kinase is recruited to the ITAM of the adaptor DAP12 and activates the nuclear factor of activated T cells (NFAT) to promote GFP expression driven by the NFAT responsive promoter (FIG. 1A). The establishment of this reporter was inspired by a LILRB1 reporter system (Arase et al., Science. 2002; 296:1323-1326; Ohtsuka et al., Proc Natl Acad Sci USA. 2004; 101:8126-8131) and it serves as a surrogate and sensitive system to enable study of the signaling-induction abilities of different forms of Angptl2 (including soluble, immobilized, monomeric, and oligomeric) and to screen additional agonists and antagonists.

Figure 1B:
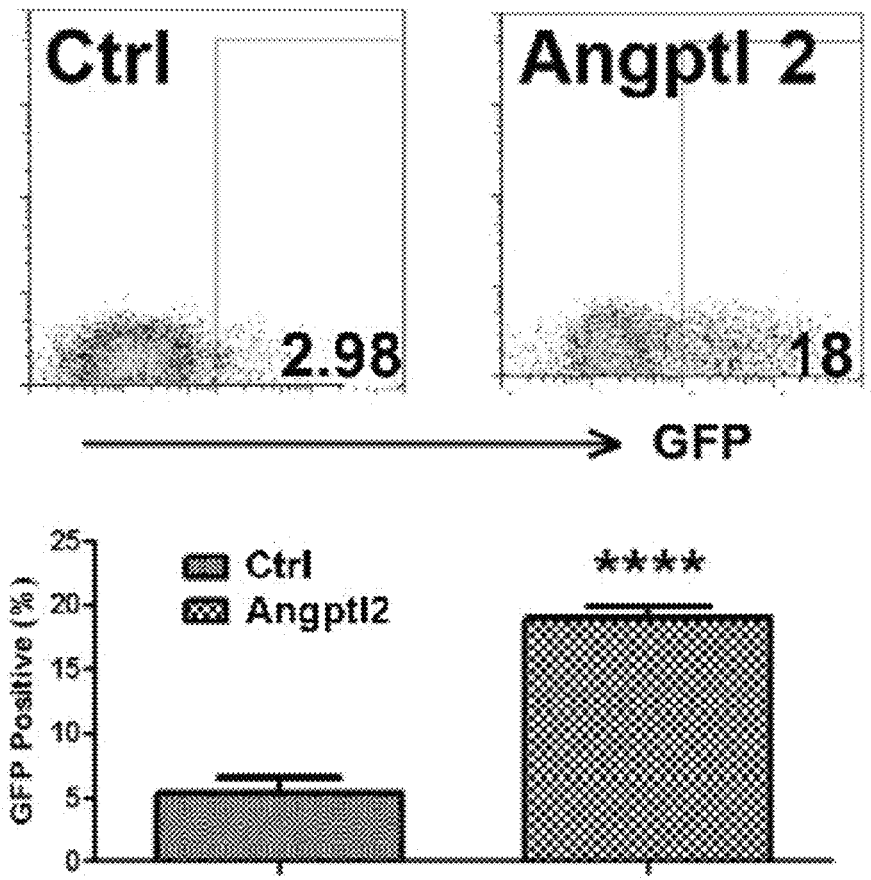
Figure 1C:
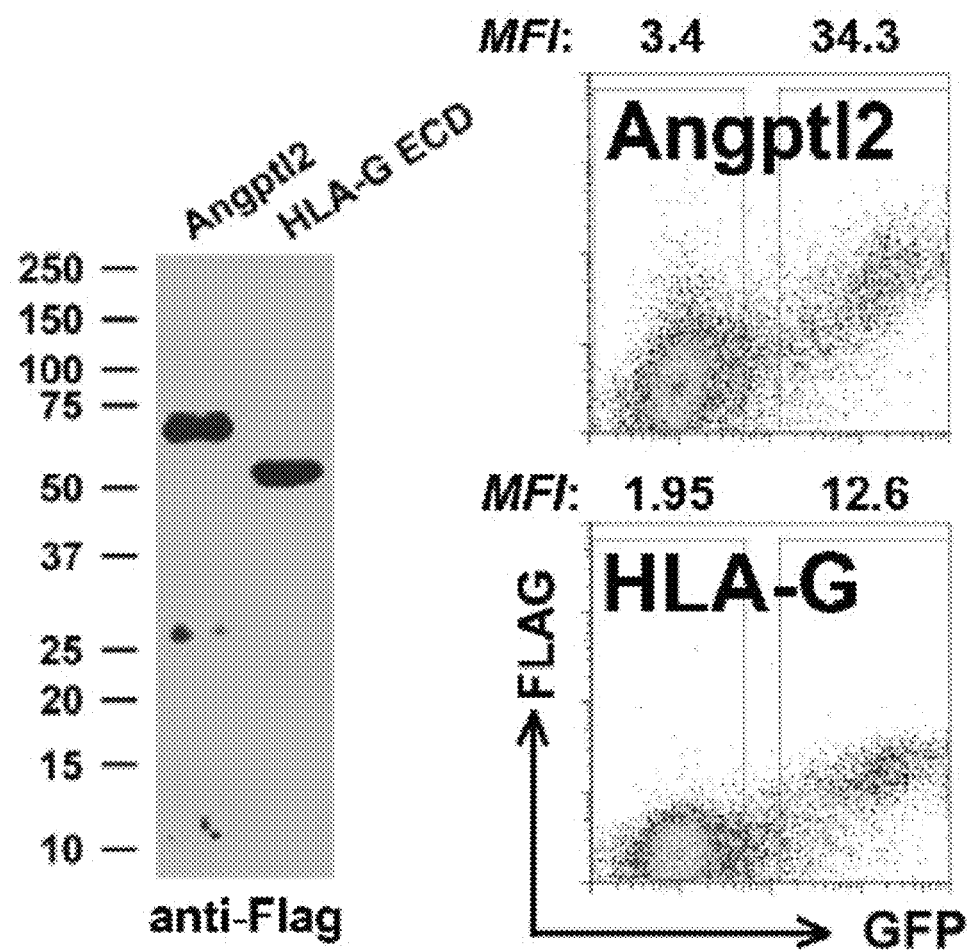
Figure 2A:
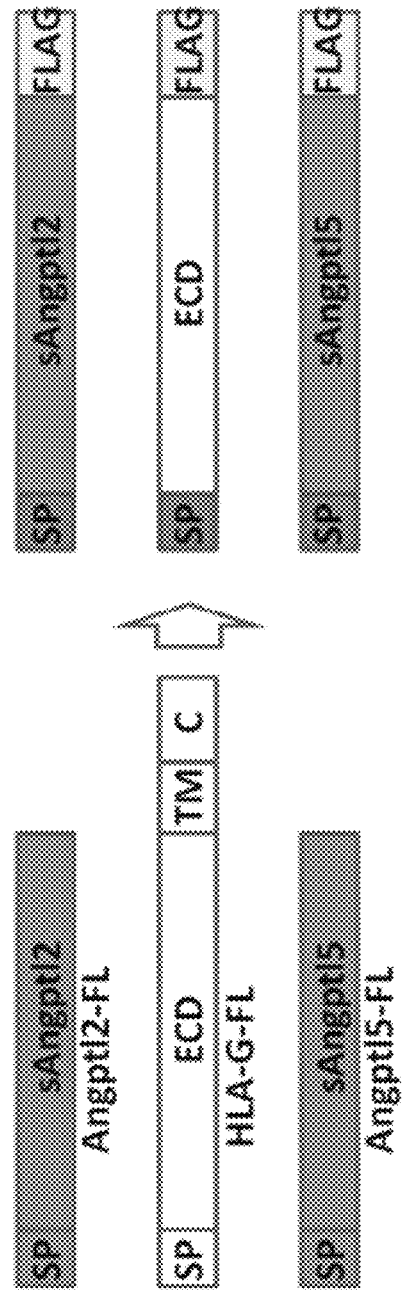
FIGS. 2A-2B. Schematic of Angptl2, Angptl5, and HLA-G extracellular domain (ECD) expression constructs.
Figure 3:
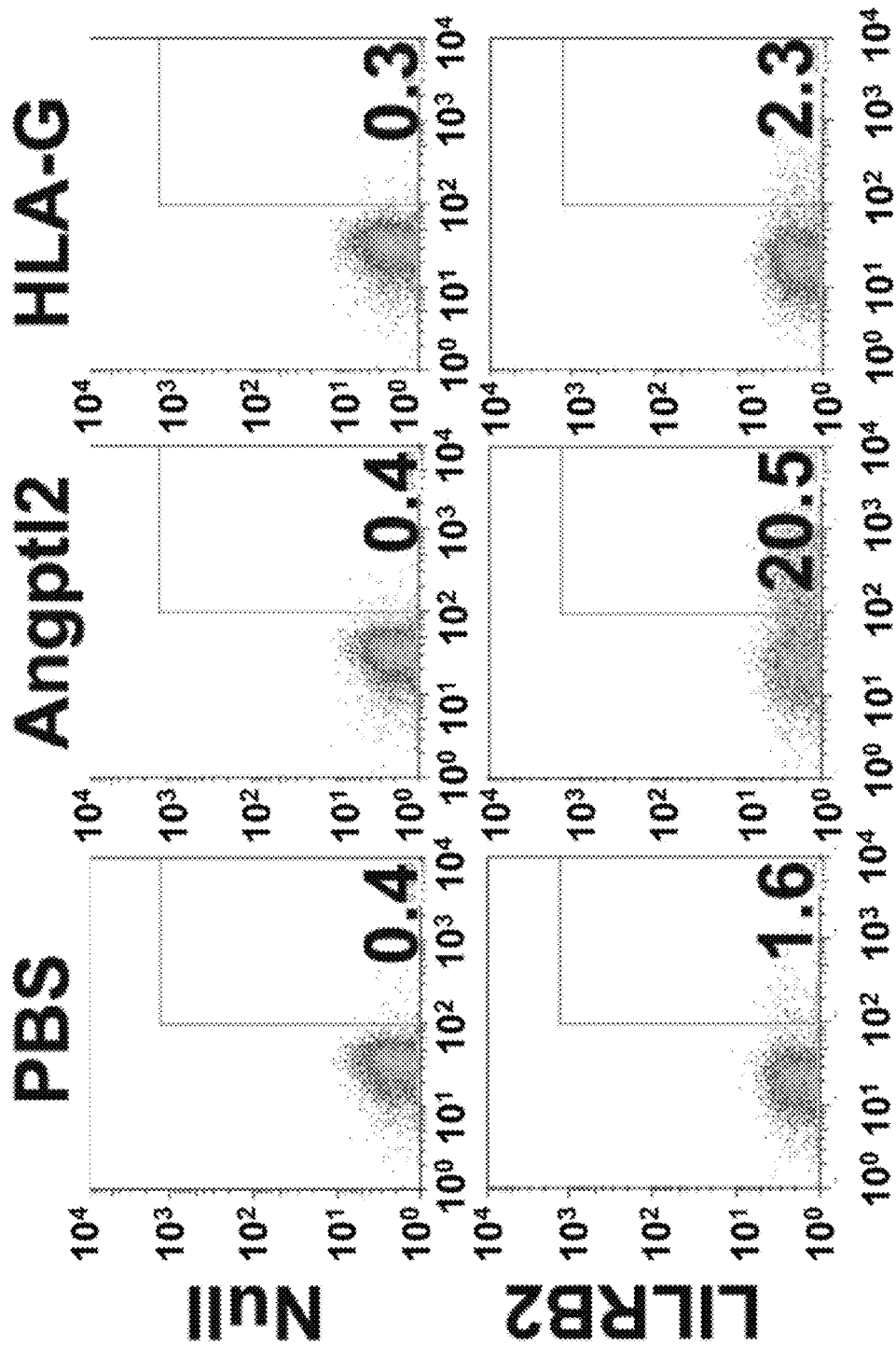
FIG. 3. Activation of the LILRB2 chimeric receptor reporter by Angptl2 is better than that by immobilized HLA-G. Chimeric LILRB2 receptor reporter cells were treated with coated 5 µg/ml GST-Angptl2 or 130 µg/ml human HLA-G for 24 hrs. Null receptor cells, which do not contain chimeric receptor, and PBS were used as controls.

To test whether Angptl2 expressed in mammalian cells can activate signaling through LILRB2, LILRB2 reporter cells were incubated with conditioned medium collected from 293T cells transfected with a plasmid designed to express Angptl2 (2 μg/ml) (schematic in FIG. 2A). Conditioned medium from mock transfected 293T cells served as the control. After 24 h, Angptl2-treated LILRB2 reporter cells induced a significantly greater GFP expression than the control cells (18.95±0.95% versus 5.34±1.19%; FIG. 1B). The potential binding/activation of LILRB2 by the immobilized HLA-G was also measured using the same LILRB2 reporter cells. GFP activation was not detected by as much as 130 μg/ml HLA-G (FIG. 3). This suggests that Angptl2 is capable of binding and activating LILRB2, with a significantly greater ability than HLAG. In parallel, the binding of Angptl2/LILRB2 to HLA-G-LILRB2 using flow cytometry analysis. To this end, a secretable HLA-G-ECD expression vector was constructed with the same signal peptide as Angptl2 expression vector (FIG. 2A) and collected the same amount of soluble HLA-G-ECD and Angptl2 for binding to LILRB2 expressed on the surface of transiently transfected 293T cells. Similar to the result of the chimeric reporter system, Angptl2 binds to LILRB2 with a significantly greater affinity than HLAG (FIG. 1C).

Figure 1D:
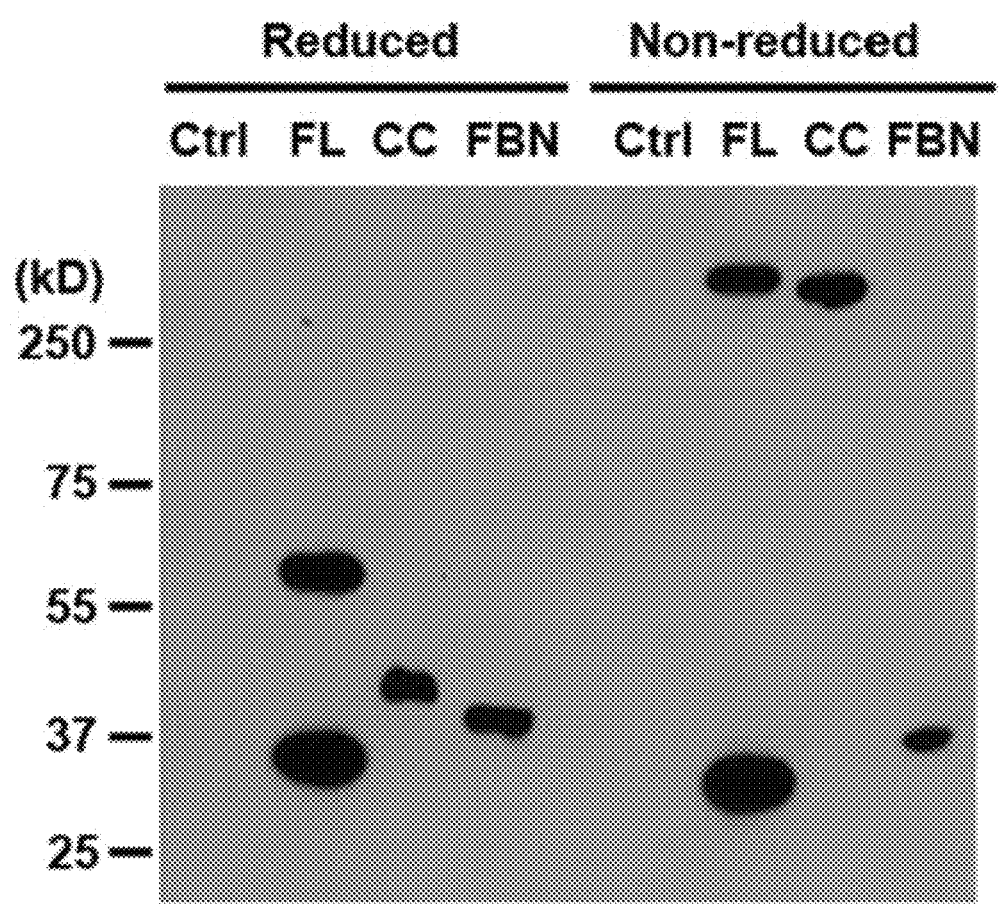
Figure 4:
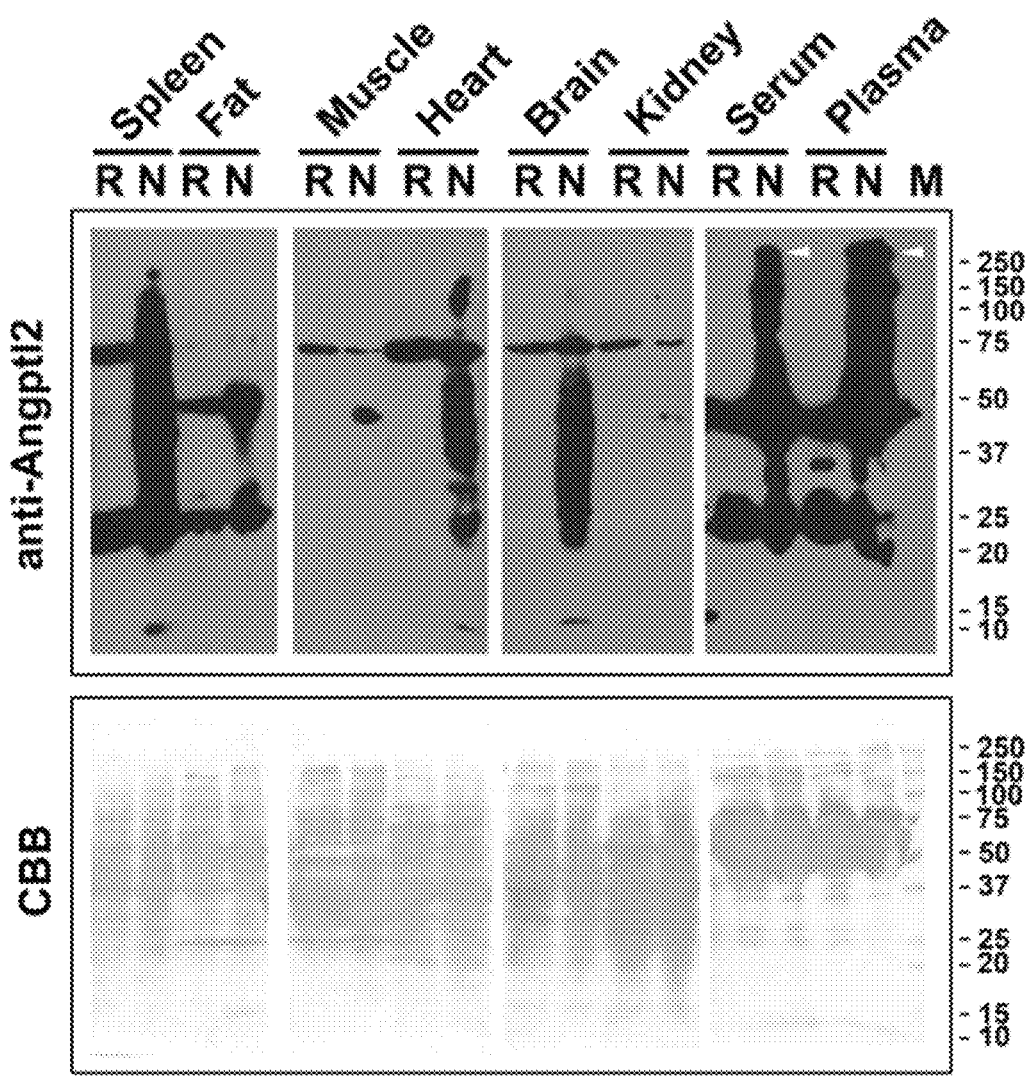
FIG. 4. Expression of mAngptl2 in mouse tissues and organs. Whole cell lysates were extracted from mouse spleen, fat, muscle, heart, brain and kidney. Plasma and serum were extracted from peripheral blood via centrifugation with or without anti-clotting reagent, respectively. Fifty µg of each sample was loaded for western blot using rat anti-mouse Angptl2 antibody. The samples loaded were visualized by Coomassie Brilliant Blue staining (CBB). R, reduced; N, non-reduced; M, molecular weight marker. Arrows indicate the multimerized mouse Angptl2.

In the described characterization of Angptl2 expressed in 293T cells, full-length (FL), coiled-coil domain (CC), and FBN-like domain of Angptl2 with or without β-mercaptoethanol (BME) treatment were compared. BME treatment reduces disulfide bonds that stabilize a HMW form of Angptl2. When analyzed by SDS-PAGE, full-length and CC domain preparations of Angptl2 ran partially or exclusively, respectively, as a HMW band (larger than 250 kD), whereas the FBN domain migrated as a 37 kD band, corresponding to the expected size of the FBN monomer (FIG. 1D). The HMW species was likely in a multimerization state. Similarly, multimerized Angptl2 exists in mouse serum and plasma (FIG. 4).

Figure 1E:
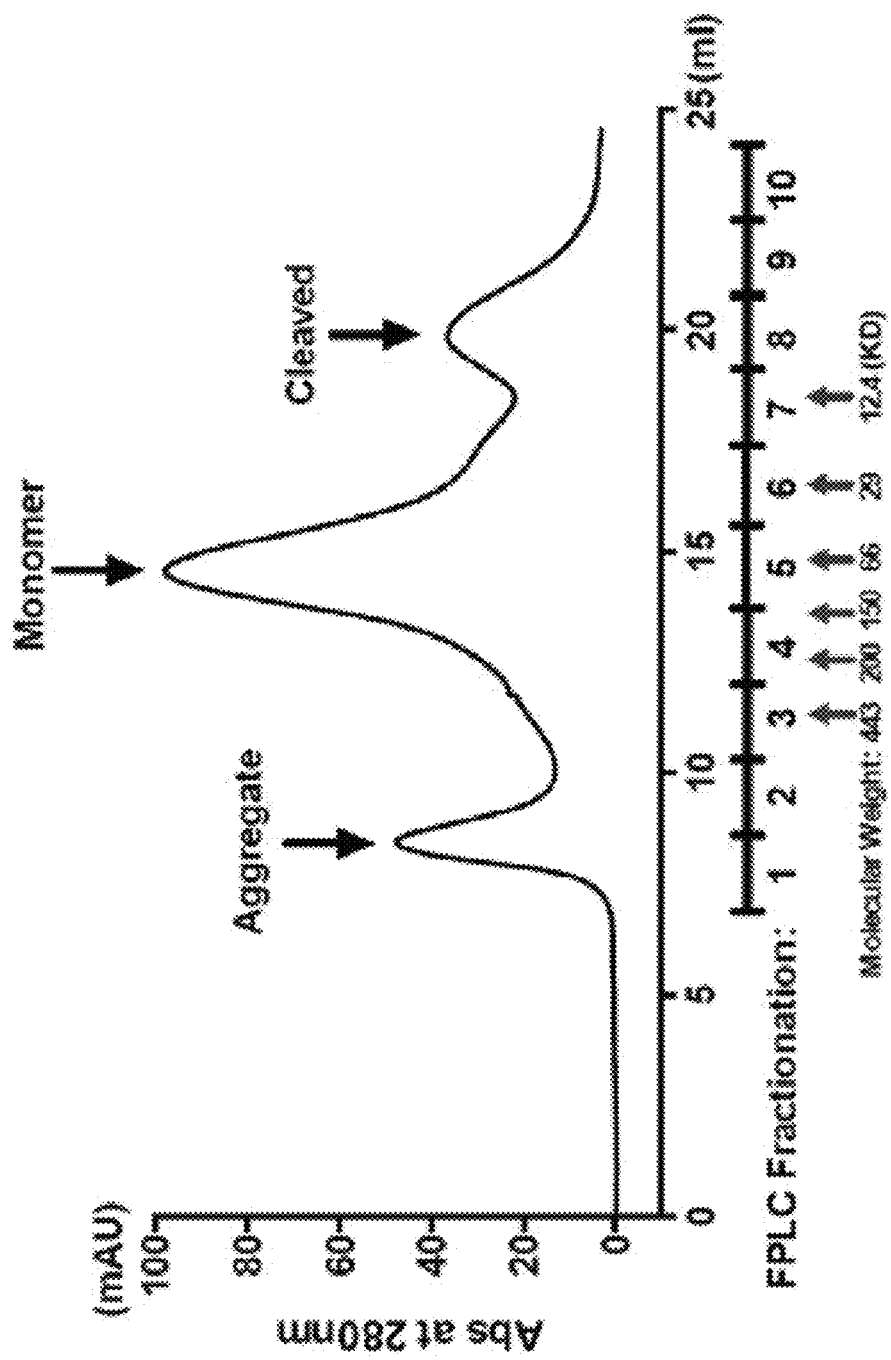
Figure 1F:
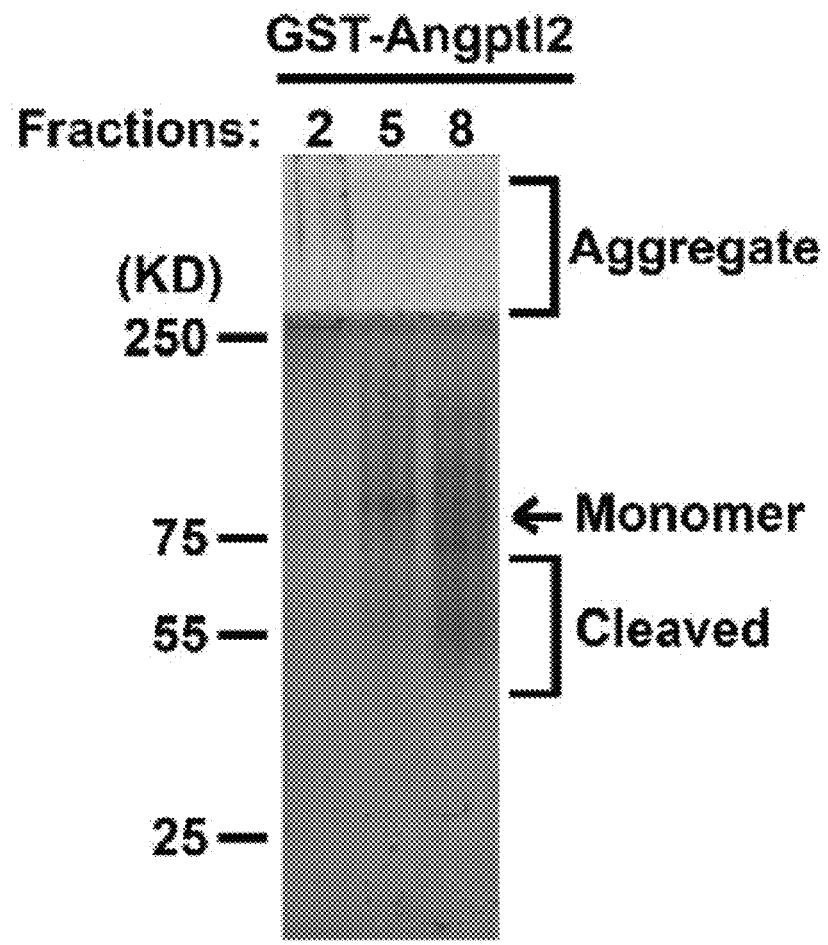
Figure 1G:
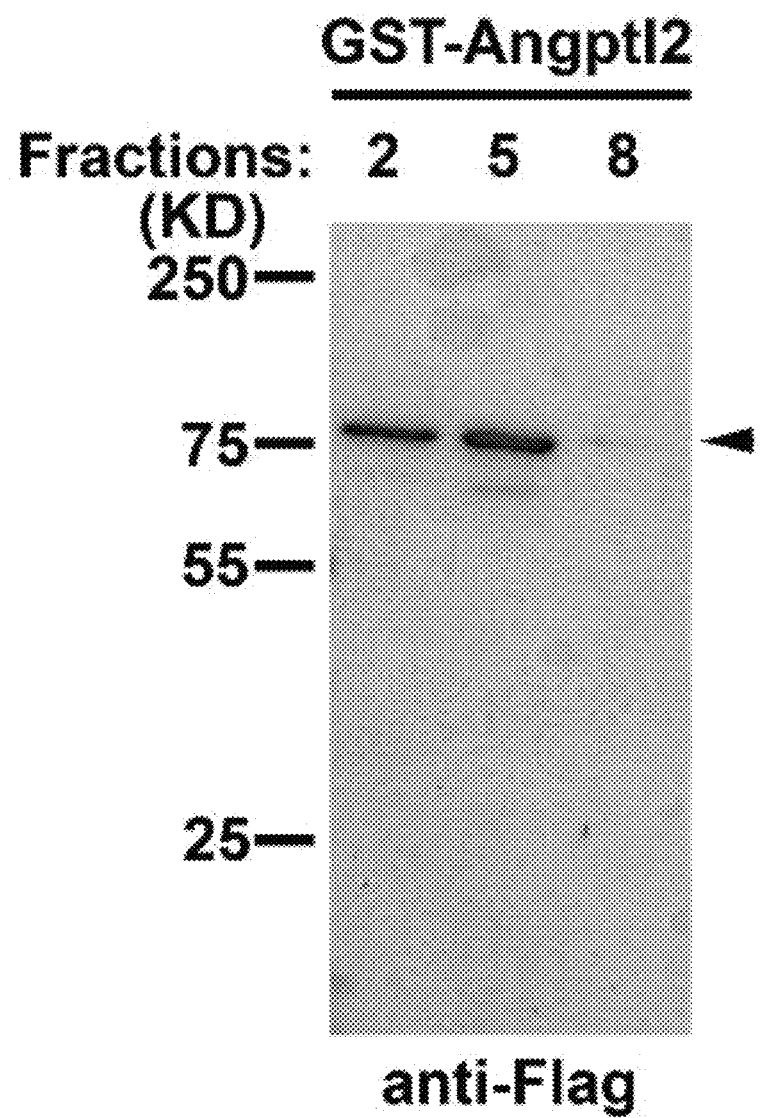
Figure 1H:
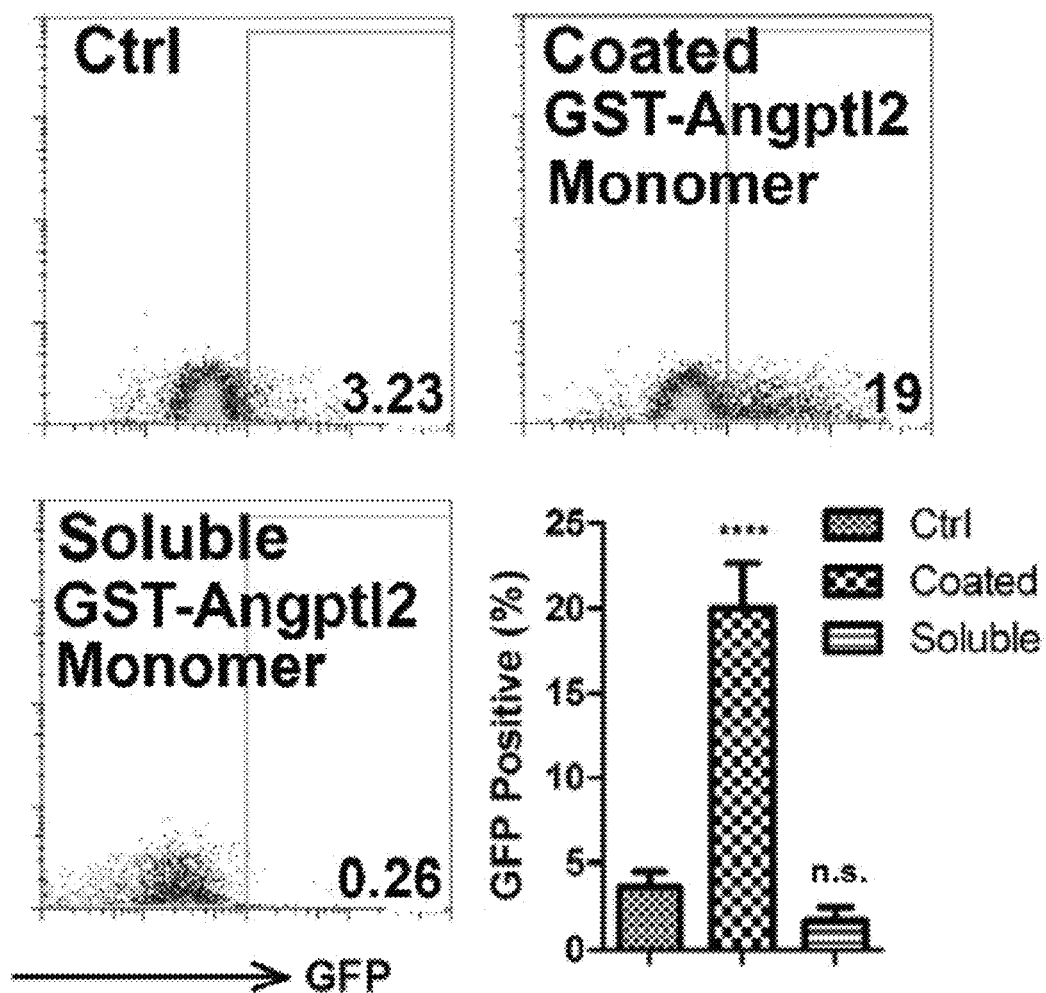

A bacterial expression system enabled production and purification of a large amount of GST-tagged Angptl2 (Zheng et al. Nature. 2012; 485:656-660). The monomer GST-Angptl2 was purified by size exclusion chromatography and the product was detected in native-PAGE and western blotting (FIGS. 1E-1G). Because the multimerized ligand can induce the clustering of surface receptor (Arase et al., Science. 2002; 296:1323-1326; Ohtsuka et al., Proc Natl Acad Sci USA. 2004; 101:8126-8131) and immobilized ligand may also cluster the receptor, the abilities of the soluble and immobilized monomeric GST-Angptl2 to activate the LILRB2 reporter cells were compared. The monomeric GST-Angptl2 was immobilized on the wells of the tissue culture plate or added into the medium, and LILRB2 reporter cells were added. Only the immobilized monomeric form, and not the soluble monomer, induced GFP expression (20±2.65% versus 3.56±0.98%; FIG. 1H). Because the natively multimerized form of Angptl2 and the immobilized monomer Angptl2 activated LILRB2 but the soluble monomeric Angptl2 did not, it was concluded that Angptl2 must be multimerized to become an active ligand of LILRB2.

Figure 5A:
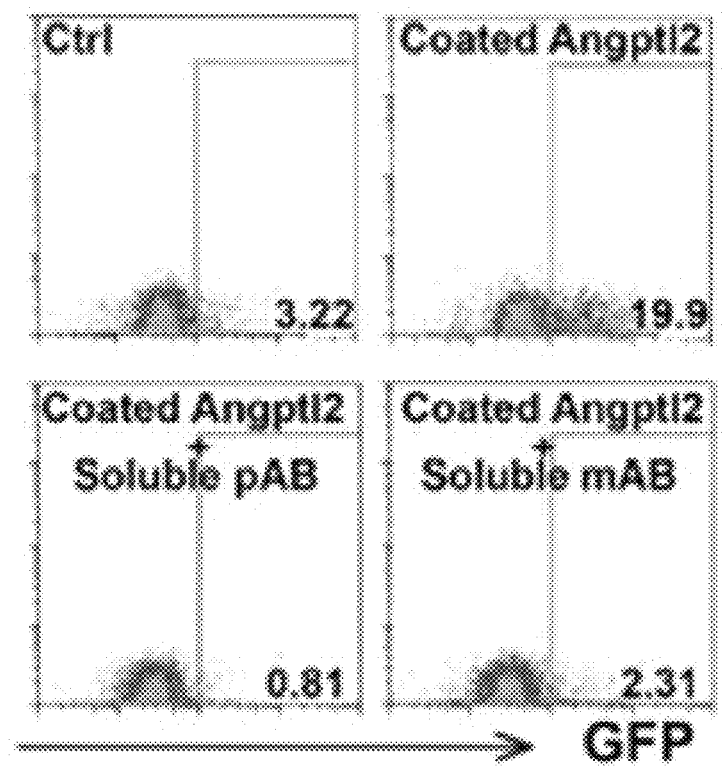
FIGS. 5A-5D. Immobilized anti-LILRB2 antibodies activated the chimeric LILRB2 reporter.
Figure 5B:
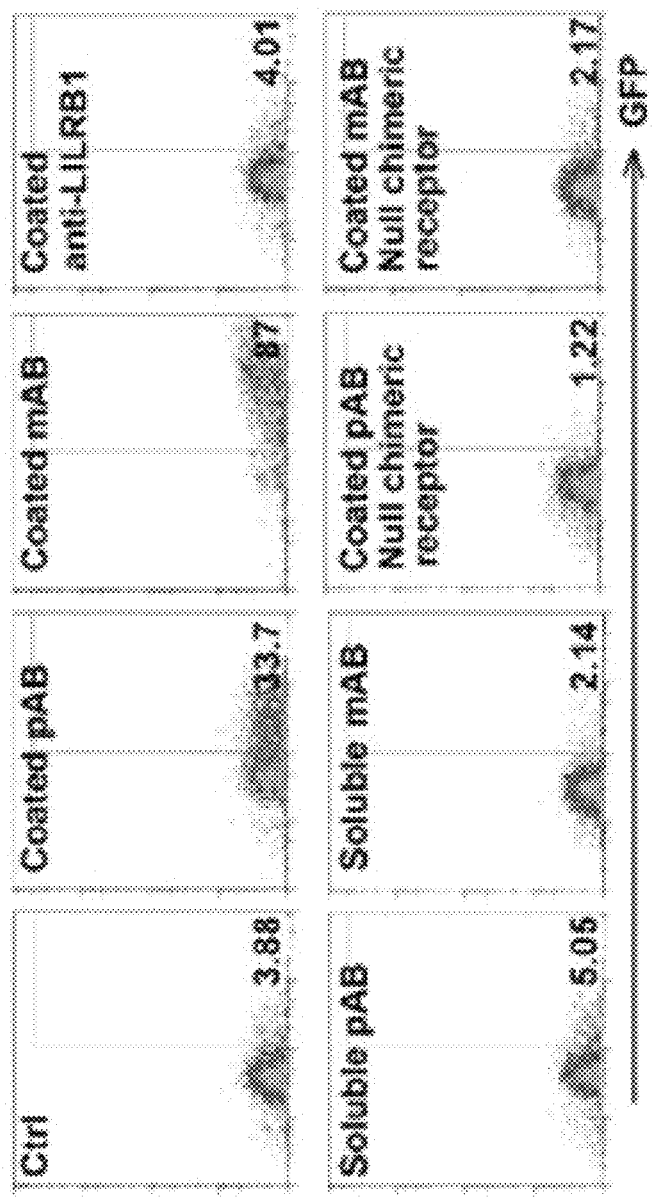
Figure 5C:
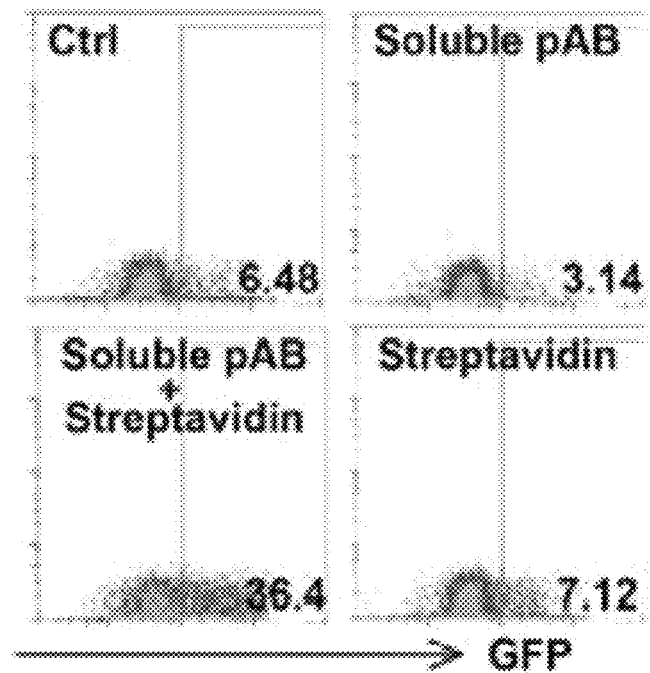
Figure 5D:
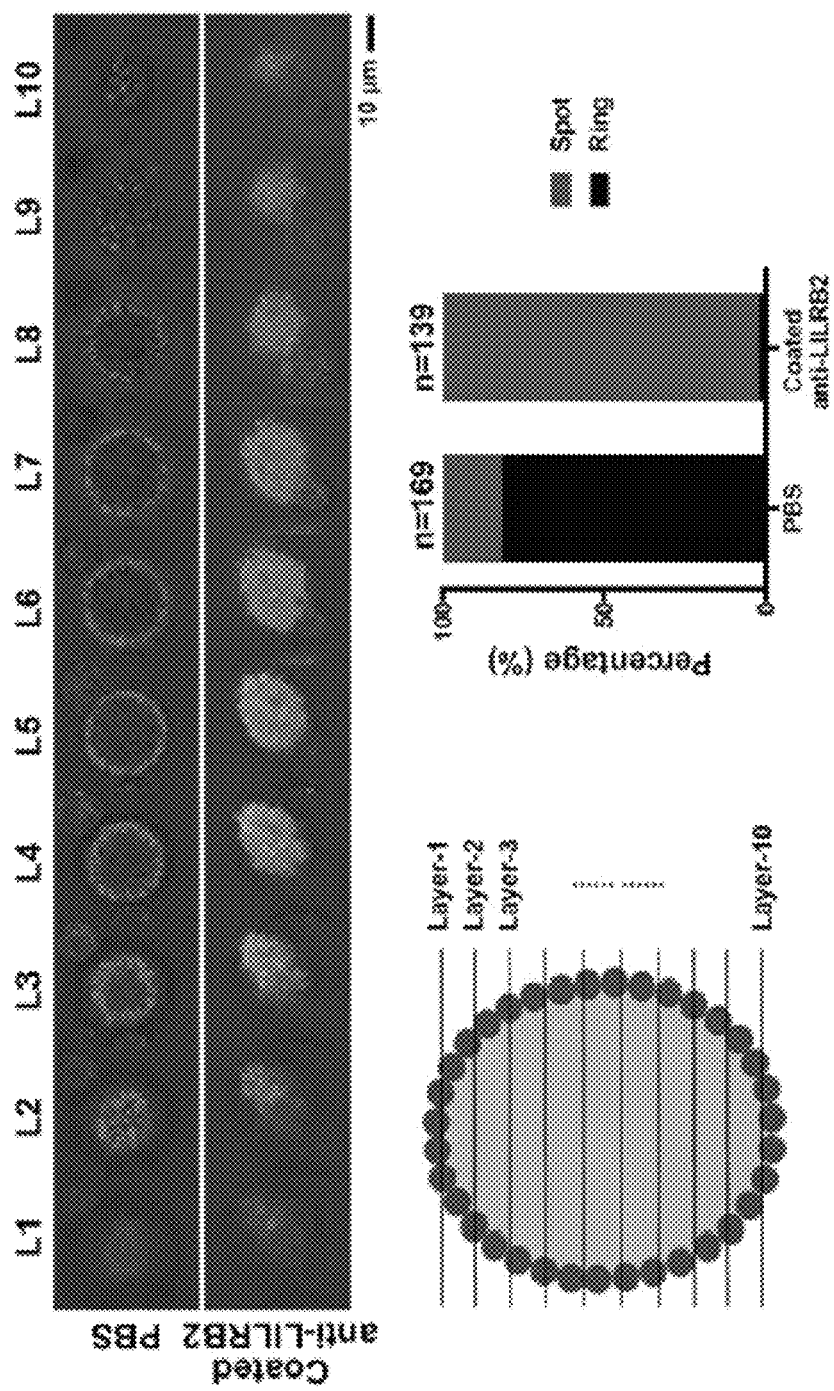

To further study whether a multimerized form of Angptl2 is needed to activate LILRB2, the effects of monoclonal and polyclonal anti-LILRB2 antibodies on the LILRB2 reporter cells were tested. Both soluble monoclonal and polyclonal anti-LILRB2 blocked the activation of LILRB2 by the immobilized Angptl2 (from 19.9% to 0.81 or 2.31%; FIG. 5A), supporting the idea that the binding between Angptl2 and LILRB2 is not as potent as that between anti-LILRB2 and LILRB2. Whereas neither the control antibody nor the soluble anti-LILRB2 stimulated GFP expression, both immobilized monoclonal and polyclonal anti-LILRB2 efficiently induced upregulation of GFP (from 3.88% to 33.7 or 87%; FIG. 5B). Moreover, cross-linking of biotin-conjugated anti-LILRB2 by streptavidin activated GFP expression (from 3.1% to 36.4%; FIG. 5C). Although anti-LILRB2 has a higher binding affinity for LILRB2 than does Angptl2, only immobilized but not soluble antibodies activated LILRB2. To determine if immobilized ligands induce receptor clustering, the LILRB2 localization on the cell surface with or without immobilized monoclonal anti-LILRB2 treatment was examined. Without treatment, the majority of LILRB2 chimeric reporter cells (81.2%) exhibited an even distribution of LILRB2-ECD on the cell membrane, with a "Ring"-like shape under confocal microscopy observation (FIG. 5D). By contrast, after treatment with immobilized antibodies, the distribution of LILRB2-ECD was changed from the "Ring"-to the "Spot"-like shape in 97.8% signaling activated cells (indicated as GFP induced cells) (FIG. 5D). These results further support the conclusion that multimerized ligands induce the clustering of the receptor LILRB2 for signaling activation.

Figure 6A:
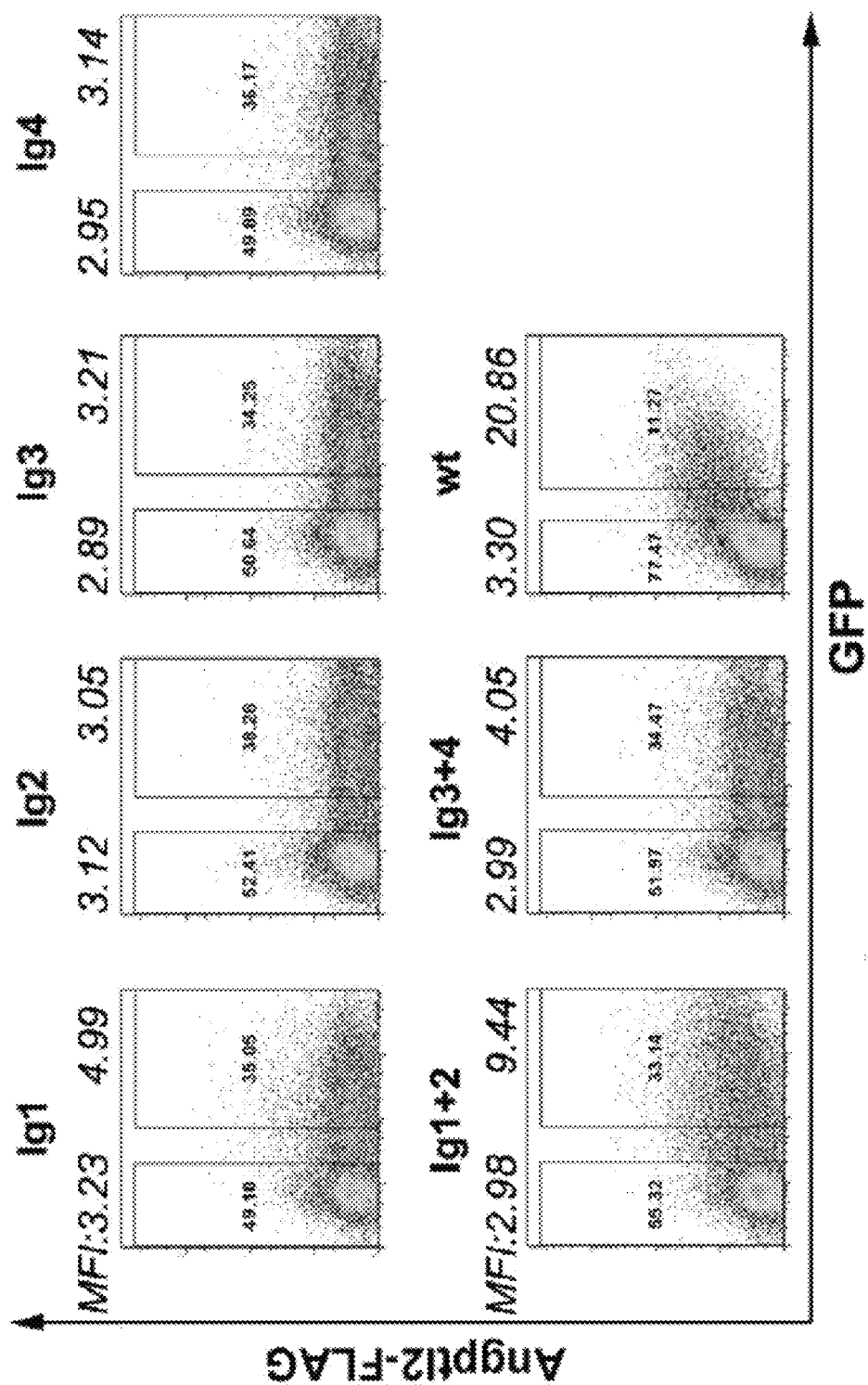
FIGS. 6A-6I. Ig domains 1 and 4 in LILRB2 are critical for Angptl2 binding and signal activation.
Figure 6B:
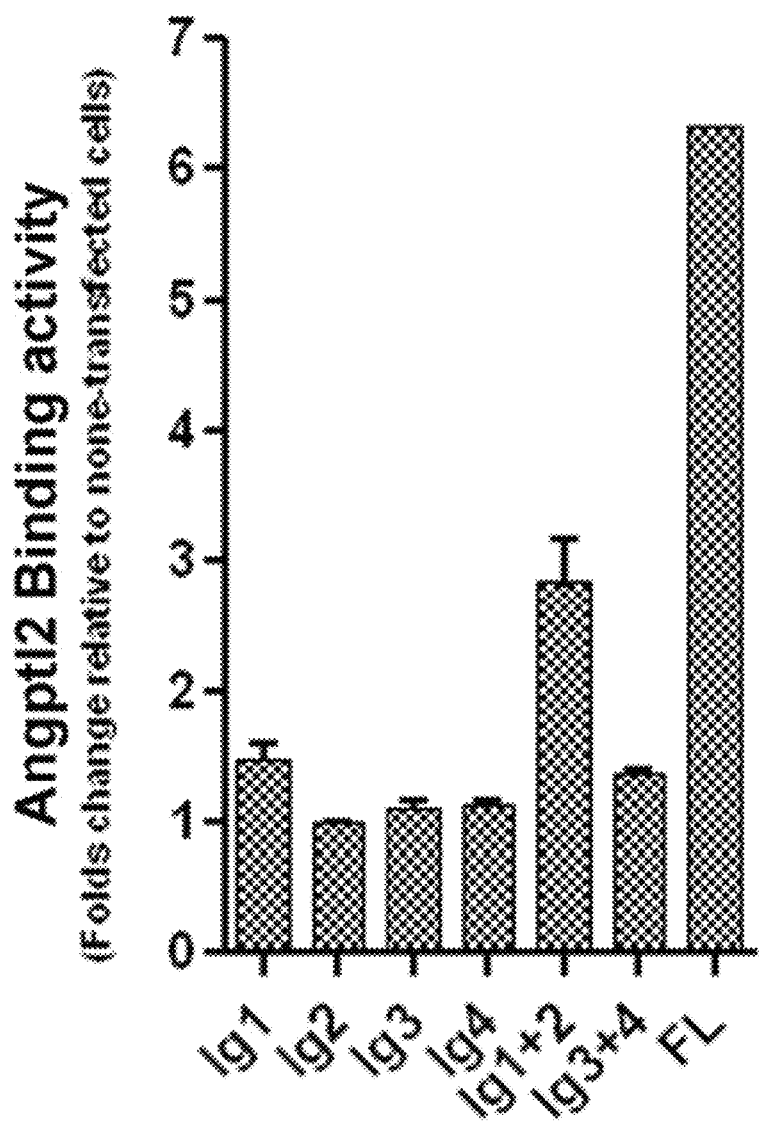
Figure 7:
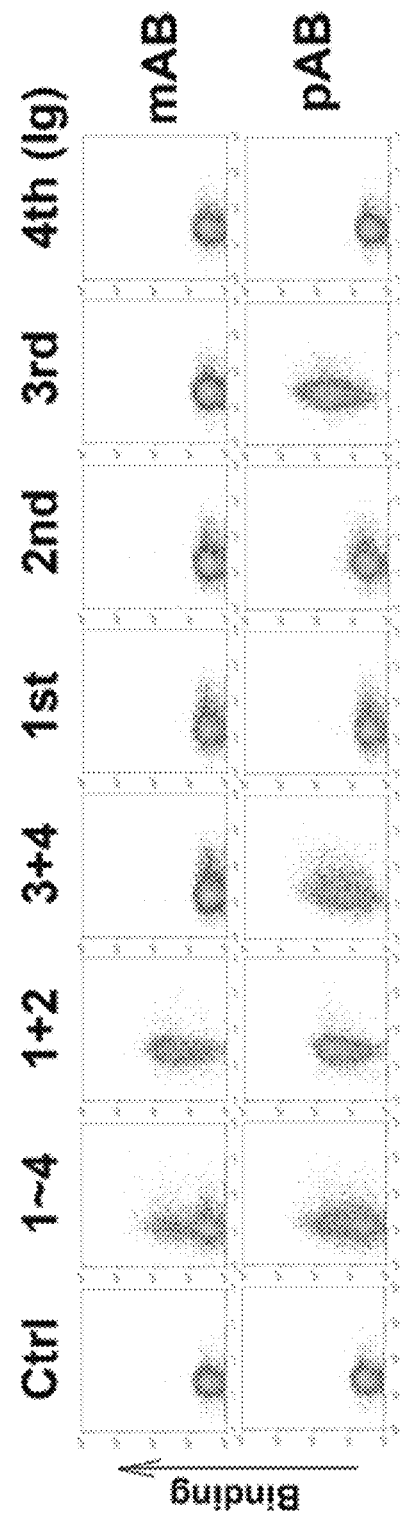
FIG. 7. Interaction of LILRB2 Ig domains with anti-LILRB2 antibodies. Mouse T hybridoma cells were infected with full-length LILRB4 ECD (1-4), individual Ig domains (1st, 2nd, 3rd and 4th Ig domain) and two-Ig domain combinations (1+2 and 3+4). The empty vector was used as negative control. These cells were stained by monoclonal (mAB) or polyclonal (pAB) anti-LILRB2 antibody for flow cytometry analysis.

A motif in Ig domains of LILRB2 is critical for the effects of Angptl2 in binding and receptor activation. LILRB2 contains four extracellular immunoglobulin (Ig)-like domains. Takai et al., J Biomed Biotechnol. 2011; 2011: 275302. It was hypothesized that one or more of these Ig-domains bind to Angptl2. To test this hypothesis, a number of domain and site-specific mutations of LILRB2 were generated for the flow cytometry-based cell surface ligand binding assay and chimeric reporter assay. To start with, Angptl2 binding abilities of a number of domain mutations of LILRB2 were screened. Although individual Ig domains of LILRB2 do not bind to Angptl2, Ig1 and 2 in combination, and Ig3 and Ig4 in combination displayed about 50% and 10%, respectively, of the maximal binding between the full-length LILRB2 and Angptl2 (FIGS. 6A-6B, FIG. 7). This suggests that the major Angptl2 binding site resides in Ig1 and Ig2 of LILRB2 and that Ig3 and Ig4 facilitate binding of C-terminal domains of the protein.

Figures 8B, 8C:
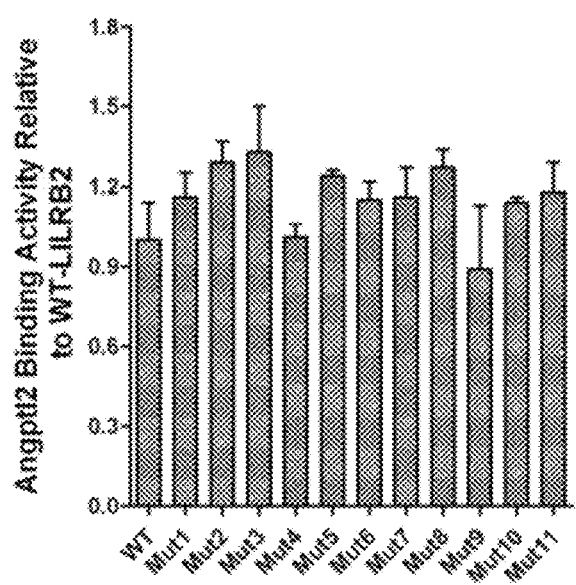

Next a series of site-specific mutations in amino acids potentially critical to the binding of ligand to LILRB2 based on the structure of LILRB2 28 (PDB structure 2GY7) were designed. Based on the physical mapping data of LILRB2, both Ig1-Ig2 and Ig3-Ig4 combination can maintain its binding activity with Angptl2, which indicates that the single interface on each Ig domain is not essential for LILRB2 binding affinity. For this type of Ig structure, the binding interface is possibly located at flexible and variable loops rather than rigid and conserved beta-sheets. Based on the PDB structure of Ig1-Ig2 domain (PDBID: 2GW5 and 2DYP) and Ig3-Ig4 domain (PDBID: 4LLA), the possible interface on each Ig domain was designed (FIGS. 8A-8C). Because the overall geometry of four Ig domains is highly flexible and each one of it is not essential, the point mutation on each Ig domain may not block the overall binding between LILRB2 and Angptl2. Therefore, some additional large and hydrophobic residues were identified for mutagenesis study (FIGS. 8A-8B). However, these mutant LILRB2 do not significantly decrease Angptl2 binding (FIG. 8C). These results suggest that Angptl2 may have somewhat different binding pockets in LILRB2 than HLA-G (see below for additional data).

Figure 6C:
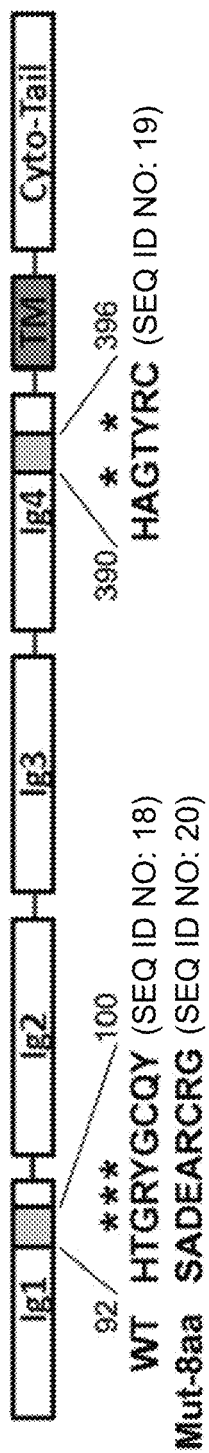
Figure 6D:
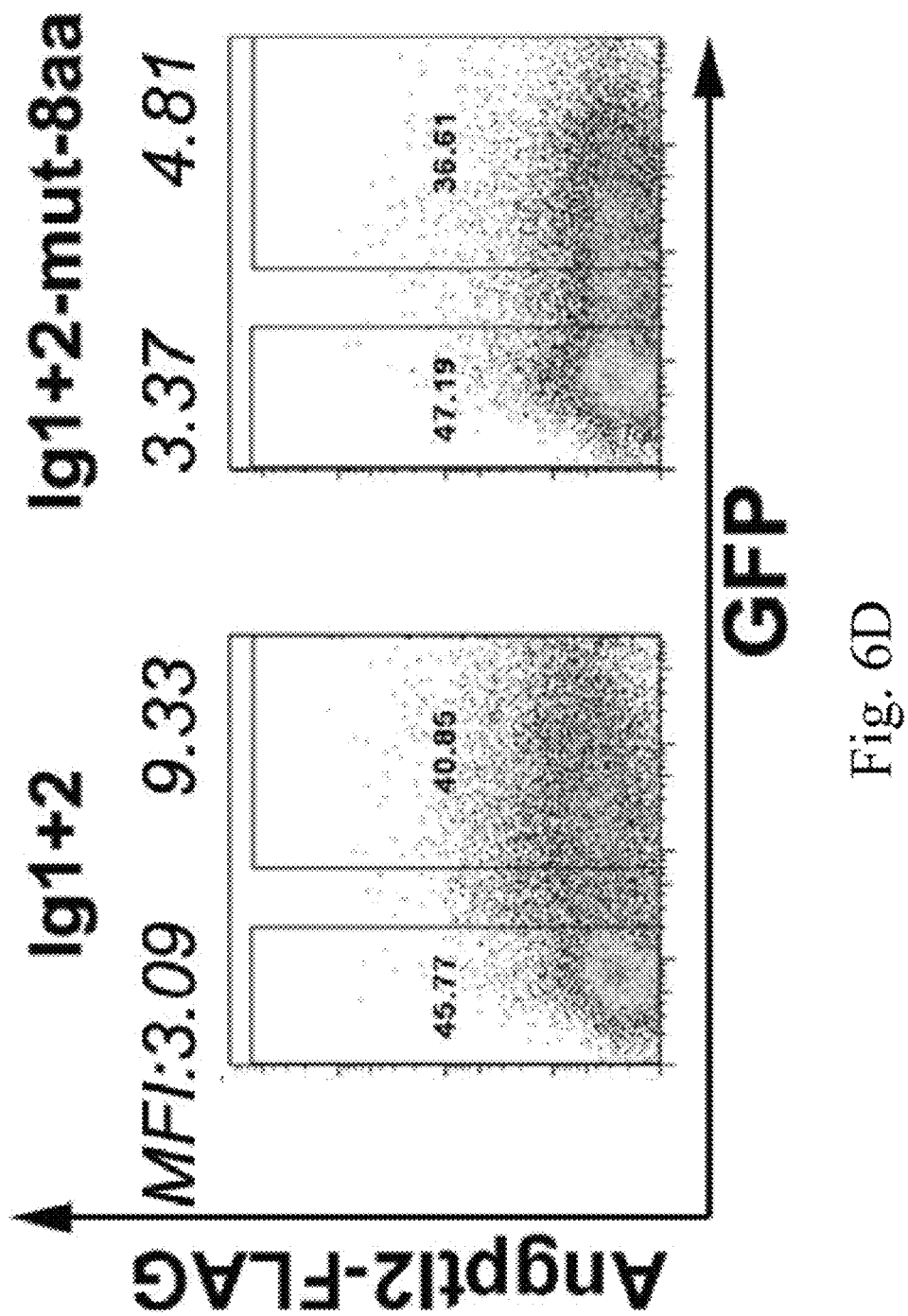
Figure 6E:
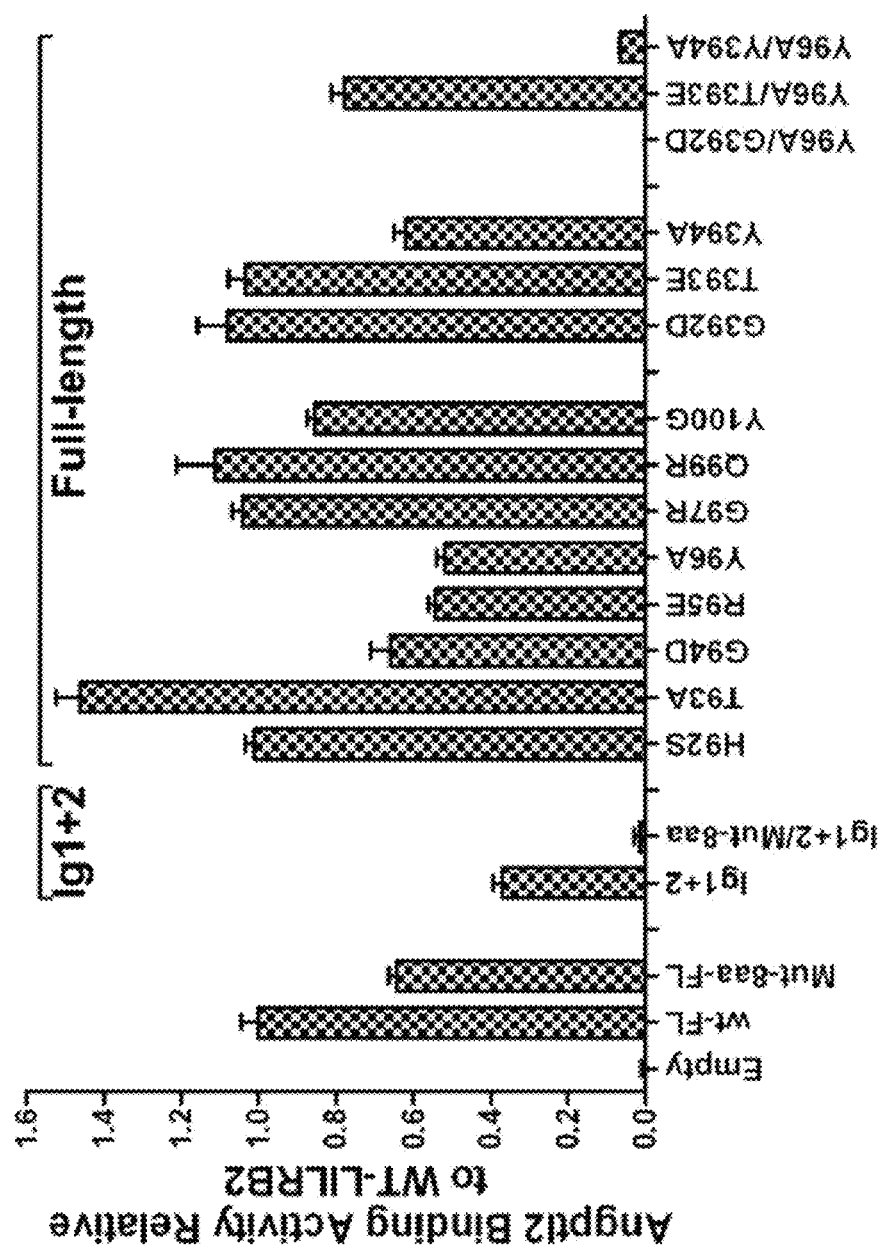
Figure 6F:
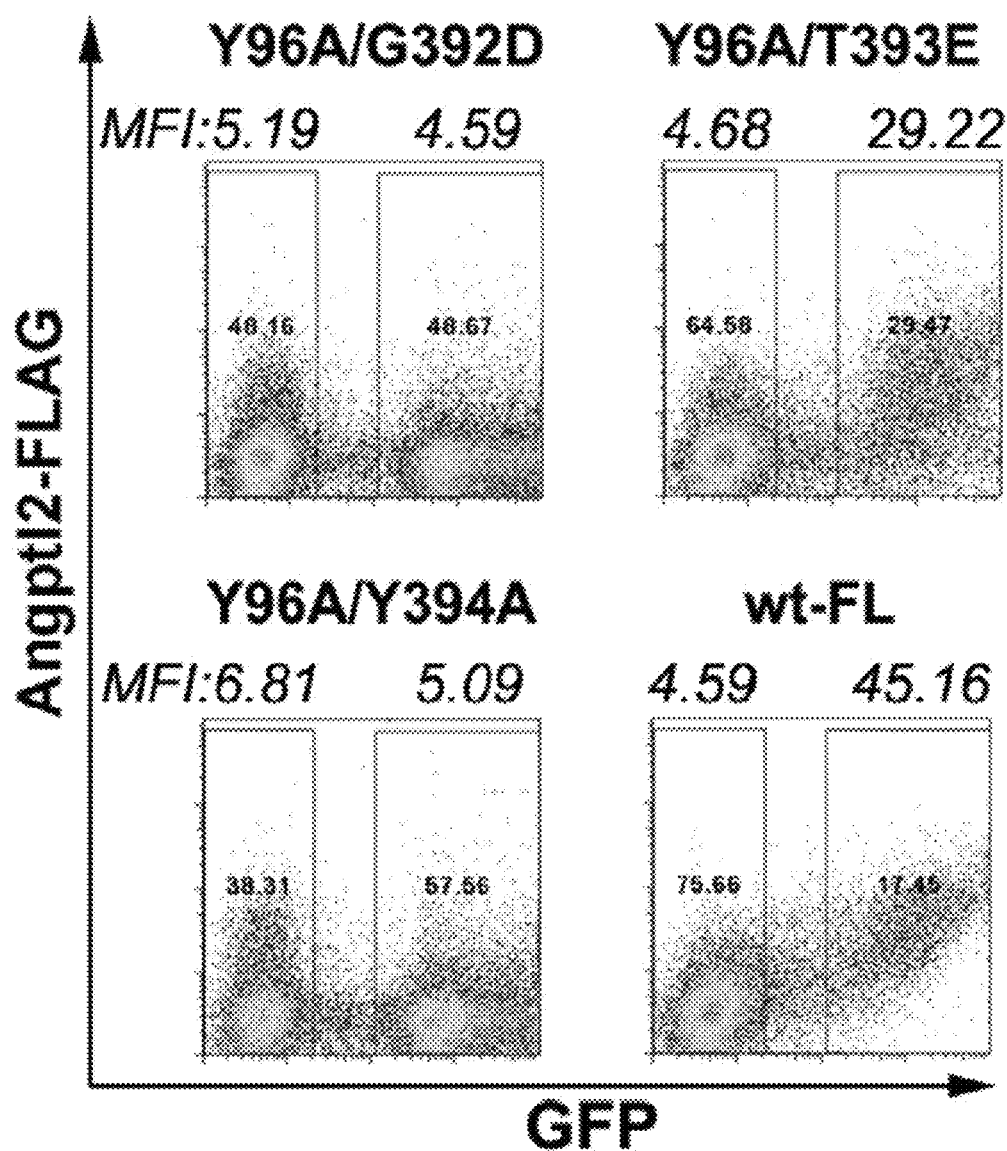

The bioinformatical analysis and mutagenesis study results were combined to find that AA 92-100 in Ig1 is critical for Angptl2 binding. The Ig1+2 fragment with mutations in this region (Mut-8 aa, SEQ ID NO: 20) did not bind to Angptl2, and Angptl2 binding of the full-length LILRB2 with the same mutation was decreased by more than 50% relative to the wild-type protein (FIGS. 6C-6D). Further experiments showed that single mutations in G94, R95, or Y96 each decreased the Angptl2 binding of full-length LILRB2 by half (FIG. 6E), indicating these three amino acids are essential for Angptl2 binding in Ig1. A similar motif, AA 390-396, exists in Ig4 (FIG. 6C, SEQ ID NO: 19). A single mutation in Y394 decreased Angptl2 binding of full-length LILRB2 by about 30% (FIG. 6E). Furthermore, when combined with Y96A, G392D or Y394A mutations totally abrogated the Angptl2 binding of full-length LILRB2 (FIGS. 6E-6F). Therefore, these results indicate that Ig2 helps Ig1 to form the major Angptl2 binding site, Ig4 further facilitates Ig1+2 binding, and the H*G*Y*C motifs in Ig1 (SEQ ID NO: 18) and Ig4 (SEQ ID NO: 19) are critical for LILRB2 to bind Angptl2.

Figure 2B:
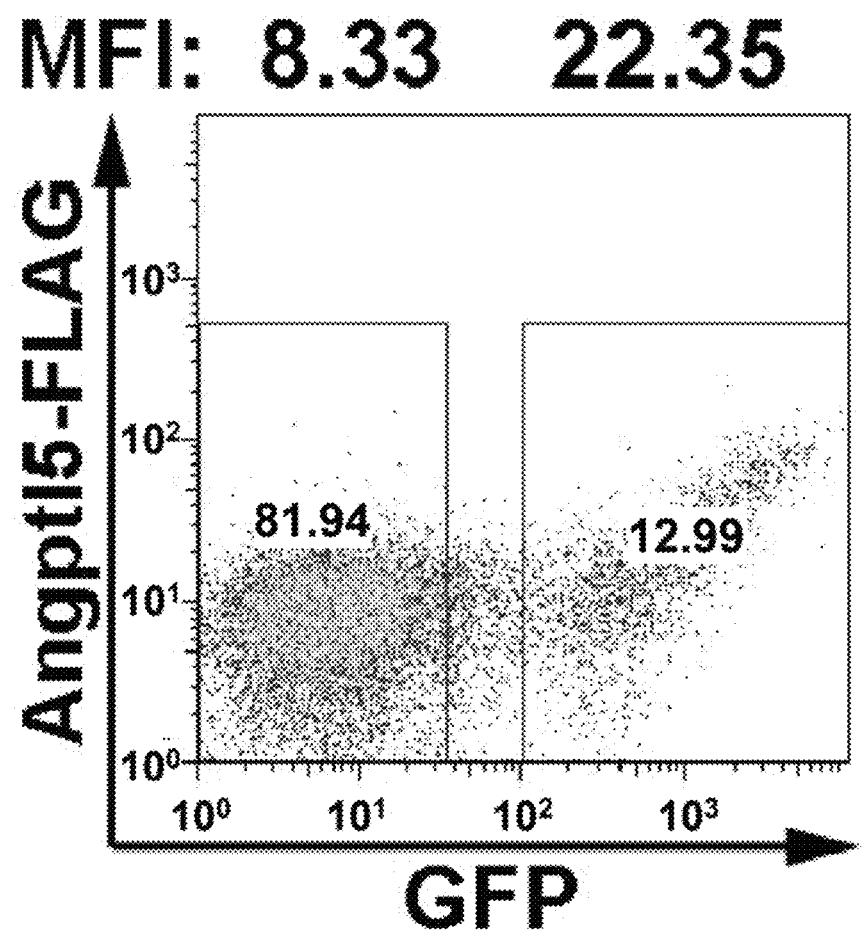
Figure 6G:
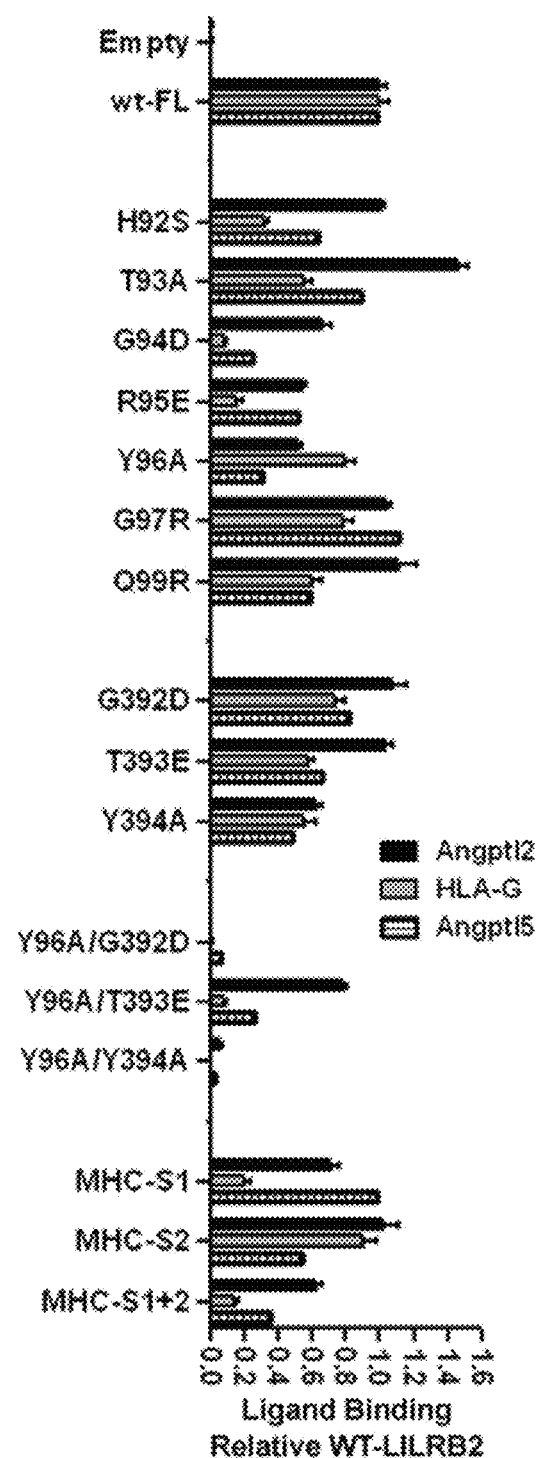

To further investigate whether Angptl2, Angptl5, and HLA-G bind to the same regions in LILRB2, the bindings of these ligands to mutant LILRB2 were compared. HLA-G binds to a number of mutant LILRB2 including H92S, T93A, G94D, R95E, Q99R, G392D, T393E, and HLA-G binding site 1 (MHC-S1) (from the structures by Shiroishi et al., Proc Natl Acad Sci USA. 2006; 103:16412-16417; Shiroishi et al., Proc Natl Acad Sci USA. 2003; 100:8856-8861) with lower affinity than Angptl2. Angptl5 binds to mutant LILRB2 generally more similar to Angptl2 than to HLA-G (FIG. 6G, FIG. 2B). Together with the result in FIG. 8C, the data suggest that the binding of Angptl2 or HLA-G to LILRB2 is partially but not completely overlapped.

Figures 6H, 6I:
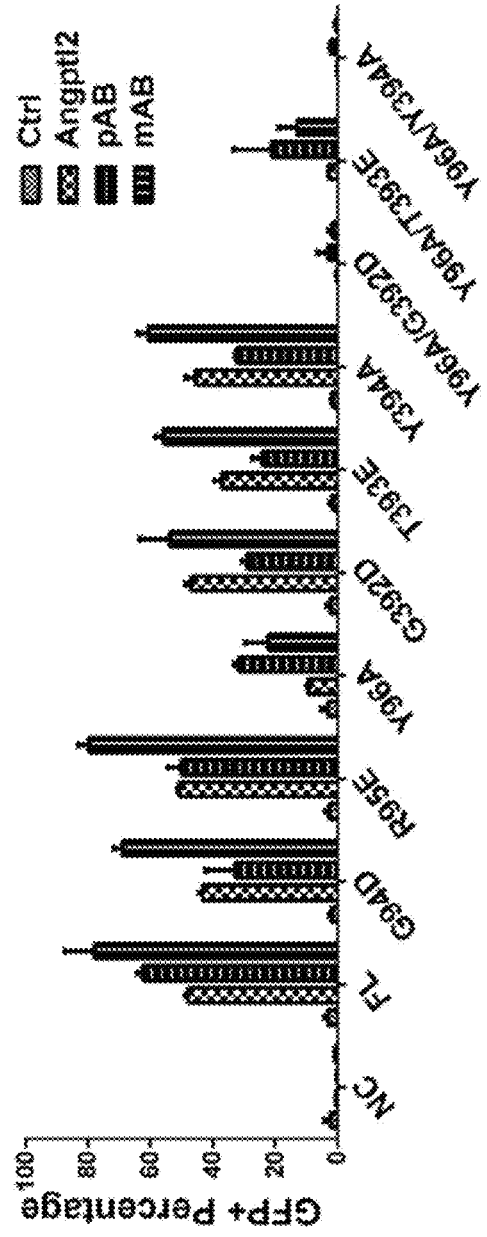

In addition to the flow cytometry-based binding analysis, the activation of various LILRB2 mutants treated with immobilized antibodies or Angptl2 in the chimeric reporter system was measured. It was found that only Ig1 and Ig2 domains in combination could bind and be activated by ligands (FIG. 6H). Moreover, a single mutation in Y96 led to a dramatic decrease of GFP induction, and the combined mutations of Y96A with either G392D or Y394A totally abrogated the GFP induction by immobilized Angptl2 (FIG. 6I). Therefore the results in using chimeric reporter system confirmed that the H*G*Y*C motifs in Ig1 (SEQ ID NO: 18) and Ig4 (SEQ ID NO: 19) are essential for LILRB2 to bind Angptl2. Furthermore, they suggest that the indicated motifs are critical for LILRB2 activation.

Figure 9:
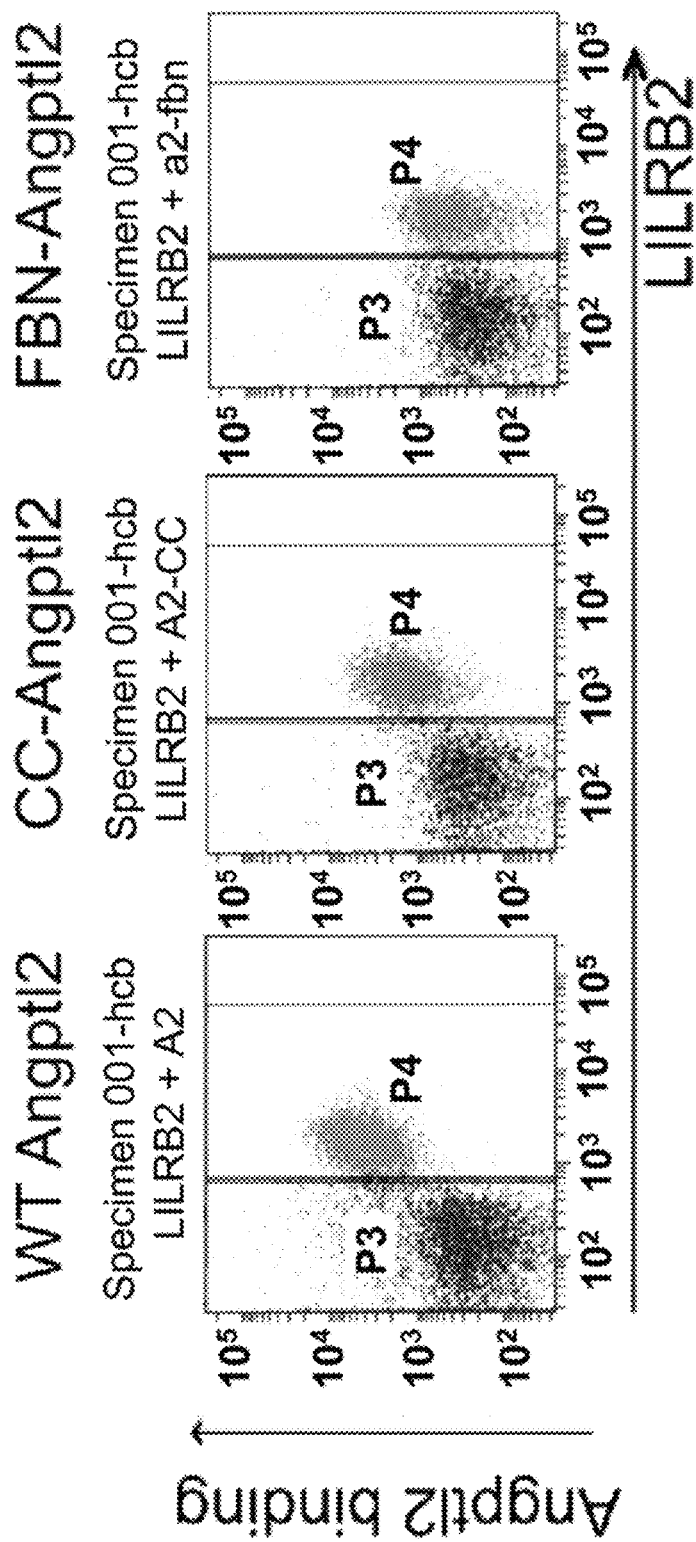
FIG. 9. The FL but not FBN domain of Angptl2binds to the human cord blood (CB) LILRB2+ cells as determined by flow cytometry analysis. Human CB mononuclear cells were incubated with indicated FLAG-tagged full-length, CC domain, or FBN domain of Angptl2 followed by staining with anti-FLAGAPC and anti-human LILRB2-PE in a flow cytometry analysis.
Figure 10:
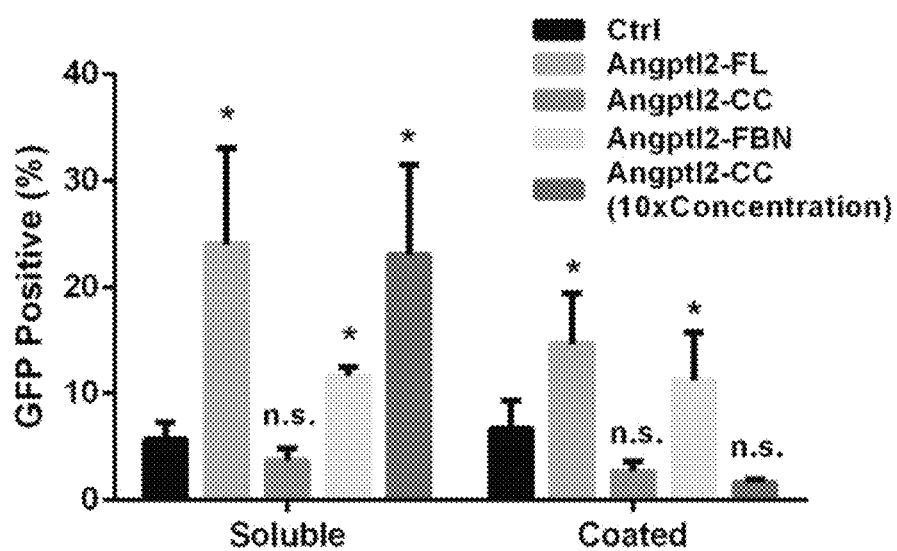
FIG. 10. The activation of the LILRB2 chimeric receptor reporter by soluble or immobilized full-length, CC domain, or FBN domain of Angptl2. Chimeric LILRB2 receptor reporter cells were treated with indicated soluble or coated full-length, CC domain, or FBN domain of Angptl2 for 48 hrs. PBS was used as control. *, $p<0.05$; n.s., not significant.

To identify the sites in Angptls that bind to LILRB2, the binding of full-length with CC and FBN domains of Angptl2 to LILRB2 was compared. The full-length protein, but not the CC or the FBN domain of Angptl2, bound to 293T cells that expressed LILRB2 21. The full-length protein and the CC domain (but not FBN domain) of Angptl2 bound to LILRB2+ human CB mononuclear cells (FIG. 9). The full-length Angptl2, the FBN domain, and a high concentration of soluble CC domain were able to activate LILRB2 reporter cells (FIG. 10). It is speculated that the actual concentration of the CC domain coated on the plastic dish might be lower than that of the soluble CC domain, and therefore this immobilized CC domain was not sufficiently high to activate the LILRB2 chimeric reporter. These results suggest that both CC and FBN of Angptl2 are needed for optimal binding and activation of LILRB2.

Anti-LILRB2 antibodies support ex vivo expansion of human CB HSCs. Although numerous conditions have been used for expansion of HSCs in culture, the optimal mixture of growth factors and cytokines to allow expansion sufficient for clinically applicability has not yet been determined. See, for example, Chou et al., Cell Stem Cell. 2010; 7:427-428; Delaney et al., Nat Med. 2010; 16:232-236; Himburg et al., Nat Med. 2010; 16:475-482; Zheng et al., Cell Stem Cell. 2011; 9:119-130; Boitano et al., Science. 2010; 329:1345-1348; Butler et al., Cell Stem Cell. 2010; 6:251-264; North et al., Nature. 2007; 447:1007-1011; Antonchuk et al., Cell. 2002; 109:39-45; Dahlberg et al., 2011; 117:6083-6090; Kirouac et al., Curr Opin Biotechnol. 2006; 17:538-547; and Robinson et al., Cytotherapy. 2005; 7:243-250.

Previously Angptls were identified as growth factors for HSC expansion. Zheng et al., Blood. 2011; 117:470-479; Zhang et al., Blood. 2008; 111:3415-3423 and Zhang et al., Nat Med. 2006; 12:240-245. However, because Angptls are large glycosylated proteins that are readily degraded and form aggregates, they are difficult to express and purify and thus are not ideal components for use in culture. Molecules with enhanced stability and higher activities that mimic the effects of the Angptls would lead to the development of a more efficient HSC expansion system. Based on the finding that immobilized antibody to LILRB2 mimicked Angptl2-stimulated receptor signaling (FIGS. 5A-5D), whether immobilized anti-LILRB2 antibody would support ex vivo expansion of human CB HSCs was tested.

Figure 11A:
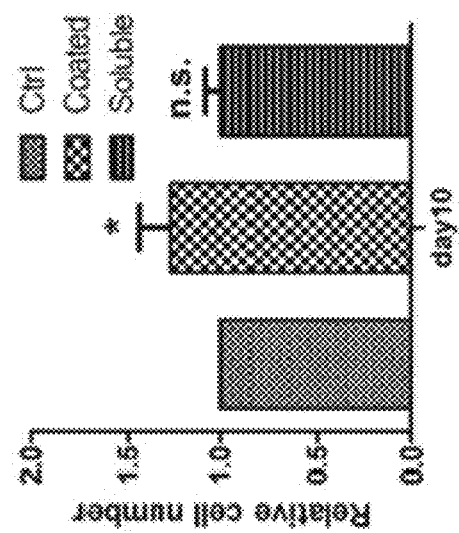
FIGS. 11A-11E. Immobilized anti-LILRB2 antibodies promote the proliferation of human CB cells in vitro.
Figure 11B:
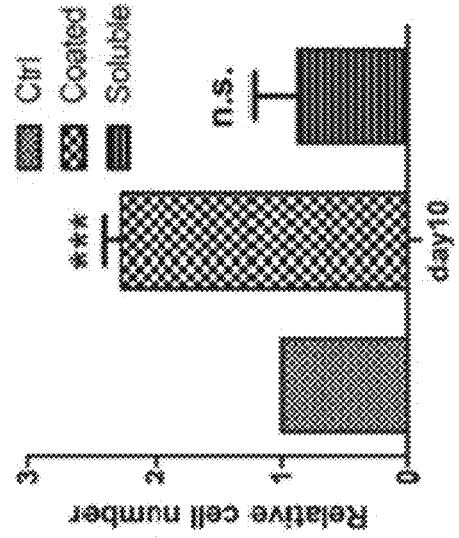
Figure 11C:
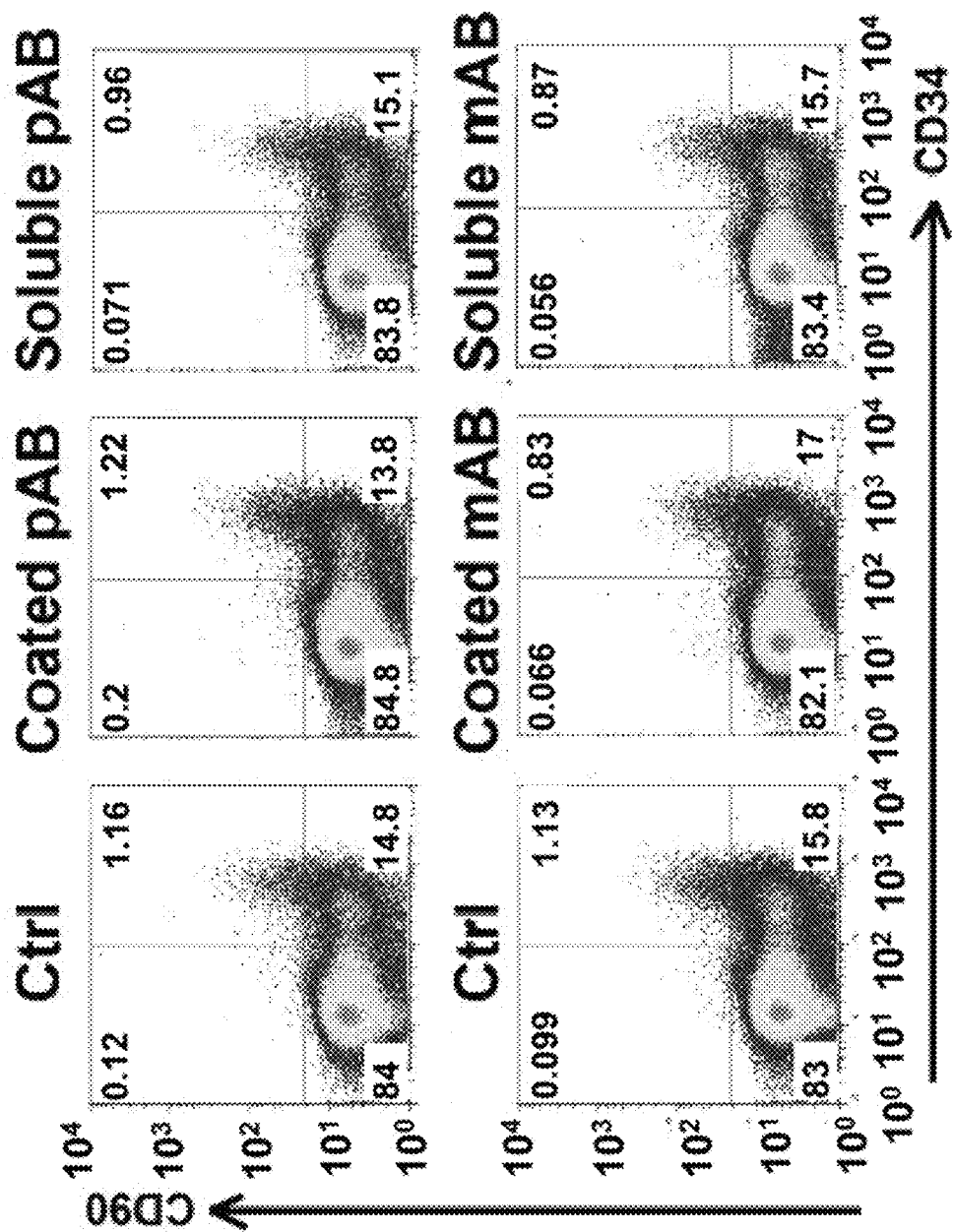

Culture of human CB CD133+ cells in STF medium, medium with soluble anti-LILRB2, and medium with immobilized either polyclonal (pAb) or monoclonal (mAb) anti-LILRB2 antibody was first compared. $1\times10^4$ cryopreserved human CB CD133+ cells were plated in indicated medium; after 10 days of culture the total numbers of cells were determined. More expansion resulted from culture with immobilized pAb or mAb than either in STF medium or STF medium containing soluble antibodies (230% and 125% of the STF sample value, respectively; FIGS. 11A-11B). It is of note that the levels of CD34+CD90+ cells that may be enriched in cultured HSCs were similar in these conditions (FIG. 11C).

Figure 11D:
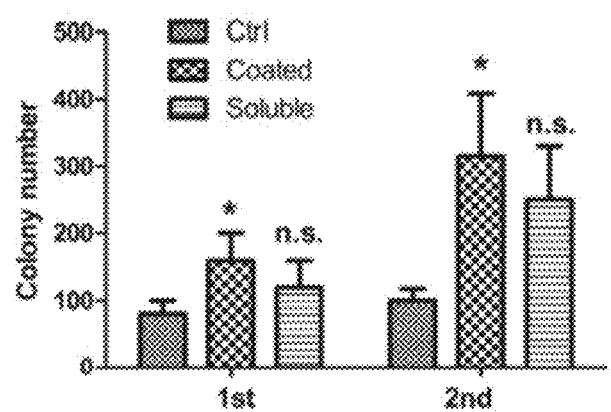
Figure 11E:
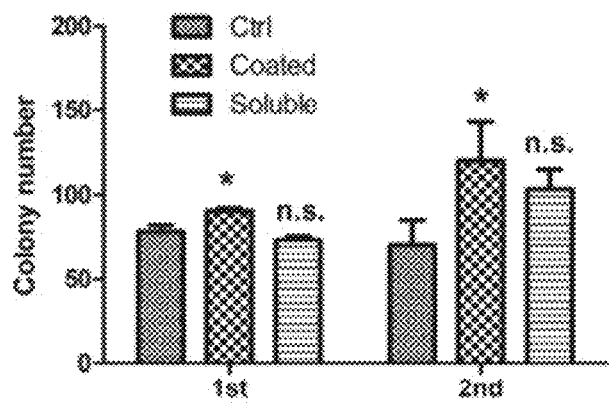

Colony-forming assays were next performed. Concordant with the cell growth results, samples of cells treated with the immobilized antibodies had significantly increased colony forming units (CFUs) in both primary and secondary colony forming assays than the STF sample or the soluble antibody sample (FIGS. 11D-11E). In particular, the immobilized polyclonal and monoclonal antibody treated samples had more than 3-fold and 1.6-fold of CFUs, respectively, than the STF samples in the secondary replating.

Figure 12A:
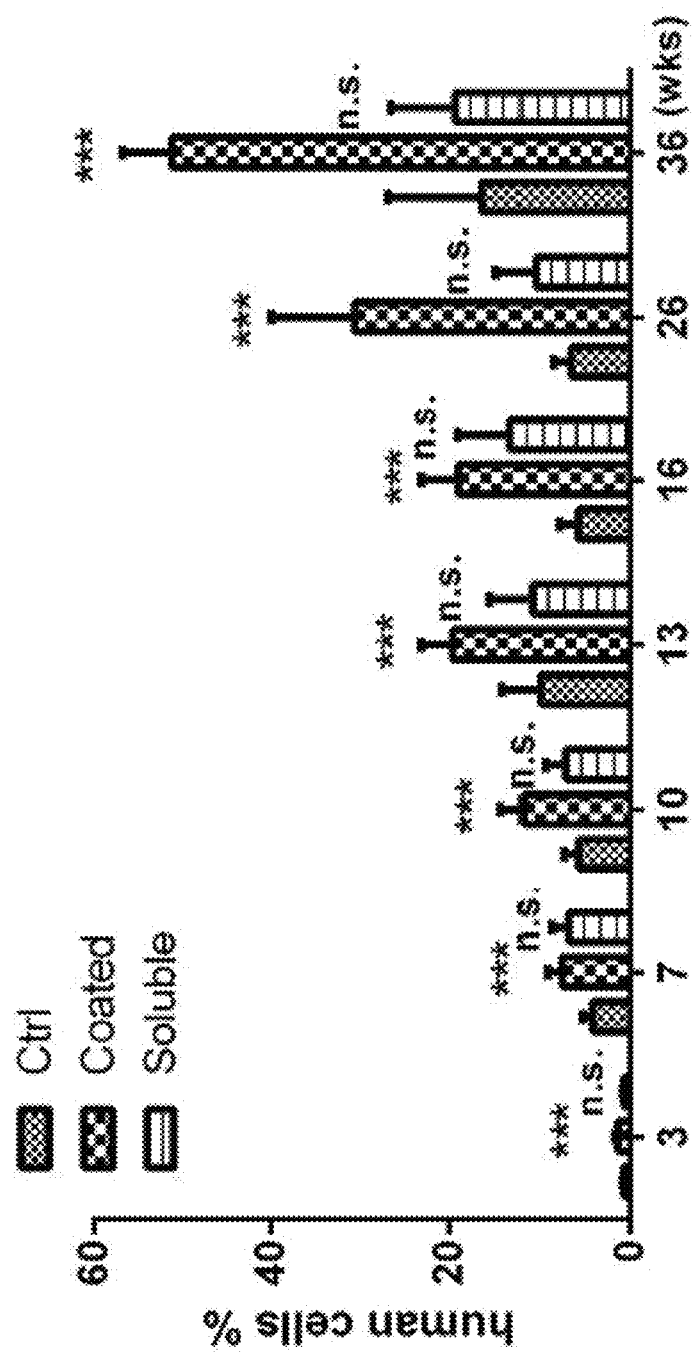
FIGS. 12A-12L. Ex vivo expansion of human CB CD133+ cells by anti-LILRB2 polyclonal antibody as determined by NSG transplantation.
Figure 12B:
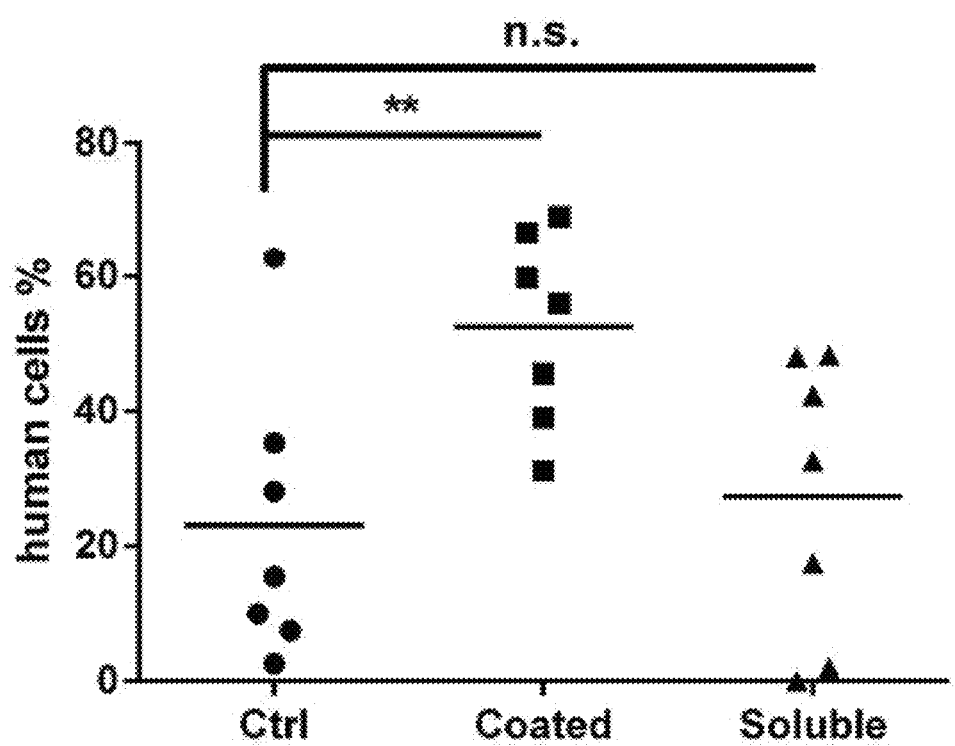
Figure 12C:
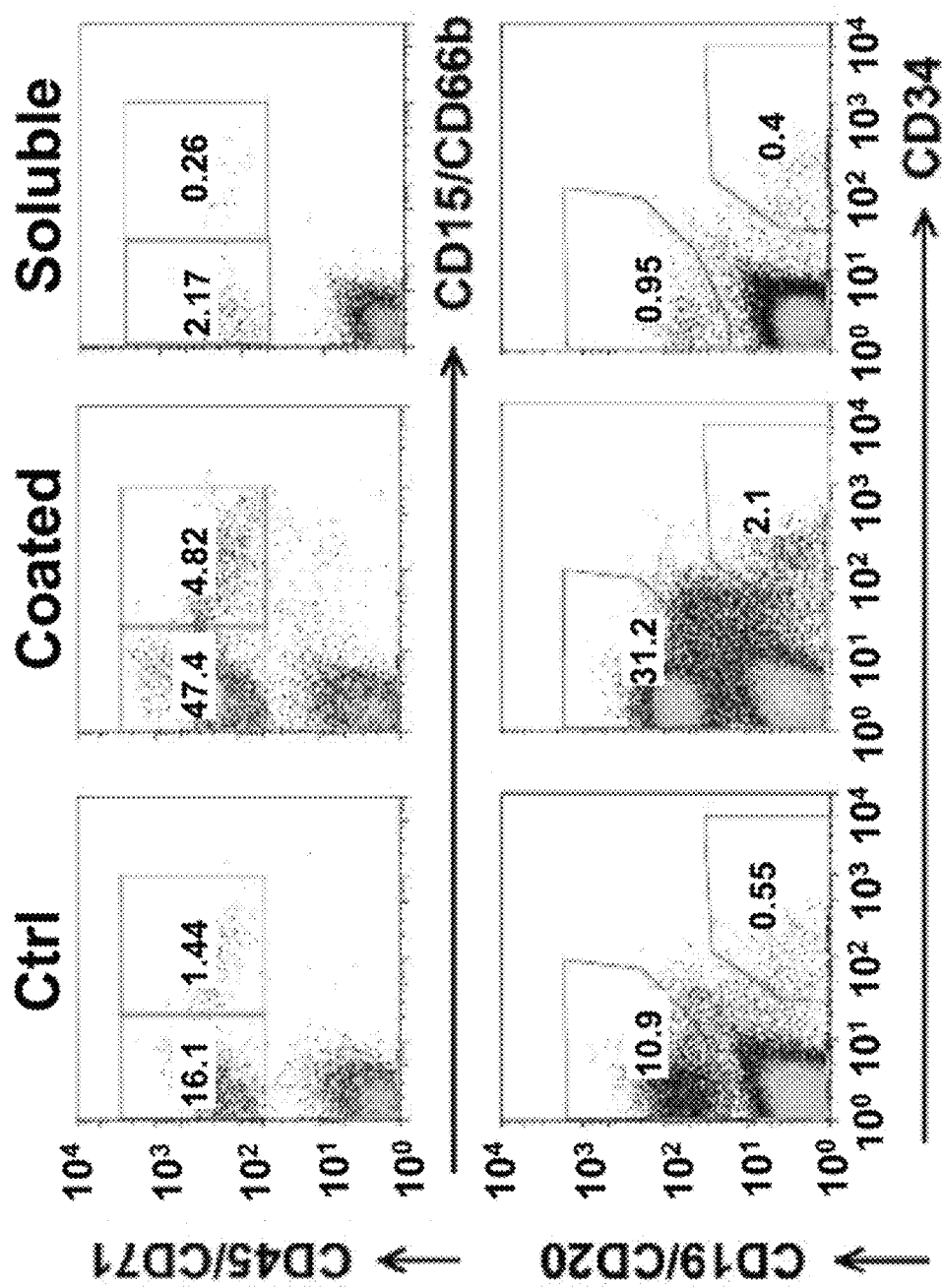
Figure 12D:
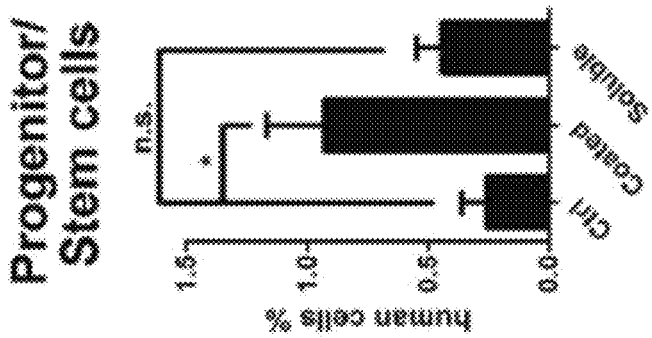
Figure 12E:
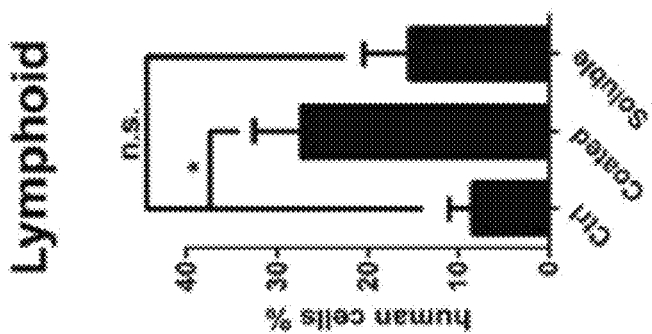
Figure 12F:
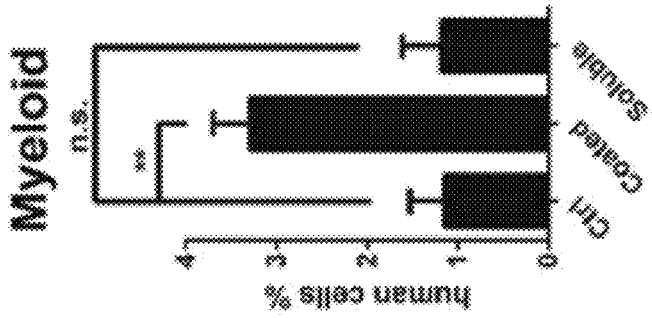
Figure 12G:
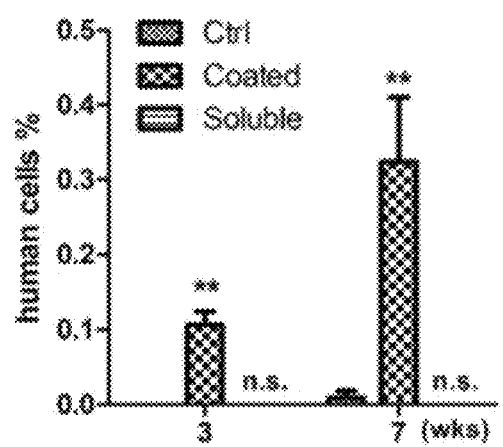
Figure 12H:
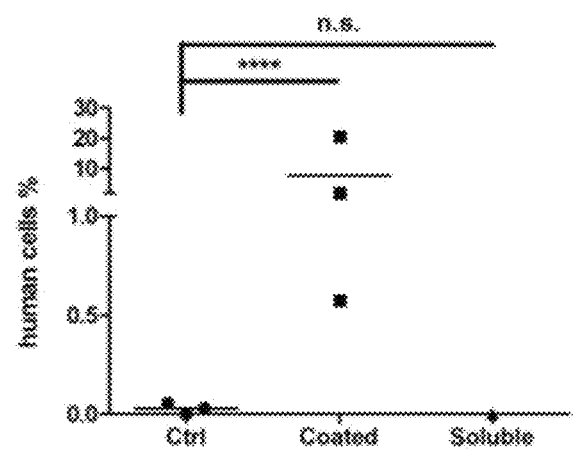
Figure 12I:
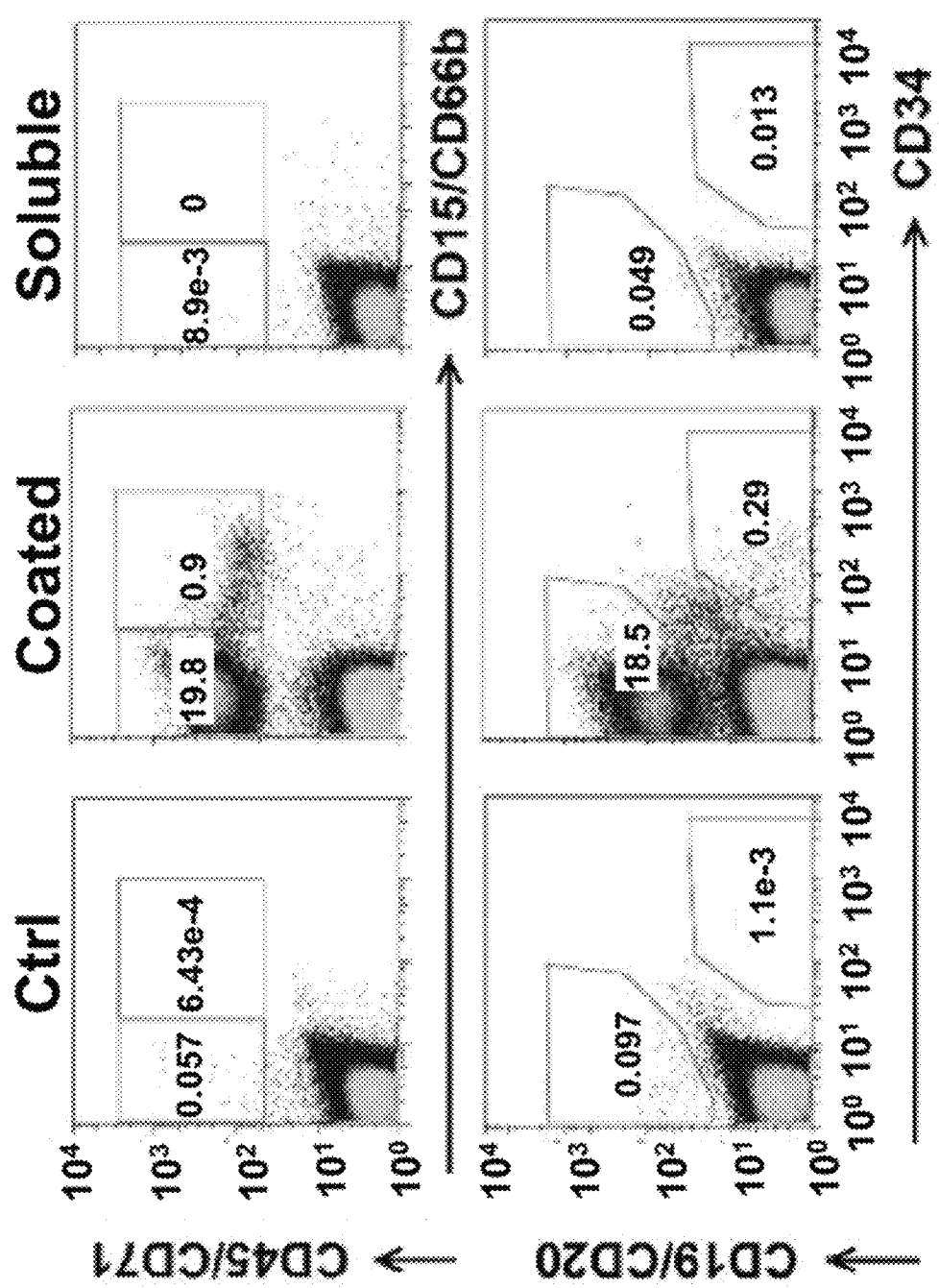
Figure 12L:
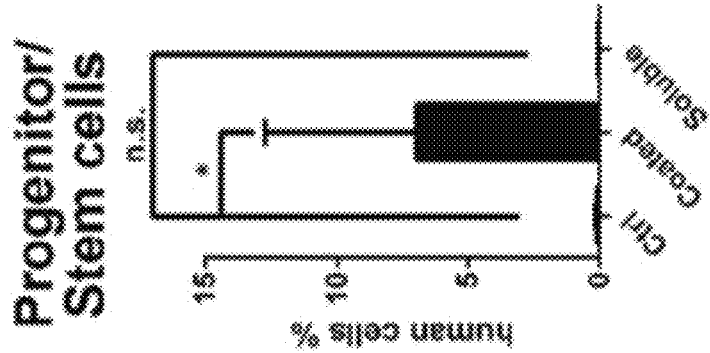
Figure 12K:
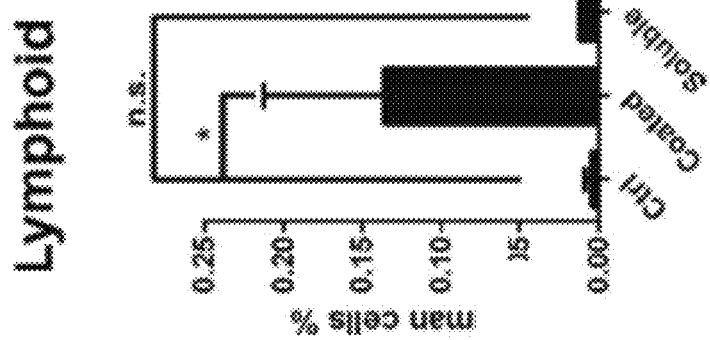
Figure 12J:
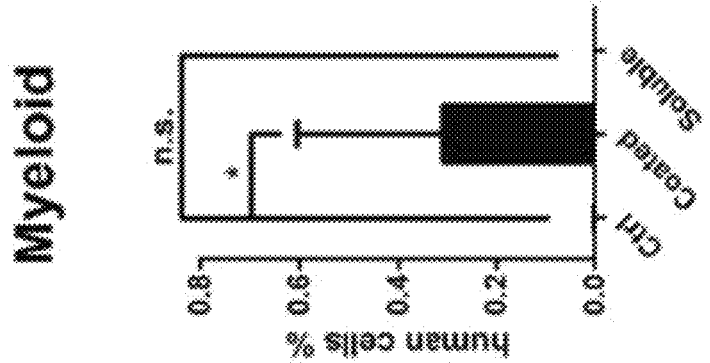
Figure 13A:
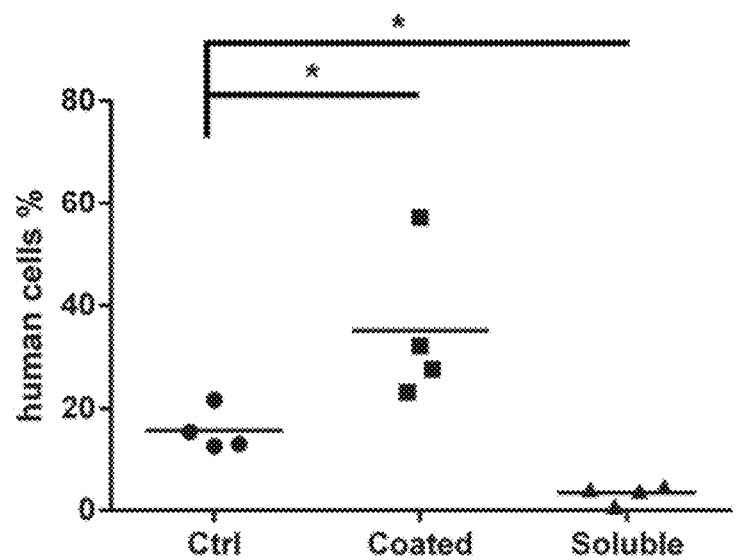
FIGS. 13A-13D. Ex vivo expansion of human CB CD34+ cells by anti-LILRB2 polyclonal antibody as determined by NSG transplantation.
Figure 13B:
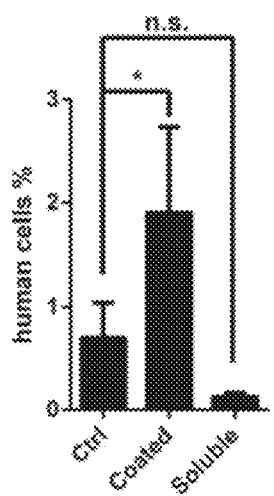
Figure 13C:
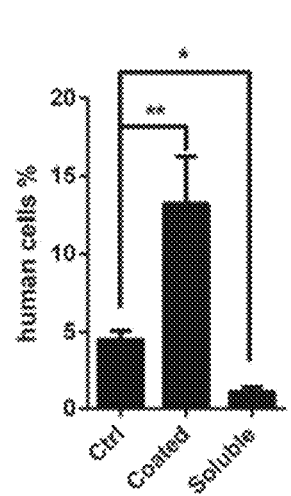
Figure 13D:
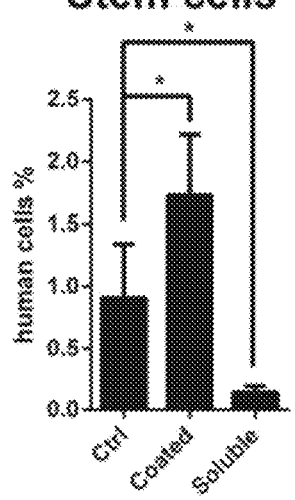
Figure 14A:
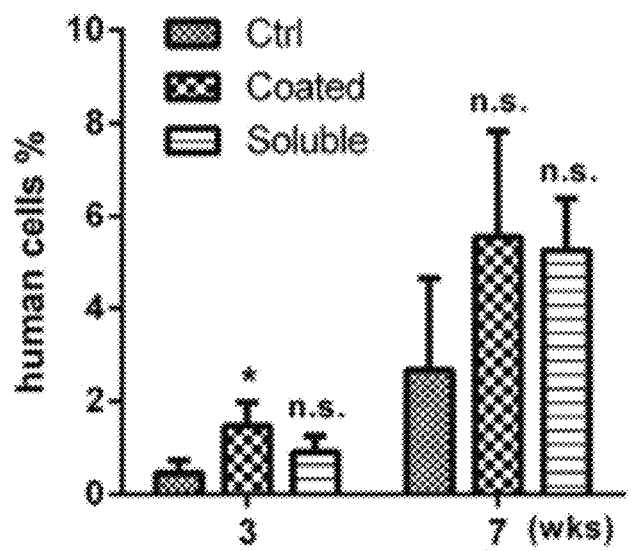
FIGS. 14A-14L. Ex vivo expansion of human CB CD133+ cells by anti-LILRB2 monoclonal antibody in NSG mice as determined by NSG transplantation.
Figure 14B:
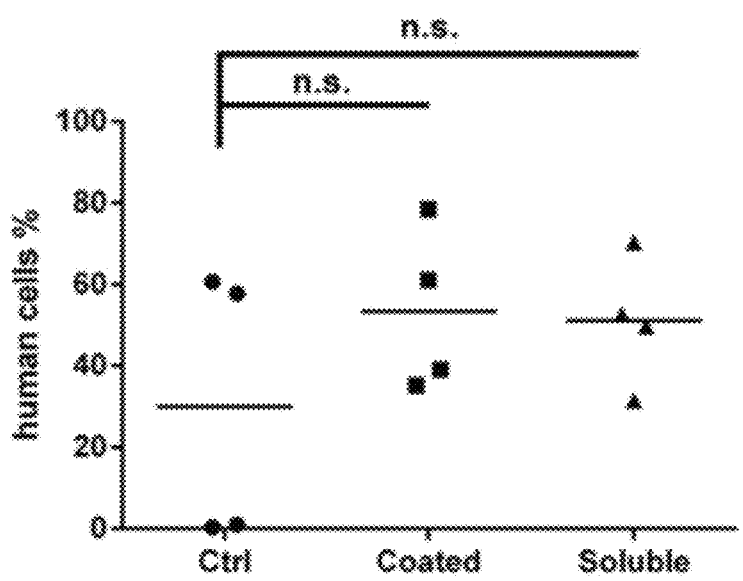
Figure 14C:
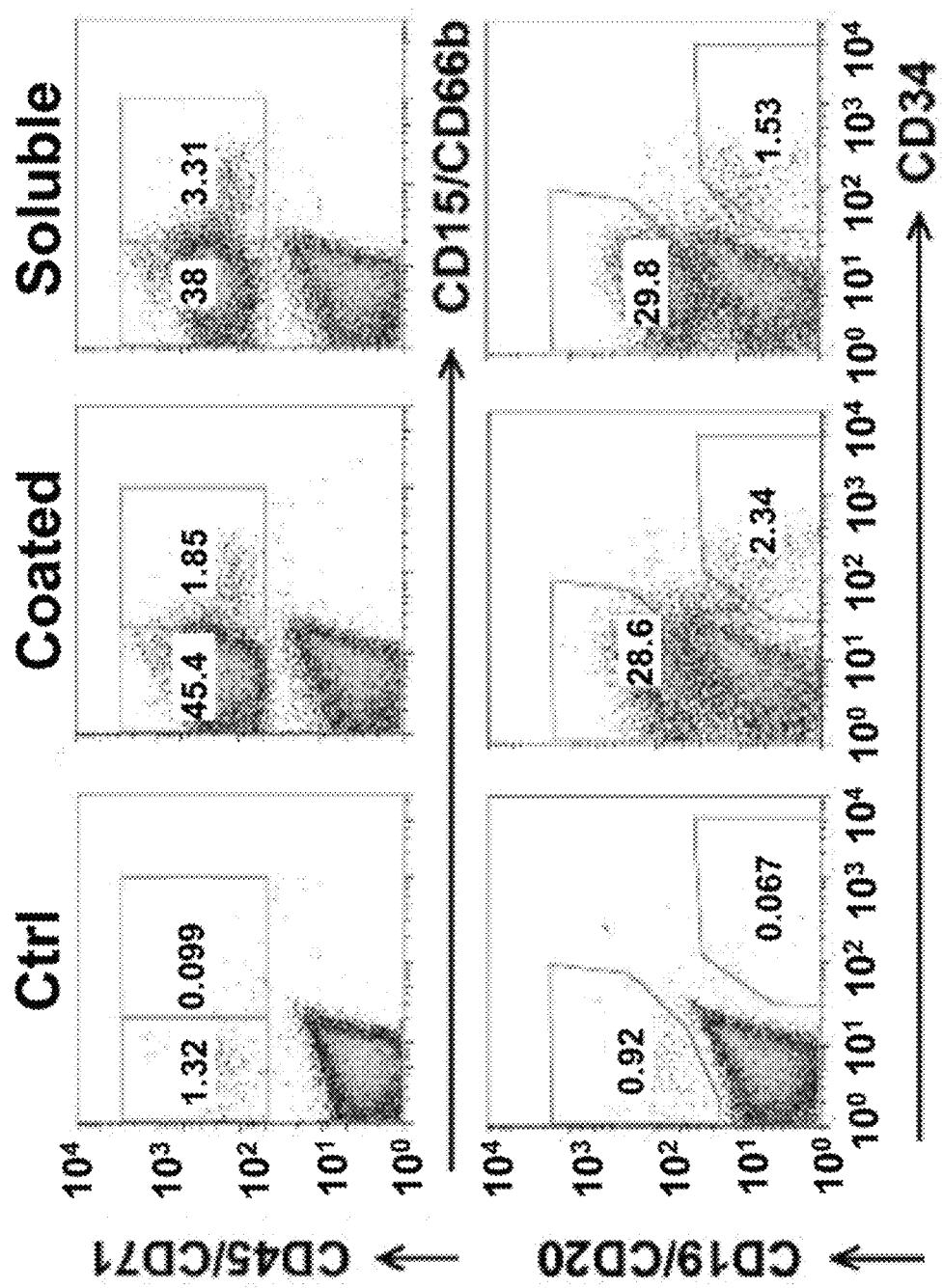
Figure 14D:
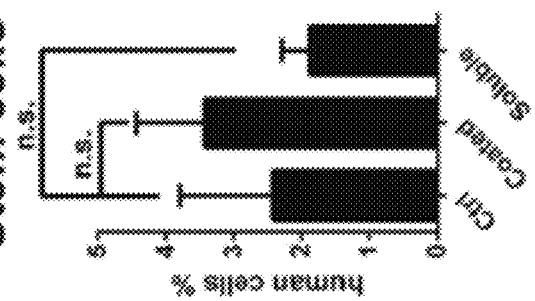
Figure 14E:
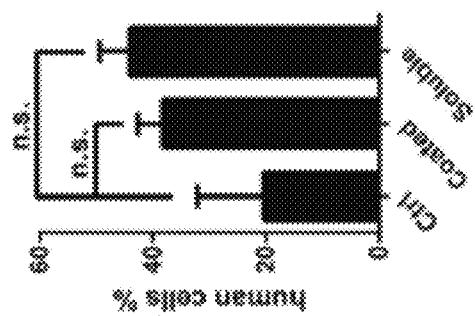
Figure 14F:
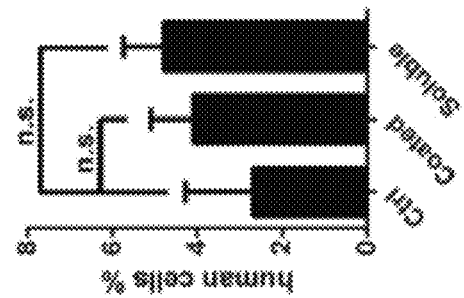
Figure 14G:
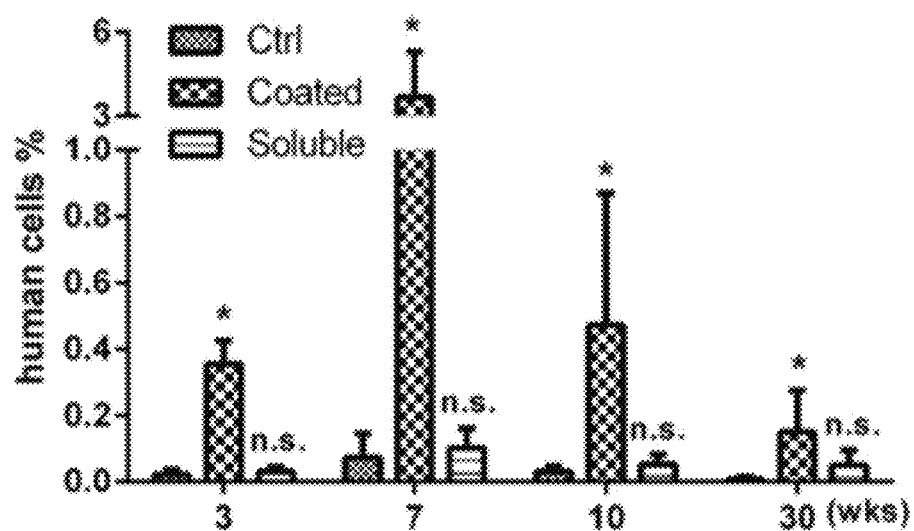
Figure 14H:
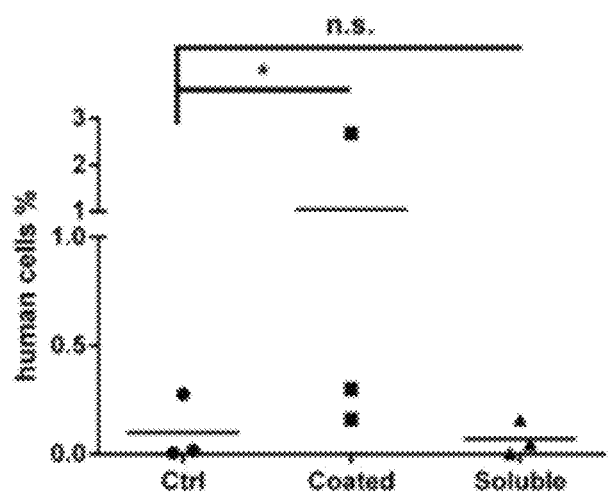
Figure 14I:
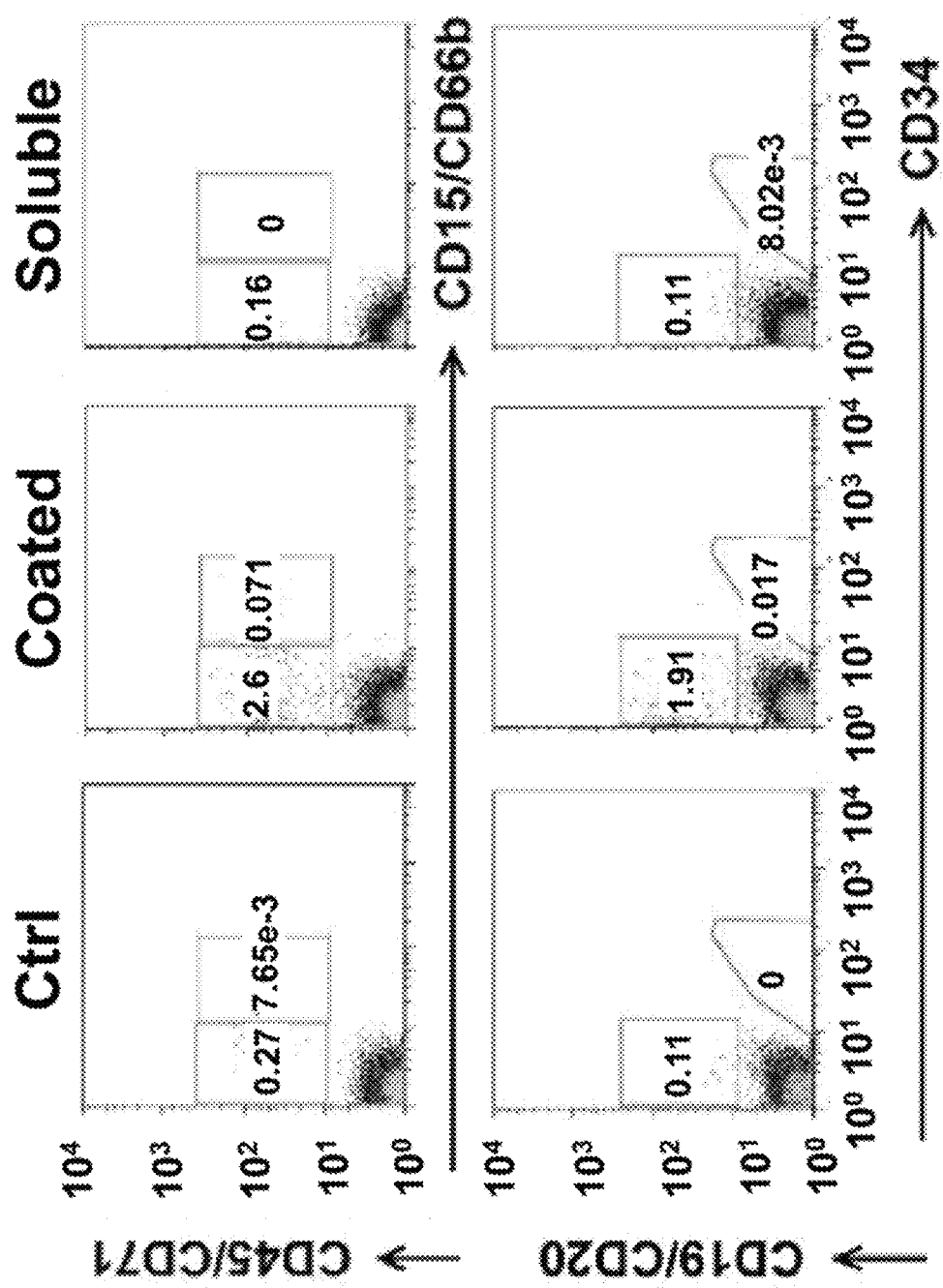
Figure 14J:
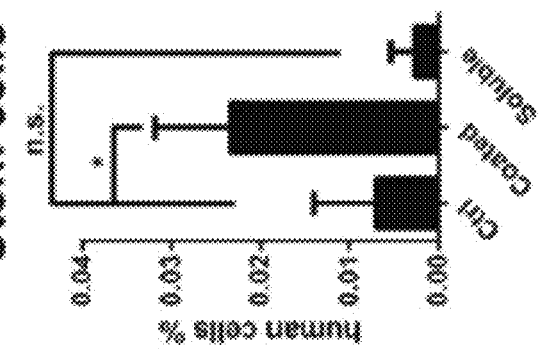
Figure 14K:
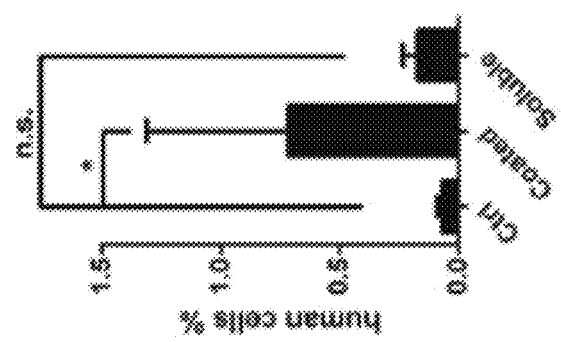
Figure 14L:
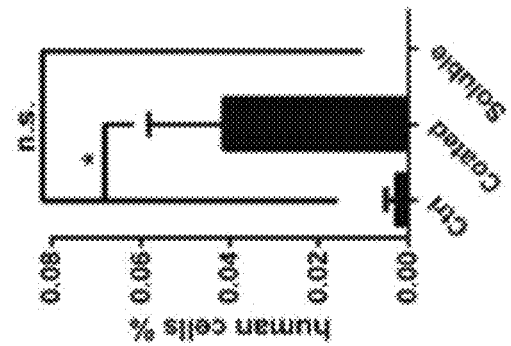

Finally, cells cultured in these same conditions were transplanted into sublethally irradiated NSG mice ($1\times10^4$ input equivalent cells per mouse). CD133+ cells cultured with immobilized anti-LILRB2 pAb had a significantly greater average chimerism in peripheral blood and bone marrow than the counterparts without antibody treatment or than cells treated with soluble antibody at the analyzed post-transplant time points (3-36 weeks, FIGS. 12A-12B). FIG. 12C shows human hematopoietic engraftment at 36 weeks in representative mice that were transplanted with differently cultured human CB CD133+ cells. Mice that were transplanted with cells cultured in immobilized antibody displayed a much higher engraftment of total hematopoietic (CD45/71+) (52.48±5.41% versus 23.13±7.93%; FIG. 12B), myeloid (CD15/66b+) (3.29±0.41% versus 1.16±0.38%; FIG. 12D), B-lymphoid (CD34-CD19/20+) (27.43±5.15% versus 8.52±2.58%; FIG. 12E), and primitive (CD34+) (0.93±0.24% versus 0.26±0.10%; FIG. 12F) human cells than mice transplanted with STF cultured cells or cells cultured with soluble antibody (FIGS. 12B, 12D-12F).

To measure the self-renewal potential of SCID-repopulating cells (SRCs) after culture, bone marrow was collected from the primary mice and transplanted into sublethally irradiated secondary recipients. Engraftment of secondary recipients with cells cultured in STF medium or in soluble antibody was barely detectable. In contrast, the cells cultured with immobilized antibody showed positive engraftment of myeloid, B-lymphoid, and primitive cells after the secondary transplantation (FIGS. 12G-12L). Similar results were obtained from another independent experiment using human CB CD34+ cells for culture (FIGS. 13A-13D).

CD133+ cells cultured with soluble or immobilized anti-LILRB2 mAb were also transplanted into sublethally irradiated NSG mice ($1\times10^4$ input equivalent cells per mouse). In the primary transplantation, engraftment with immobilized monoclonal anti-LILRB2 treated cells was detectable but not significantly different from cells cultured without antibody treatment or with soluble anti-LILRB2 (FIGS. 14A-14F). In the secondary transplantation, however, only cells treated with immobilized anti-LILRB2 showed positive engraftment (FIGS. 14G-14L). Together, the data indicate a net expansion of HSCs during the initial culture period, and it is thus concluded that immobilized anti-LILRB2 antibodies support extensive ex vivo expansion of human SRCs.

Figure 15C:
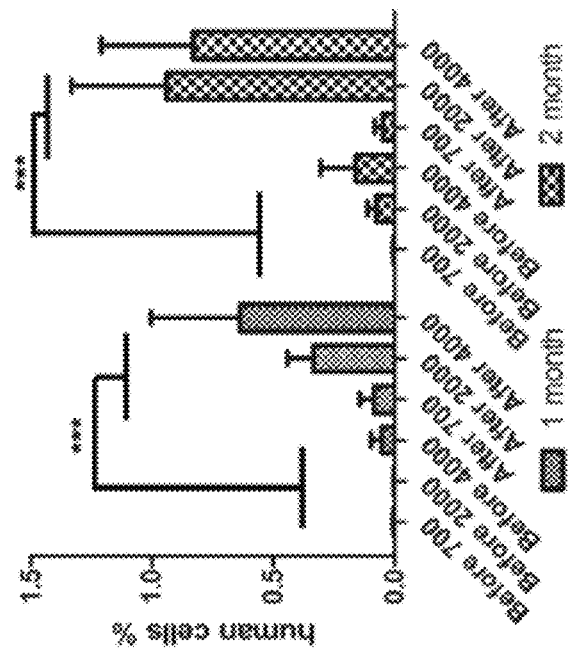
Figure 15B:
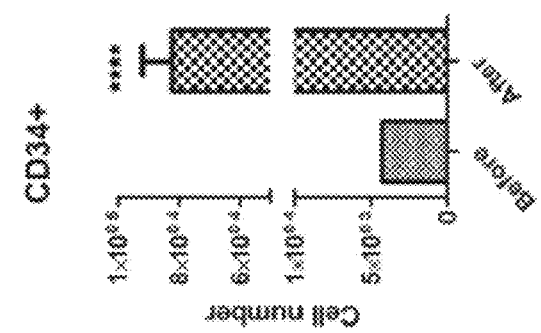
Figure 15A:
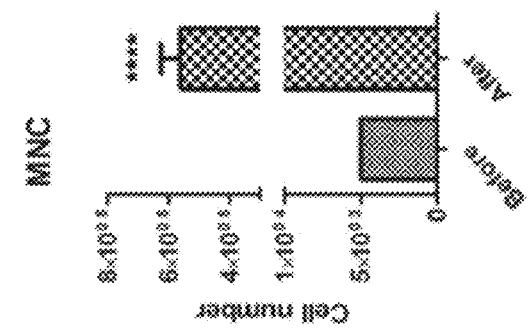
Figure 15D:
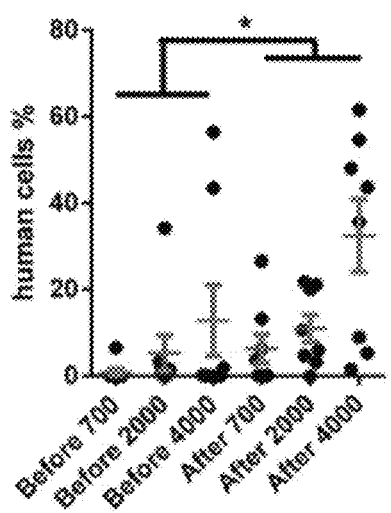
Figure 15E:
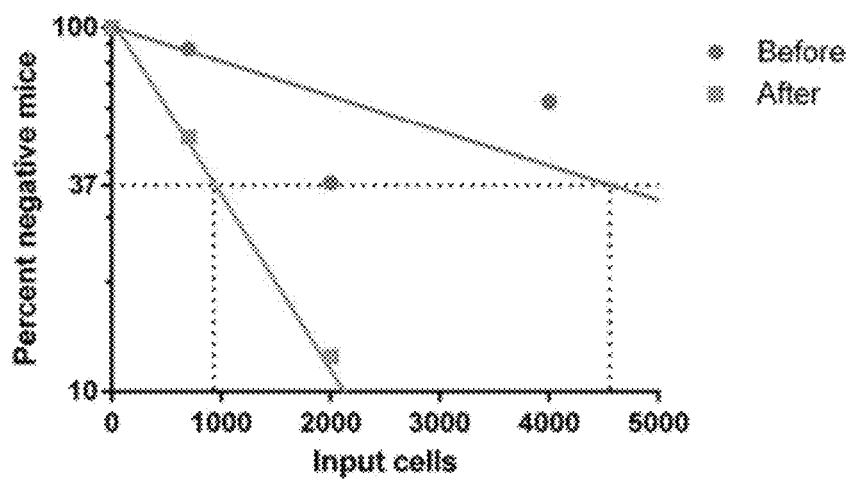

A limiting dilution assay was performed to quantitate the SRC frequencies before and after culture. Human CB CD133+ cells cultured with immobilized anti-LILRB2 antibody-cultured for 10 days had a 112-fold increase in total nucleated cells (TNCs) and a 19-fold increase in CD34+ cells relative to input cells (FIGS. 15A-15B). Cultured cells had greater average chimerism than in peripheral blood (FIG. 15C) and bone marrow (FIG. 15D). As part of the limiting dilution assay, the engraftment by 700-4,000 uncultured CD133+ cells, and the progenies of these cells after culture was measured. All mice transplanted with the cultured progenies of 4,000 CD133+ cells engrafted at a level greater than 1%. FIG. 15E shows that the frequency of repopulating cells (CRU) from uncultured CD133+ cells is 1 per 4557 cells (95% confidence interval for mean: 3222 to 6445, n=24). That is, as calculated from Poisson statistics, injection of an average of 4,557 cells from this lot of uncultured human CD133+ cells would be sufficient to repopulate 63% (=1-1/e) of transplanted mice. In contrast, the CRU after culture was 1 per 932 input equivalent cells (95% confidence interval for mean: 689 to 1261, n=24). There was a 4.9-fold increase in the number of SRCs after cultured in STF medium with immobilized anti-LILRB2 polyclonal antibody. These cultured cells had much greater levels of multi-lineage engraftment than uncultured cells (FIGS. 15F-15I).

It has previously been shown that several Angptls support ex vivo expansion of HSCs (Zhang et al., Blood. 2008; 111:3415-3423; Zhang et al., Nat Med. 2006; 12:240-245; and Huynh et al., Stem Cells. 2008; 26:1628-1635) but the mechanism responsible for this activity was unknown. Here it has been demonstrated that mammalian-expressed Angptl2 exists as HMW species, and ligand multimerization is required for activation of LILRB2 for downstream signaling. Motifs in the Ig domains of LILRB2 that are critical for the Angptl2 binding and signaling activation were also identified. It was shown that the binding of Angptl2 to LILRB2 is greater than and not completely overlapped with the binding of another ligand HLA-G. In an attempt to identify agonists of LILRB2 that are more potent and stable than Angptl to support ex vivo expansion of human HSCs, it was found that immobilized polyclonal anti-LILRB2 supports consistent ex vivo expansion of human CB HSCs. This study thus started to uncover the molecular basis for Angptl/LILRB2 interaction. It also provides functional evidence that manipulation the binding between the ligands and LILRB2 on HSCs supports the repopulating activity of HSCs, and demonstrated a novel approach for efficient expansion of HSCs that may find utility in HSC-based cell therapies.

While the bona fide signaling reporter of LILRB2 is not available, a chimeric receptor surrogate reporter system was developed that can evaluate the ability of a ligand to bind and activate LILRB2. As shown in the described studies, this reporter cell line can serve as a sensitive system to enable comparison of the signaling-induction abilities of different forms of ligands. This chimeric receptor reporter system will also be useful to screen additional agonists and antagonists of ITIM-containing receptors. It is envisioned that the agonists of ITIM-containing receptors may facilitate stem cell-based regenerative medicine, and the antagonists may serve as inhibitors of cancer development.

The critical factors that contribute to LILRB2 activation by Angptl2 were identified. First, it was determined that mammalian-expressed Angptl2 forms BMW species that appear to be important for its binding to the receptor. Angptl2 contains both CC and FBN domains. Based on several pieces of evidence, neither the CC domain nor the FBN domain of Angptl2 alone bind to LILRB2 as potently as the full-length Angptl2. Both the CC domain and full-length LILRB2 exist as HMW species, whereas the FBN domain does not. Concordantly, a previous study showed that the CC domain of Angptl4 mediates multimerization. Ge et al., J. Biol Chem. 2004; 279:2038-2045. These data suggest that both CC and FBN domains contribute to the receptor binding and that the CC domain-mediated multimerization significantly enhances the binding of the full-length Angptl2 to LILRB2. Although Angptls are observed as soluble hormones in serum, they can also be enriched on the plasma membrane in vitro (data not shown). In addition to the soluble multimerized form, it is speculated that clustered, cell surface-bound Angptls exist in vivo and activate LILRB2.

The features of LILRB2 important for Angptl2 binding were further identified. Novel H*G*Y*C motifs in the first and fourth Ig domains of LILRB2 are essential to Angptl2 binding. The critical necessity of this motif in Angptl2/LILRB2 binding is supported by the effects of the site-specific mutations at G94, R95, and Y96 in Ig1 that reduced Angptl2 binding by 50%. Similarly, a single mutation in Y394 in Ig4 decreased Angptl2 binding of full-length LILRB2 by 40%. In addition to Angptls, LILRB2 is known to have other ligands including various MHC class I molecules. Shiroishi et al., Proc Natl Acad Sci USA. 2003; 100:8856-8861. An important question is whether Angptl and MHC class I molecules bind to LILRB2 in a similar or different manner. As the flow cytometry-based ligand binding assay showed, Angptl2 has a greater binding than HLA-G to LILRB2. This result is supported by the described reporter cell assay. In contrast to Angptl2, a much greater dose of the immobilized HLA-G cannot induce GFP expression of the LILRB2 reporter cells. Therefore, the Angptl2 activation of the LILRB2 chimeric receptor reporter cells is much more potent than HLA-G; however, Angptl2 is not efficiently to compete the HLA-G binding to LILRB2 (data not shown). Whereas HLA-G binds to the first two Ig domains of LILRB2 28, Angptl2 binds to both Ig1 and Ig4 of LILRB2. Interestingly, the H*G*Y*C motif that is critical for Angptl2 binding to LILRB2 is not within either of the two MHC binding sites or at the typical interfacial loop region, but within the beta-sheet structure, as revealed by a crystallographic study. Shiroishi et al., Proc Natl Acad Sci USA. 2006; 103:16412-16417. Based on the described binding and activation results, this motif should be required for the conformational stability of the Ig domains of LILRB2 that is needed for binding and activation by Angptl2. Together, these results suggest that, 1) Angptl2 binds and activates LILRB2 with a greater ability than MHC class I, and 2) Angptl2 and MHC class I molecules may not directly compete for binding to the same sites, and these two types of molecules may be able to act individually or even cooperatively so that the signaling of LILRB2 may be co-regulated. Nevertheless, the binding of each of the two ligands may somewhat require common conformational alterations. For example, while the mutations of most of the MHC-I binding sites of LILRB2 did not affect Angptl2 binding, it was observed that the mutation G94D, R95E, or Y394A in LILRB2 that is within the H*G*Y*C motif and decreases Angptl2 binding also showed lower HLA-G binding.

Interestingly, while all LILRBs contain a G*Y*C motif, Angptl2 only binds LILRB2. This suggests that the H*G*Y*C motif is necessary but not sufficient for maintaining the LILRB2 conformation for Angptl2 binding and activation.

Based on the described identification of the binding sites of Angptl2 to LILRB2, an improved strategy to use immobilized anti-LILRB2 for ex vivo expansion of human HSCs was developed. Immobilized antibodies bind to the same region of LILRB2 as Angptl2. The serum-free culture system containing defined cytokines and immobilized anti-LILRB2 supports a net expansion of repopulating human CB HSCs, as determined by the serial NSG transplantation and limiting dilution analysis. The polyclonal anti-LILRB2 antibody demonstrated a greater ability to support ex vivo expansion of HSCs than monoclonal anti-LILRB2, suggesting the possibility of multiple ligand binding sites in LILRB2 activation. In addition, the internalization signal YXXphi of LILRB2 (Kozik et al., Traffic. 2010; 11:843-855) suggests that LILRB2 can undergo endocytosis, possibly after ligand binding. Because the immobilized antibodies may prevent this event and thus prolong the receptor activation, the ex vivo expansion of HSCs may also be enhanced by the immobilized antibodies. Together, because the anti-LILRB2 polyclonal antibodies are easier to be expressed and purified and more stable than Angptls, and importantly, bind and activate LILRB2 with a greater ability than Angptl2, this system may have greater advantages to use in ex vivo expansion of HSCs.

3.2 Example 2

Figure 16:
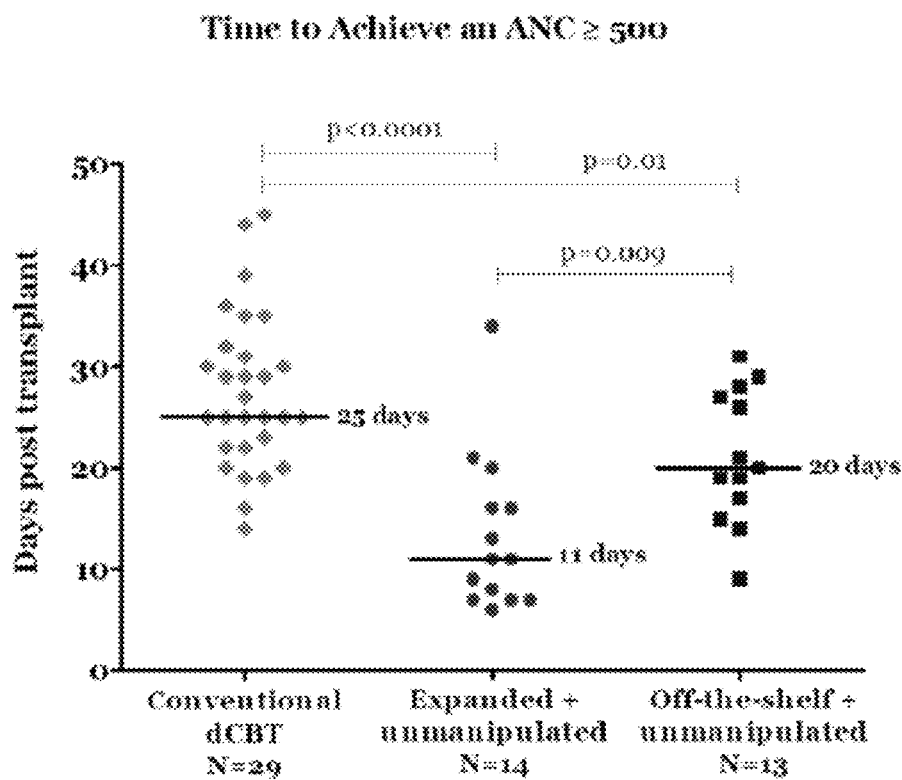
FIG. 16. Clinical grade culture of CB progenitors with Delta1 results in more rapid neutrophil recovery in a myeloablative double CB transplant (CBT) setting. Individual and median times (solid line) to absolute neutrophil counts (ANC) of ≥500/µl for patients receiving double unit CB transplants with two non-manipulated units ("conventional"), one ex vivo expanded unit and one non-manipulated unit, or the "off-the-shelf" expanded product and a non-manipulated unit. Comparisons made using two-tailed t-test.
Figure 17:
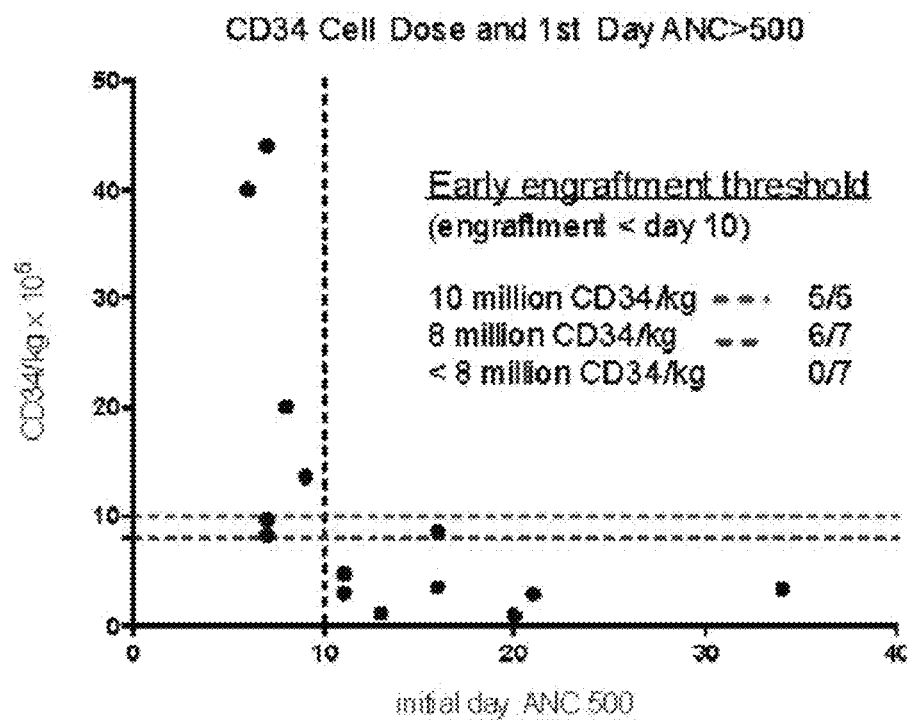
FIG. 17. Defining a CD34 Cell Dose for Early Myeloid Engraftment. CD34 cell dose versus time to neutrophil engraftment (ANC>500) demonstrating cell doses above which more rapid early myeloid engraftment (before day 10) occurs. 6/7 patients with greater than 8 million CD34/kg (blue line) and 5/5 patients with greater than 10 million CD34/kg (red line) demonstrated early engraftment.

Previous studies have led to Notch-induced ex vivo expansion of hematopoietic stem cells (HSC) and their successful use for reducing the prolonged post-transplant neutropenia encountered in patients undergoing CB stem cell transplantation (see FIGS. 16 and 17). More recently a relationship between the number of expanded, partially HLA-matched CD34+ cells infused and time to neutrophil recovery has been observed, suggesting a critical need for greater expansion of CB HSPC to reliably enhance early neutrophil recovery.

To alleviate the risks associated with delayed myeloid recovery, methods for ex vivo expansion of CB HSPC that are infused along with one or two non-manipulated CB units in the setting of myeloablative hematopoietic stem cell transplantation (HSCT) have been developed. These methods are based on previously described studies of the role for the Notch receptor family in regulation of hematopoiesis and on pre-clinical development of a Notch-mediated expansion system for hematopoietic progenitors using the Notch ligand Delta1. Milner et al., Blood. 1994; 83(8): 2057-2062; Varnum-Finney et al., Nat Med. 2000; 6(11): 1278-1281; Varnum-Finney et al., Blood. 2003; 101(5): 1784-1789; Delaney et al., Blood. 2005; 106(9): 2693-2699. Clinical translation of this work resulted in a Phase I CBT trial using ex vivo expanded CB progenitor cells following myeloablative conditioning. Results of this trial showed both safety of this approach as well as significant decrease in time to neutrophil engraftment. An update of these studies since the initial publication (Delaney et al. Nat Med. 2010; 16(20): 232-237) shows reduction in median time to initial ANC≥500/µl of 11 days compared with a concurrent cohort of patients (N=29) with the same treatment regimen (p<0.0001, FIG. 16). Significantly, achievement of ANC>100/µl, an indicator of risk of day +100 mortality (Dahlberg et al. Blood. 2011; 118(21): 3033) occurred at 7 days as compared to 19 days in the conventional double CBT group (p=0.0002). Moreover a relationship between number of HSPC infused and time to engraftment, with 6 out of 7 patients who received greater than 8×10$^6$ CD34+ cells/kg achieving an ANC≥500/µl within 10 days (FIG. 17) was observed, findings unique with respect to cell-therapy based reduction of neutropenia. This observed dose-relationship is reflective of studies in non-manipulated CBT indicating that higher cell doses of CD34+ cells/kg are required to overcome increased HLA disparity and allow engraftment in partially-HLA matched CBT recipients. Laughlin et al. N Engl J Med. 2001; 344(24): 1815-1822; Wagner et al. Blood. 2002; 100(5): 1611-1618.

Aspects of the current disclosure are based on the hypothesis that inhibition of differentiation by induction of endogenous Notch signaling in combination with factor(s) able to enhance stem self-renewal and/or survival will lead to generation of greater numbers of rapidly repopulating CD34+ HSPC. One such factor is angiopoietin agonists including, for example, Angptl5. Angptl5 a member of the Angiopoietin-like family of proteins previously shown to enhance the generation of hematopoietic repopulating cells in preclinical studies.

Figure 18:
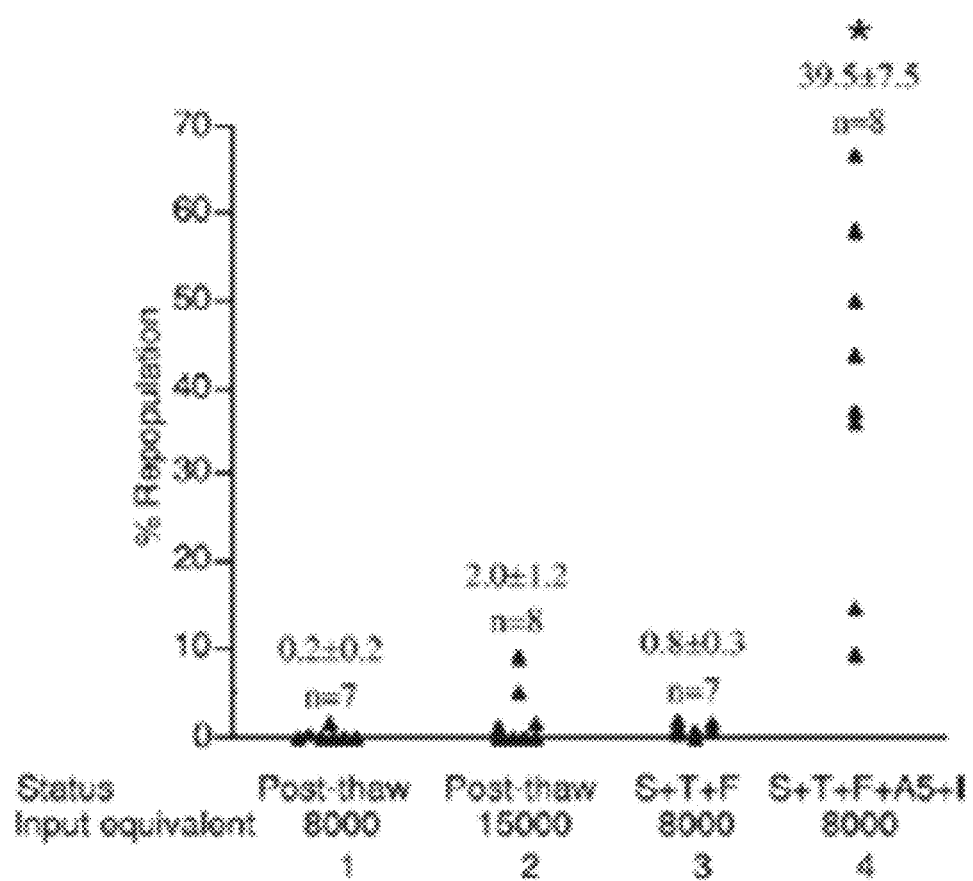
FIG. 18. Culture of human CB hematopoietic stem/progenitor cells (HSPC) in the presence of Angptl5 stimulates expansion of in vivo repopulating cells. Human repopulation in bone marrow of uncultured cells, cultured cells in the absence of Angptl5 (S+T+F) or cells cultured with Angptl5 (S+T+F+A5+I). Cell numbers transplanted are represented below conditions (for cultured cells number is progeny of cells generated in culture).

For example, in vitro culture with Angptls 2, 3, 5, and 7 and cytokines significantly increases repopulating activities of murine long-term HSC. Zhang et al., Nat Med. 2006; 12(2): 240-245. Culture of CB HSPC with ANGPTL5 and growth factors (SCF, TPO, FGF-1, heparin, and IGFBP2) led to significantly improved in vivo reconstitution in NOD/SCID mice at 2 months post-transplant (39.5% engraftment v. 0.2-2% in the non-cultured group, FIG. 18) as well as enhanced secondary transplantation. Zhang et al. Blood. 2008; 111(7): 3415-3423. Moreover, whereas Notch signaling inhibits differentiation allowing HSPC self-renewal, Angptl proteins enhance in vivo HSPC repopulation in the absence of in vitro evidence demonstrating altered differentiation or HSC expansion. Aspects of the current disclosure are accordingly based on the hypothesis that because these physiologic ligands function by two distinct mechanisms, the combination may result in generation of more effective repopulating cells. This hypothesis was tested in Example 2 to further examine whether combined effects of Delta1- and Angptls, such as Angptl5, enhance HSC expansion, allowing improvement over current cellular therapies relevant for clinical applications.

Based in part on the described data and hypotheses, the Notch agonist Delta 1 in combination with Angptl5 was selected for further study. However, culture conditions optimized for Delta$^{Ext-TgG}$ and Angptl5 are quite distinct. Optimal Delta$^{Ext-IgG}$-induced expansion was found following 16-17 days culture in StemSpan serum-free media in the presence of SCF, Flt3-ligand (Flt3L), TPO, IL-6 and IL-3, with immobilized Delta$^{Ext-IgG}$ and retronectin. By contrast, Angptl5-induced expansion was optimal following 10 days culture in StemSpan media, but with low-doses of the cytokines SCF, TPO as well as FGF1, heparin, and IGFBP2. Accordingly, success of the combination could not be predicted.

3.2.1. Example 2—Methods

Cell Isolation. Human CB for research was obtained from normal deliveries under Swedish Medical Center Institutional Review Board (Seattle) approval after consent was obtained. Samples were incubated in ammonium chloride red blood cell lysis buffer, washed, and suspended in phosphate-buffered saline (PBS) with 2% human type AB serum. Cells were incubated with CD34+ immunomagnetic beads (Miltenyi Biotec) and purified using a Miltenyi AutoMACS and then frozen. CD34+ cells were then thawed for individual experiments.

Generation and immobilization of Delta$^{Ext-IgG}$ protein and LILRB2 antibody (anti-CD85d). Generation of the construct encoding the extracellular domain of Delta1 fused to the fc domain of human IgG1 and purification of Delta$^{Ext-IgG}$ protein from culture medium of NSO cells electroporated with the construct have been previously described (Varnum-Finney, J Cell Sci. 2000; 113(pt23): 4313-4318). Human CD85d biotinylated antibody (polyclonal goat IgG) or normal goat IgG biotinylated control were obtained from R&D Systems. Wells of non-tissue culture-treated culture plates or non-tissue culture-treated flasks were incubated with Delta$^{Ext-IgG}$ (0.5 or 2.5 µg/ml), CD85d biotinylated antibody (range 0.08 to 25 µg/ml), or IgG control diluted in PBS together with 5 µg/ml retronectin, incubated overnight at 4° C., and washed generously with PBS.

Cell Cultures. Cells were cultured in serum-free medium (Stemspan Serum Free Expansion Medium; StemCell Technologies) with 50 ng/ml human stem cell factor (SCF), human Flt3-ligand, human interleukin 6 (IL-6), thrombopoietin (TPO), 10 ng/ml human interleukin 3 (IL-3), FGF1 20 ng/ml, and heparin 10 µg/ml. Cultures for transplant were initiated in 25 cm$^2$ non-tissue cultured treated flasks with between 1 and 1.2×10$^5$ starting CD34+ cells/flask. Cells were expanded to 75 and 125 cm$^2$ non-tissue cultured treated flasks when cell density reached approximately 1-1.5×10$^6$ cells/ml. Fresh medium with cytokines was added every 3-4 days.

Transplantation of human hematopoietic cells into NOD/SCID gamma null mice. Sublethally irradiated (275 rad) NOD-SCID IL-2Ry-null mice (NSG) approved for use by the Fred Hutchinson Cancer Research Center Institutional Animal Care and Use Committee were used for transplant. Single mice (5-8 mice/group) were infused with the progeny generated from 1×10$^5$ started CD34+ cells. Repopulating ability (percent human CD45+ or CD45+33+, CD 45+19+, CD45+34+ in marrow) was assessed at 2 and 8 weeks after transplantation using bone marrow aspirated from the femur of anesthetized recipient mice.

Statistical Analysis. Unpaired, two-tailed t-tests were used to make comparisons between groups

3.2.2. Example 2—Results

Figure 19:
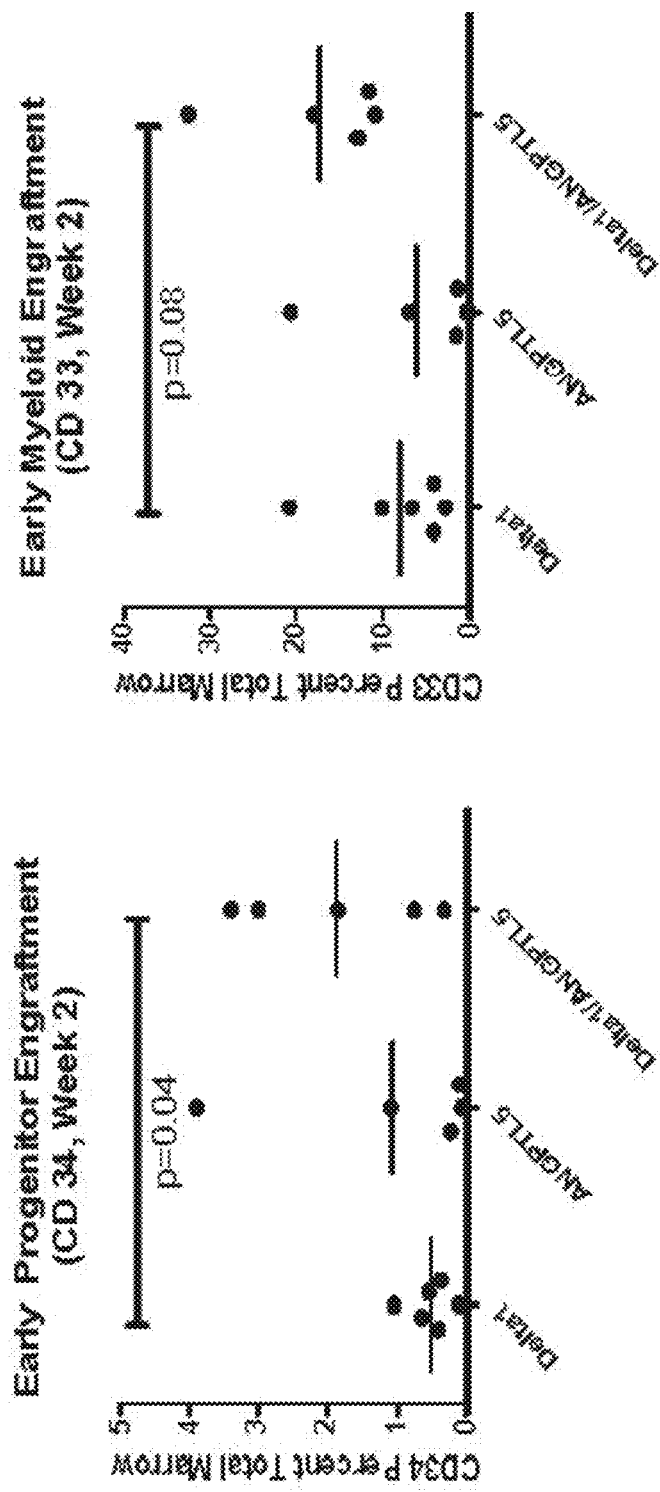
FIG. 19. Culture of CB HSPC in the presence of Delta1 and Angplt5 enhances early progenitor and myeloid precursor cell repopulation. CD34+ CB HSPC cultured in the presence of Delta1, Angptl5, or the combination were transplanted into immunodeficient mice (circles are individual mice, line is median engraftment for group) and progenitor (CD34) and myeloid (CD33) engraftment assessed at an early time point (2 weeks post-transplant). P-values represent two-tailed t-test.
Figure 20:
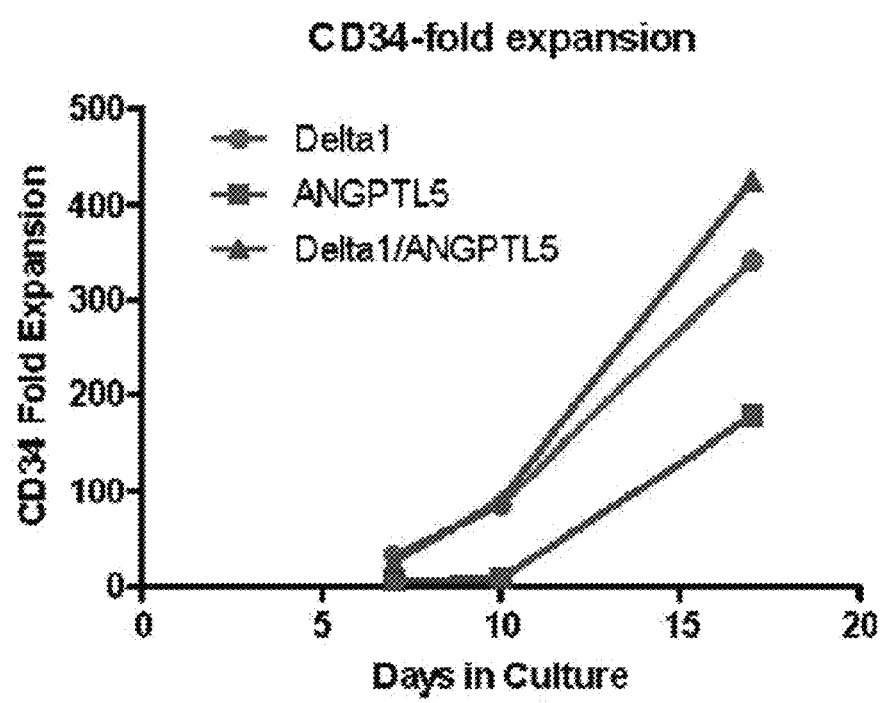
FIG. 20. CD34-fold expansion of CB HSPC cultured in the presence of Notch alone, Angptl5 alone, or the combination. CD34+ CB HSPC were cultured for 16 days in the presence of Delta1, Angptl5, or the combination. CD34 fold expansion (CD34 cells generated/starting number CD34 cells) was calculated for time points represented (days 7, 10, 16).

The combined effects of Delta1 and Angptl5 enhanced generation of CB-derived CD34+ cells that rapidly repopulate the marrow of immune deficient mice with hematopoietic precursors and differentiating myeloid cells. Particularly, in studies combining Delta1 and Angptl5, significantly enhanced rapid (2 week) repopulation of NSG mice by CD34+ precursors (p=0.04) and a clear trend towards enhanced repopulation by immature, CD33+ myeloid precursors (p=0.08 two-tailed t-test, p=0.04 Mann-Whitney test for possible non-Gaussian distribution) was found compared to using Delta1 or Angptl5 alone (FIG. 19). Importantly, this occurred despite overall similar CD34-fold expansion with CB HSPC cultured on Delta1 alone (FIG. 20). Additionally, there was no difference in generation of CD34+CD90$^{lo}$ or CD49f cells suggesting generation of greater numbers of rare, rapidly repopulating cells, or cells with altered cell-cycle, apoptotic, or transcriptional or epigenetic properties. Of note, this combination maintained multi-lineage engraftment 8 weeks after transplant suggesting maintenance or expansion of longer term repopulating cells.

Figure 21:
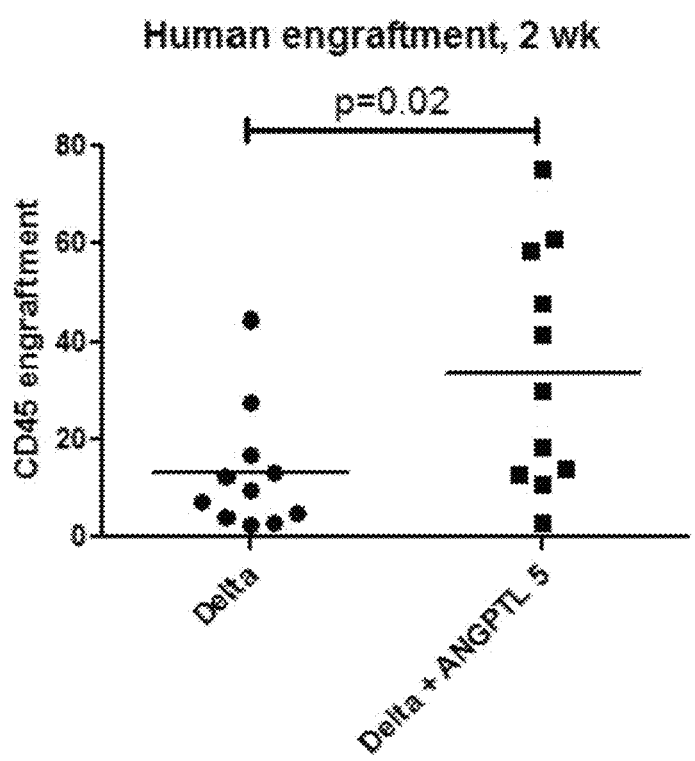
FIG. 21. Significantly enhanced early marrow repopulation is seen when Delta is combined with Angptl5 and cultured in conditions optimized for Delta-mediated expansion.

FIG. 21 shows significantly enhanced early marrow repopulation when Delta is combined with Angptl5 and cultured in conditions optimized for Delta-mediated expansion.

Figure 22:
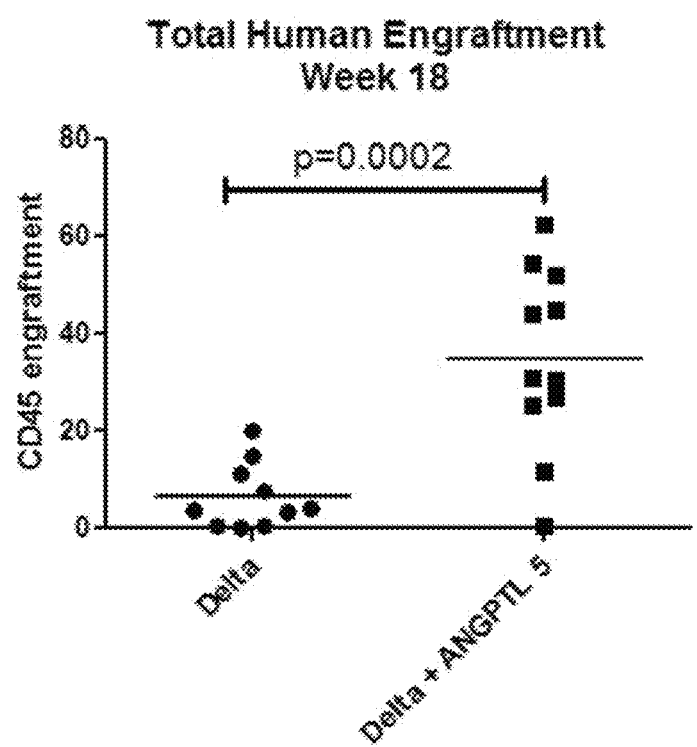
FIG. 22. Longer-term repopulation is significantly enhanced as well; repopulation is multi-lineage showing significantly enhanced myeloid and lymphoid lineages. Cells did not have significant secondary engraftment when cultured in conditions previously optimized for Delta-mediated expansion.

FIG. 22 shows longer-term repopulation is significantly enhanced when Delta is combined with Angptl5 and cultured in conditions optimized for Delta-mediated expansion; repopulation is multi-lineage showing significantly enhanced myeloid and lymphoid lineages. Cells did not have significant secondary engraftment when cultured in conditions previously optimized for Delta-mediated expansion.

Figure 23A:
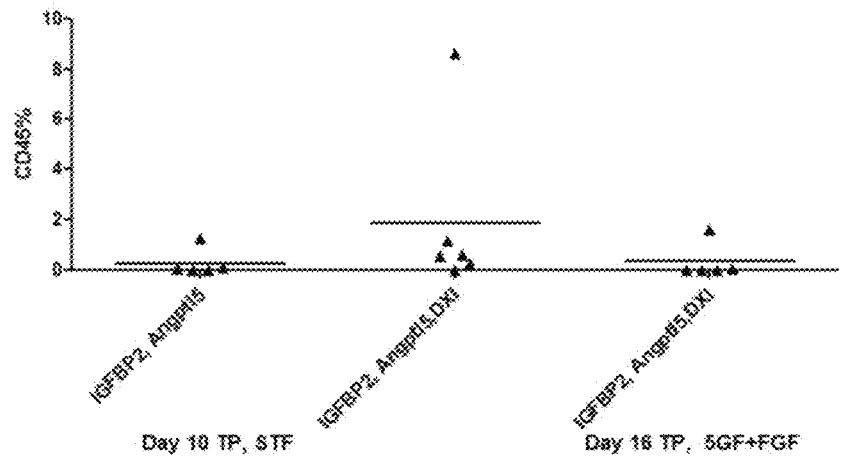
FIGS. 23A and 23B show that culture with Delta and Angptl5 with lower cytokine concentrations results in secondary engraftment previously not seen in Delta expanded cells suggesting maintenance/expansion of a longer-term repopulating cell when Delta is added to ANGPTL5 in these conditions.
Figure 23B:
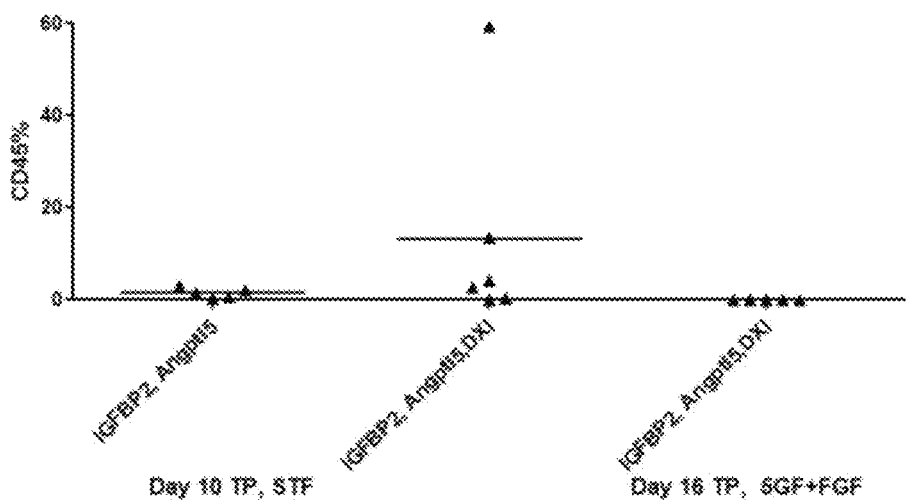

FIGS. 23A and 23B show that culture with Delta and Angptl5 with lower cytokine concentrations results in secondary engraftment previously not seen in Delta expanded cells suggesting maintenance/expansion of a longer-term repopulating cell when Delta is added to Angptl5 in these conditions.

Figure 24:
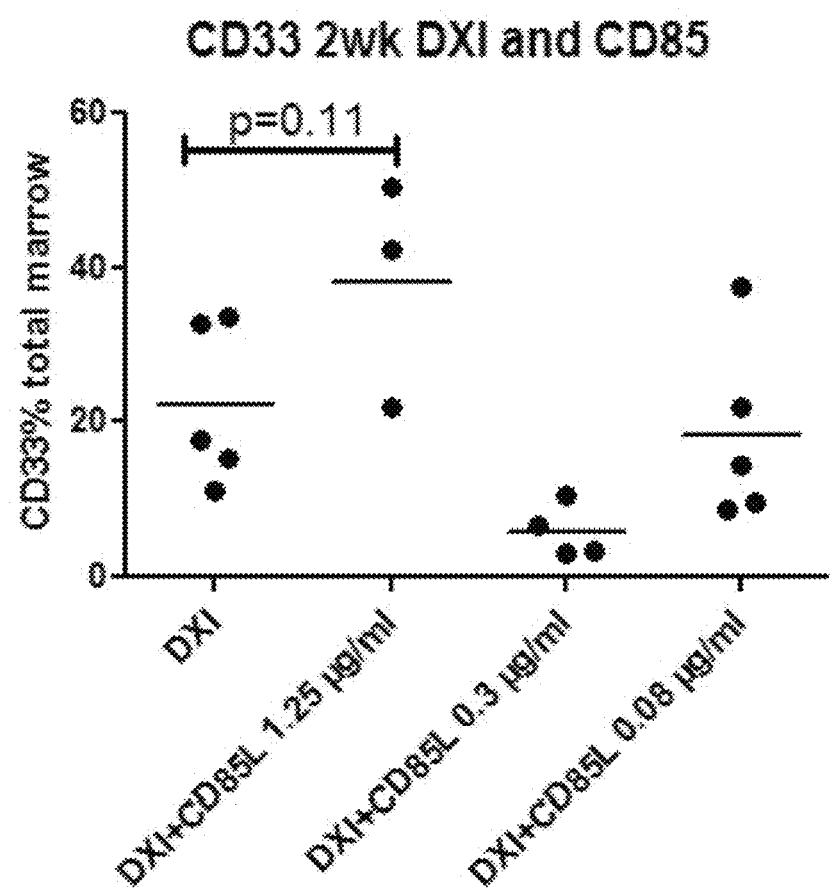
FIG. 24. Culture with Delta and an antibody to the Angptl5 receptor (LILRB2 or CD85) trends towards enhanced early myeloid engraftment as compared to Delta alone. This trend is present at the highest dose of CD85 used in this experiment.

FIG. 24. Culture with Delta and an antibody to the Angptl5 receptor (LILRB2 or CD85) trends towards enhanced early myeloid engraftment as compared to Delta alone. This trend is present at the highest dose of CD85 used in this experiment.

Figure 25:
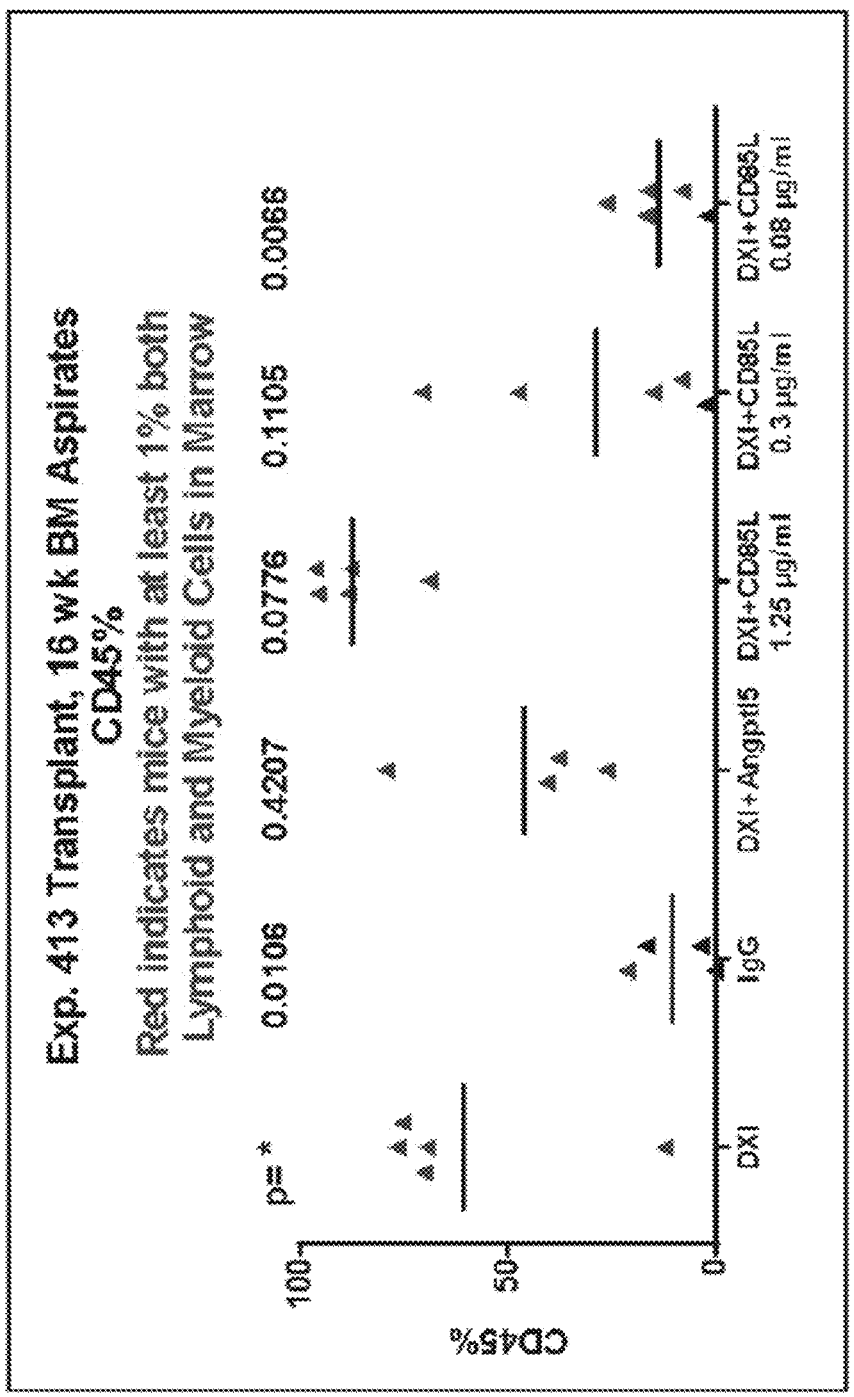
FIG. 25. When engraftment was assessed at a longer-term time point (16 wks after transplant), engraftment of cells cultured with Delta and antibody to the Angptl5 receptor (LILRB2 or CD85) had greater engraftment than Delta alone. These cells are able to repopulate both lymphoid and myeloid lineages.

FIG. 25. When engraftment was assessed at a longer-term time point (16 wks after transplant), engraftment of cells cultured with Delta and CD85 had greater engraftment than Delta alone. These cells are able to repopulate both lymphoid and myeloid lineages.

Accordingly, Example 2 demonstrates the development of culture conditions for expanding HSC using Delta1 and Angptl5 with cytokine compositions and time in culture. Significantly enhanced early marrow repopulation in immune-deficient mice from CB hematopoietic stem/progenitor cells (HSPC) cultured with Delta1 and Angptl5 as compared to Delta1 alone is demonstrated. Further, data demonstrating improved longer-term repopulation of CB HSPC following culture with Delta1 and Angptl5 as compared to either approach alone is provided.

3.3 Example 3

The focus of this Example is on optimizing generation of CB hematopoietic stem/progenitor cells (HSPC) by investigating not only culture conditions but also presentation of Delta1 and anti-LILRB2 antibody.

Figure 26:
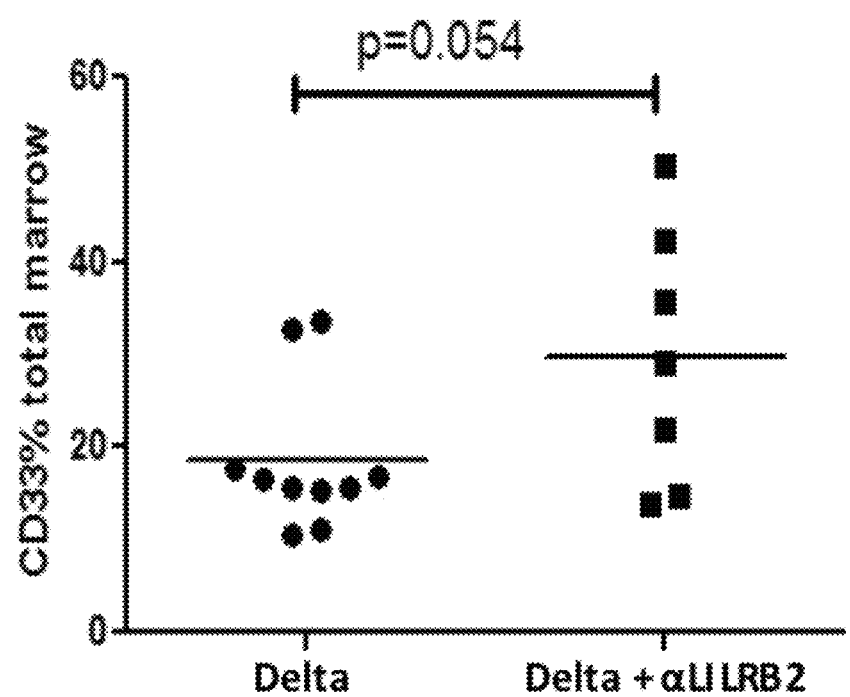
FIG. 26. CD34+ cord blood hematopoietic stem/progenitor cells were cultured with Delta1 or a combination of Delta1 and anti-LILRB2 antibody (αLILRB2). The progeny of 10,000 starting cells were transplanted into NSG mice (circles=individual mice, lines=mean engraftment) and myeloid engraftment (y-axis: CD33+ cells in total marrow) was assessed at 2 weeks. P-value represents two tailed t-test.
Figure 27:
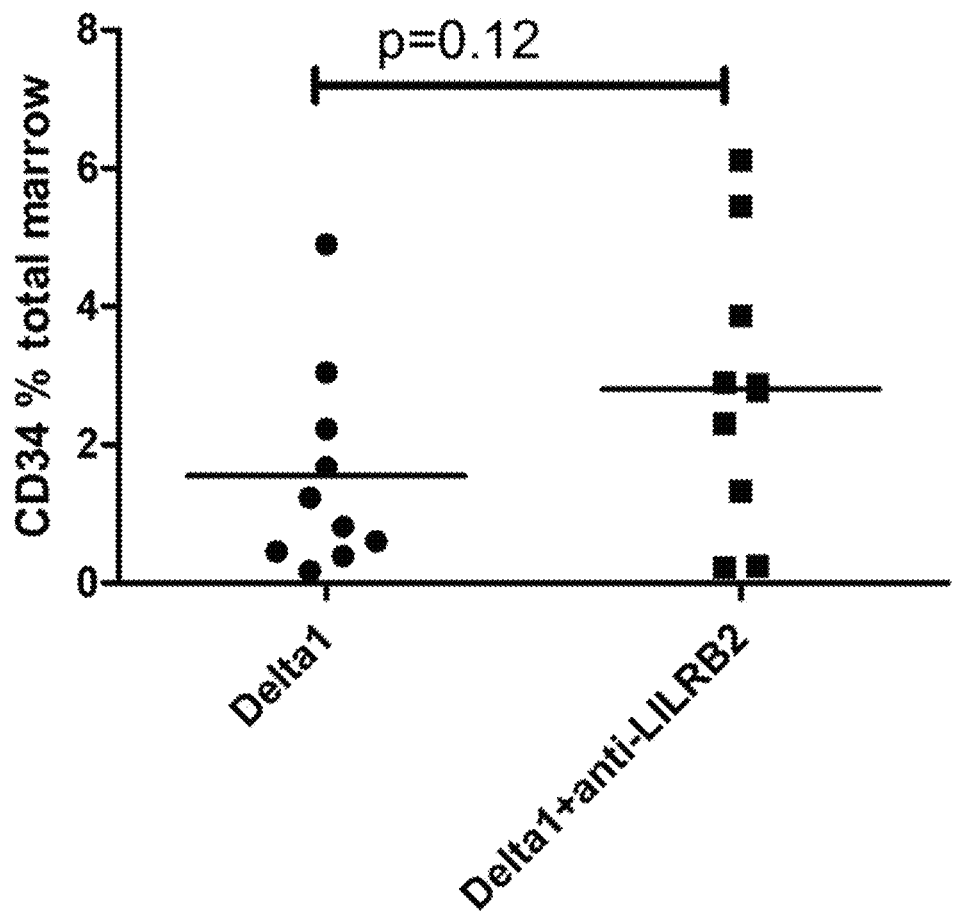
FIG. 27. CD34+ cord blood hematopoietic stem/progenitor cells were cultured with Delta1 or a combination of Delta1 and anti-LILRB2 antibody (αLILRB2). The progeny of 10,000 starting cells were transplanted into NSG mice (circles=individual mice, lines=mean engraftment) and progenitor engraftment (y-axis: % CD34+ cells in total marrow) was assessed at 10 weeks. P-value represents two tailed t-test.

Use of an immobilized antibody against LILRB2 (CD85d), an Angiopoietin-like (ANGPTL) protein receptor, was investigated. Interaction of LILRB2 and ANGPTL protein allows for the ex vivo expansion of CB HSPC, including those with in vivo repopulating ability. In initial studies, combination of immobilized Delta1 with an intermediate concentration of anti-LILRB2 antibody led to the increased generation of CD34+ and CD34+CD90$^{lo}$ cells (CD90$^{lo}$ cells were those cells expressing low amounts of CD90, as determined by a gated cut-off amount) compared to culture with Delta1 or anti-LILRB2 antibody alone (data not shown). Transplantation experiments into NSG mice to optimize culture conditions for maximal generation of rapid myeloid repopulating cells demonstrated improved generation of cells using previously established cytokine culture conditions and immobilized anti-LILRB2 antibody at concentration of 1.25 µg/ml (data not shown). Upon transplant into NSG mice, the combined activation of Notch and LILRB2 receptors enhanced the generation of rapidly repopulating myeloid precursors compared to Delta1 alone (29.3% vs. 18.6% total human CD33+ cells in NSG mice at 2 weeks post-transplant, p=0.05) (FIG. 26). Culture in these conditions may also enhance generation of longer-term repopulating cells as shown by greater progenitor cell engraftment with the combination (2.9% vs. 1.7% total human CD34+ cells in NSG mice at 10 weeks post-transplant) (FIG. 27).

Figure 28:
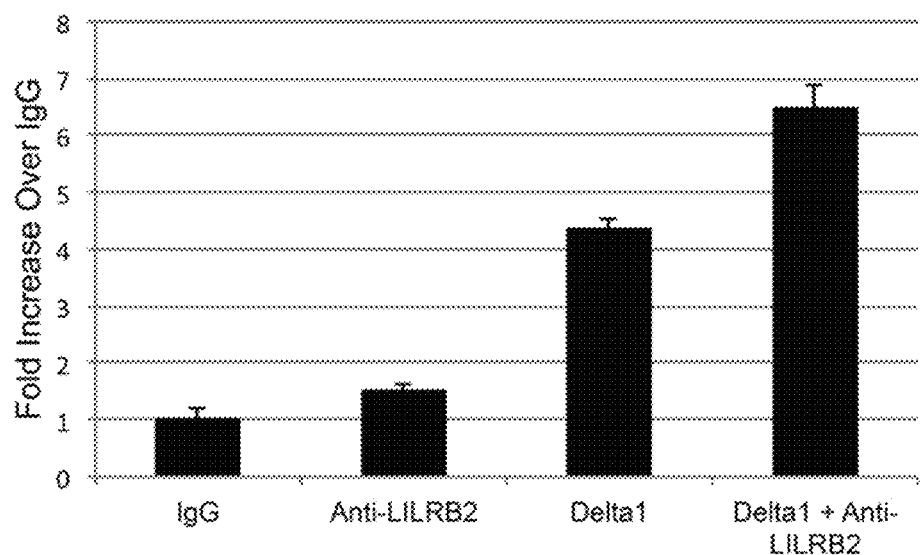
FIG. 28. Cord blood CD34+ cells were cultured for 4 hrs in non-tissue culture wells coated with retronectin and either i) IgG (human), ii) anti-LILRB2 antibody (αLILRB2), iii) Delta1, or (iv) a combination of αLILRB2 and Delta1. HES1 expression was assessed by qPCR and normalized to expression of the β-glucuronidase (GUSB) reference gene.

Enhanced Hes1 (a Notch target gene) expression was observed in cells cultured with the combination of Delta1 and anti-LILRB2 antibody over Delta1 alone, with all reagents immobilized on the plastic of the culture dish (FIG. 28).

Studies investigating alternate methods of agonist presentation were performed, specifically comparing the effectiveness of agonist immobilized on magnetic protein A-microbeads with immobilization to the culture flask. Data suggest that presentation of Delta1 and anti-LILRB2 antibodies induced greater Hes1 expression when the two agonists were presented by alternate means, e.g. Delta1 immobilized on plastic and anti-LILRB2 antibody immobilized on beads (FIG. 29).

Amplification in the production of CD7+ cells accompanying the increased Hes1 expression has not been observed, suggesting that the expression of T cell genes are unaffected. Without being bound by any particular theory, these data suggest that the activation of the ANGPTL5/LILRB2 pathway is not amplifying the effects of Notch signaling, but acts in parallel with Notch, perhaps at the Hes1 gene level, to inhibit myeloid differentiation and enhance HSPC self-renewal.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients and to those that do not materially affect the embodiment. As used herein, a material effect would cause a statistically significant reduction in precursor cell expansion by the methods disclosed herein as measured by an assay described in relation to effective amounts.

Unless otherwise indicated, all numbers used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to publications, patents and/or patent applications (collectively "references") throughout this specification. Each of the cited references is individually incorporated herein by reference for their particular cited teachings.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, $3^{rd}$ Edition or a dictionary known to those of ordinary skill in the art, such as the Oxford Dictionary of Biochemistry and Molecular Biology (Ed. Anthony Smith, Oxford University Press, Oxford, 2004).

Various references such as patents, patent applications, and publications are cited herein, the disclosures of which are hereby incorporated by reference herein in their entireties.

The invention claimed is:

1. A method of expanding hematopoietic stem cells and hematopoietic progenitor cells ex vivo, comprising culturing said cells with (i) a Notch agonist and (ii) a leukocyte immunoglobulin-like receptor B2 (LILRB2) agonist immobilized on a first solid phase, wherein the immobilized LILRB2 agonist is an antibody to the LILRB2 receptor, or an antigen-binding fragment of said antibody.

2. The method of claim 1, wherein the hematopoietic stem cells and hematopoietic progenitor cells are human cells.

3. The method of claim 2, wherein the hematopoietic stem cells and hematopoietic progenitor cells are obtained from bone marrow, umbilical cord blood, placental blood, or Wharton's jelly.

4. The method of claim 1, wherein the antibody to the LILRB2 receptor is a monoclonal antibody.

5. The method of claim 1, wherein the antibody to the LILRB2 receptor is a polyclonal antibody.

6. The method of claim 1, wherein the LILRB2 agonist is an Fv, Fab, Fab', $F(ab')_2$, or single chain Fv fragment (scFv).

7. The method of claim 1, wherein LILRB2 agonist binds to the Ig1 domain of LILRB2.

8. The method of claim 1, wherein LILRB2 agonist binds to the Ig4 domain of LILRB2.

9. The method of claim 1, wherein the first solid phase is the surface of a tissue culture dish.

10. The method of claim 1, wherein the Notch agonist is immobilized on the first solid phase.

11. The method of claim 1, wherein the Notch agonist is immobilized on a second solid phase that is not the first solid phase.

12. The method of claim 1, wherein the Notch agonist is an extracellular, Notch-interacting domain of a Delta protein.

13. The method of claim 1, wherein the Notch agonist is Delta$^{ext-IgG}$.

14. The method of claim 1, wherein the Notch agonist is an antibody that specifically binds to Notch-1.

15. The method of claim 1, wherein the Notch agonist is an antibody that specifically binds to Notch-2.

16. The method of claim 1, wherein the culturing step is performed in the presence of a culture medium comprising stem cell factor (SCF), thrombopoietin (TPO), and Flt3-ligand.

17. The method of claim 1, wherein the culturing step is performed in the presence of a culture medium comprising SCF, Flt3-ligand, interleukin-6 (IL-6), TPO, fibroblast growth factor-1 (FGF1), and interleukin-3 (IL-3).

18. The method of claim 17, wherein the culture medium comprises SCF, Flt3-ligand, IL-6, TPO, FGF1, IL-3, and heparin.

19. The method of claim 1, wherein the culturing step is performed in the presence of a culture medium comprising retronectin.

\* \* \* \* \*